(12) United States Patent
Lawson et al.

(10) Patent No.: US 9,365,566 B2
(45) Date of Patent: Jun. 14, 2016

(54) CINNOLINE DERIVATIVES

(71) Applicant: Takeda Pharmaceutical Company Limited, Osaka (JP)

(72) Inventors: John David Lawson, San Diego, CA (US); Mark Sabat, San Diego, CA (US); Christopher Smith, San Diego, CA (US); Haixia Wang, San Diego, CA (US); Young K. Chen, San Diego, CA (US); Toufike Kanouni, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/381,187

(22) PCT Filed: Mar. 25, 2013

(86) PCT No.: PCT/US2013/033757
§ 371 (c)(1),
(2) Date: Aug. 26, 2014

(87) PCT Pub. No.: WO2013/148603
PCT Pub. Date: Oct. 3, 2013

(65) Prior Publication Data
US 2015/0038510 A1 Feb. 5, 2015

Related U.S. Application Data

(60) Provisional application No. 61/616,353, filed on Mar. 27, 2012.

(51) Int. Cl.
| | | |
|---|---|---|
| *C07D 471/04* | (2006.01) |
| *C07D 413/14* | (2006.01) |
| *C07D 401/04* | (2006.01) |
| *C07D 403/04* | (2006.01) |
| *C07D 407/14* | (2006.01) |
| *C07D 409/14* | (2006.01) |
| *C07D 417/14* | (2006.01) |
| *A61K 31/502* | (2006.01) |
| *A61K 31/5377* | (2006.01) |
| *A61K 45/06* | (2006.01) |
| *C07D 403/14* | (2006.01) |
| *C07D 405/14* | (2006.01) |

(52) U.S. Cl.
CPC ............ *C07D 471/04* (2013.01); *A61K 31/502* (2013.01); *A61K 31/5377* (2013.01); *A61K 45/06* (2013.01); *C07D 401/04* (2013.01); *C07D 403/04* (2013.01); *C07D 403/14* (2013.01); *C07D 405/14* (2013.01); *C07D 407/14* (2013.01); *C07D 409/14* (2013.01); *C07D 413/14* (2013.01); *C07D 417/14* (2013.01)

(58) Field of Classification Search
CPC ...................................................... A61K 31/535
USPC ....................................... 514/234.5; 544/119
See application file for complete search history.

(56) References Cited

FOREIGN PATENT DOCUMENTS

| WO | WO/2007/073283 | 6/2007 |
| WO | WO/2008/090353 | 6/2008 |

OTHER PUBLICATIONS

Uckun, Fatih M. et al. "Bruton's tyrosine kinase as a molecular target in treatment of leukemias and lymphomas as well as inflammatory disorders and autoimmunity" Expert Opinion on Therapeutic Parents, 2010, vol. 20. No. 11, pp. 1457-1470.
Scott, David A. et al. "3-Amino-4-anilinochinnolines as a novel class of CSF-1R inhibitor" Bioorganic and Medicinal Chemistry Letters, 2011, vol. 21, No. 5, pp. 1382-1384.
Pan, Zhengying et al. "Discovery of selective irreversible inhibitors for Bruton's Tyrosine Kinase", 2007, ChemMedChem, vol. 2, No. 1, pp. 58-61.
International search report and the written opinion of the international searching authority in international application No. PCT/US2013/033757, dated May 7, 2013.

*Primary Examiner* — Paul V Ward
(74) *Attorney, Agent, or Firm* — Matthew J. Russo

(57) ABSTRACT

Disclosed are compounds of Formula 1,

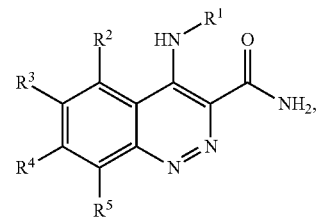

and pharmaceutically acceptable salts thereof, wherein $R^1$, $R^2$, $R^3$, $R^4$, and $R^5$ are defined in the specification. The compounds are inhibitors of Bruton's tyrosine kinase (BTK). This disclosure also relates to materials and methods for preparing compounds of Formula 1, to pharmaceutical compositions which contain them, and to their use for treating diseases, disorders or conditions associated with BTK.

16 Claims, No Drawings

CINNOLINE DERIVATIVES

CROSS-REFERENCE TO RELATED APPLICATIONS

This application is the U.S. National Stage entry under 35 U.S.C. §371(c) of International Application PCT/US2013/033757, filed Mar. 25, 2013, which claims the benefit of U.S. Provisional Application No. 61/616,353, filed Mar. 27, 2012, which is herein incorporated by reference.

FIELD OF THE INVENTION

This invention relates to substituted cinnoline derivatives and related compounds, which are inhibitors of Bruton's tyrosine kinase (BTK), to pharmaceutical compositions which contain them, and to the use of the inhibitors to treat diseases, disorders, and conditions associated with BTK.

BACKGROUND OF THE INVENTION

BTK is a member of the TEC family of non-receptor protein tyrosine kinases, and it is involved in the regulation of B-cell development, activation, and survival through B-cell antigen receptor (BCR) signaling. See W. N. Khan et al., *Immunity* 3:283-299 (1995); and A. B. Satterthwaite and O. N. Witte, *Immunol. Rev.* 175:120-127 (2000). Mutation of the gene encoding BTK in humans leads to a condition known as X-linked agammaglobulinemia (XLA), which is characterized by reduced immune function, including impaired maturation of B cells, decreased levels of immunoglobulin and peripheral B cells, diminished T-cell independent immune response, and attenuated calcium mobilization following BCR stimulation. See F. S. Rosen et al., *N. Engl. J. Med.* 333(7):431-440 (1995); and J. M. Lindvall et al., *Immunol. Rev.* 203:200-215 (2005).

BTK's key role in B-cell development and the BCR signaling pathway suggests that inhibition of BTK may provide therapeutic benefit for the treatment of lymphoma, inflammatory disorders, and autoimmune diseases, among others. Clinical studies involving the depletion of mature B cells via treatment with rituximab indicate that rheumatoid arthritis, systemic lupus erythematosus (SLE), and multiple sclerosis may result from the over expression of B cells. See J. C. Edwards et al., *N. Engi. J. Med.* 350:2572-81 (2004); C. Favas and D. A. Isenberg *Nat. Rev. Rheumatol.* 5:711-16 (2009); and S. L. Hauser et al. *N. Engl. J. Med.* 358:676-88 (2008). Other studies suggest that the BCR pathway may be involved in the survival of tumor cells in non-Hodgkin lymphoma and diffuse large B-cell lymphoma. See R. Küppers, *Nat. Rev. Cancer* 5:251-62 (2005); and R. E. Davis et al., *Nature* 463:88-92 (2010). In preclinical studies, BTK-deficient mice have demonstrated decreased disease progression in murine models of SLE and resistance to collagen-induced arthritis. See M. J. Shlomchik et al., *J. Exp. Med.* 180:1295-1306 (1994); and L. Jansson and R. Holmdahl, *Clin. Exp. Immunol.* 94(3):459-65 (1993). Furthermore, a selective irreversible BTK inhibitor has been shown to completely suppress collagen-induced arthritis in mice, to inhibit autoantibody production and the development of kidney disease in a mouse model for SLE, and to induce objective clinical responses in dogs with spontaneous B-cell non-Hodgkin lymphoma. See L. A. Honigberg et al., *Proc. Natl. Acad. Sci. USA* 107(29):13075-80 (2010).

Certain inhibitors of Bruton's tyrosine kinase are described in WO 99/54286 A2, WO 2002/50071 A1, WO 2007/087068 A2, WO 2008/039218 A2, WO 2008/121742 A2, WO 2007/147771 A2, WO 2009/077334 A1, WO 2009/098144 A1, WO 2009/156284 A1, WO 2010/000633 A1, WO 2010/006947 A1, WO 2008/033834 A1, WO 2010/056875 A1, WO 2010/068788 A1, and WO 2010/068810 A2.

SUMMARY OF THE INVENTION

This invention provides substituted cinnoline derivatives and related compounds, and pharmaceutically acceptable salts thereof. This invention also provides pharmaceutical compositions that contain the substituted cinnolines and provides for their use to treat diseases, disorders and conditions associated with BTK inhibition.

One aspect of the invention provides compounds of Formula 1:

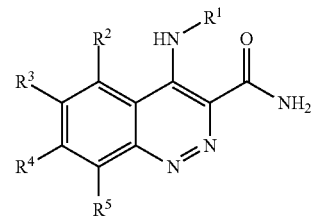

or a pharmaceutically acceptable salt thereof, wherein:
$R^1$ is hydrogen;
$R^2$ is selected from hydrogen, halo, —CN, $C_{1-4}$ alkyl, $C_{1-4}$ haloalkyl, —$NO_2$, and —$OR^{14}$;
$R^3$ is selected from hydrogen, halo, —CN, $C_{1-4}$ alkyl, $C_{1-4}$ haloalkyl, —$NO_2$, —$OR^{14}$, and $C_{2-6}$ heterocyclyl optionally substituted with from one to three substituents independently selected from halo, hydroxy, oxo, and —CN;
$R^4$ is selected from hydrogen, halo, —CN, $C_{1-4}$ alkyl, $C_{1-4}$ haloalkyl, —$NO_2$, and —$OR^{14}$;
$R^5$ is a bicyclic $C_{6-9}$ heteroaryl having from one to four heteroatoms, each of the heteroatoms being nitrogen, wherein the bicyclic $C_{6-9}$ heteroaryl is optionally substituted with from one to five substituents independently selected from halo, oxo, —CN, $R^6$, and $R^7$;
each $R^6$ is independently selected from —$OR^8$, —$N(R^8)R^9$, —$NR^8C(O)R^9$, —$NHC(O)NR^8R^9$, —$NR^8C(O)NHR^9$, —$C(O)R^8$, —$C(O)OR^8$, —$C(O)N(R^8)R^9$, —$C(O)N(R^8)OR^9$, —$C(O)N(R^8)S(O)_2R^7$, —$N(R^8)S(O)_2R^7$, —$SR^8$, —$S(O)R^7$, —$S(O)_2R^7$, and —$S(O)_2N(R^8)R^9$;
each $R^7$ is independently selected from
  (a) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
  (b) $C_{3-10}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;
each $R^8$ and $R^9$ is independently selected from
  (a) hydrogen;
  (b) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
  (c) $C_{3-10}$ cycloalkyl-$(CH_2)_m$—, $C_{6-14}$ aryl-$(CH_2)_m$—, $C_{2-6}$ heterocyclyl-$(CH_2)_m$—, and $C_{1-9}$ heteroaryl-$(CH_2)_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;

each $R^{10}$ is independently selected from —$OR^{11}$, —$N(R^{11})R^{12}$, —$N(R^{11})C(O)R^{12}$, —$NHC(O)NR^{11}R^{12}$, —$NR^{11}C(O)NHR^{12}$, —$C(O)R^{11}$, —$C(O)OR^{11}$, —$C(O)N(R^{11})R^{12}$, —$C(O)N(R^{11})OR^{12}$, —$C(O)N(R^{11})S(O)_2R^{13}$, —$NR^{11}S(O)_2R^{13}$, —$SR^{11}$, —$S(O)R^{13}$, —$S(O)_2R^{13}$, and —$S(O)_2N(R^{11})R^{12}$;

each $R^{11}$ and $R^{12}$ is independently selected from
(a) hydrogen; and
(b) $C_{1-6}$ alkyl and $C_{3-10}$ cycloalkyl-$(CH_2)_m$—, each optionally substituted with from one to five substituents independently selected from halo, oxo, —CN, —OH, and —$NH_2$;

each $R^{13}$ is independently selected from $C_{1-6}$ alkyl and $C_{3-10}$ cycloalkyl-$(CH_2)_m$—, each optionally substituted with from one to five substituents independently selected from halo, oxo, —CN, —OH, and —$NH_2$;

each $R^{14}$ is independently selected from hydrogen, $C_{1-4}$ alkyl, and $C_{1-4}$ haloalkyl; and each m is independently selected from 0, 1, 2, 3, and 4;

wherein each heteroaryl and heterocyclyl moiety of $R^3$, $R^7$, $R^8$, and $R^9$ independently has one to four heteroatoms, each of the heteroatoms independently selected from N, O, and S.

Another aspect of the invention provides a compound which is selected from the group of compounds described in the examples or a pharmaceutically acceptable salt thereof or a stereoisomer of any one of the compounds in the examples or a pharmaceutically acceptable salt thereof.

A further aspect of the invention provides a pharmaceutical composition which includes: a compound of Formula 1 or a pharmaceutically acceptable salt thereof or a compound selected from the group of compounds and their pharmaceutically acceptable salts as defined in the preceding paragraph; and a pharmaceutically acceptable excipient.

An additional aspect of the invention provides a compound of Formula 1 or a pharmaceutically acceptable salt thereof or a compound selected from the group of compounds and their pharmaceutically acceptable salts as defined above, for use as a medicament.

Another aspect of the invention provides a use of a compound of Formula 1 or a pharmaceutically acceptable salt thereof or a compound selected from the group of compounds and their pharmaceutically acceptable salts as defined above, for the manufacture of a medicament for the treatment of a disease, disorder or condition associated with BTK.

A further aspect of the invention provides a method of treating a disease, disorder or condition in a subject, the method comprising administering to the subject an effective amount of a compound of Formula 1 or a pharmaceutically acceptable salt thereof or a compound selected from the group of compounds and their pharmaceutically acceptable salts as defined above, wherein the disease, disorder or condition is associated with BTK.

An additional aspect of the invention provides a method of treating a disease, disorder or condition in a subject, the method comprising administering to the subject an effective amount of a compound of Formula 1 or a pharmaceutically acceptable salt thereof or a compound selected from the group of compounds and their pharmaceutically acceptable salts as defined above, wherein the disease, disorder or condition is selected from Type I hypersensitivity reactions, autoimmune diseases, inflammatory disorders, cancer, and non-malignant proliferative disorders.

Another aspect of the invention provides a method of treating a disease, disorder or condition in a subject, the method comprising administering to the subject an effective amount of a compound of Formula 1 or a pharmaceutically acceptable salt thereof or a compound selected from the group of compounds and their pharmaceutically acceptable salts as defined above, wherein the disease, disorder or condition is selected from allergic rhinitis, asthma, atopic dermatitis, rheumatoid arthritis, multiple sclerosis, systemic lupus erythematosus, psoriasis, immune thrombocytopenic purpura, inflammatory bowel disease, chronic obstructive pulmonary disease, Sjögren's syndrome, ankylosing spondylitis, Behcet's disease, pemphigus vulgaris, idiopathic plasmacytic lymphadenopathy, atherosclerosis, myocardial infarction, and thrombosis.

Another aspect of the invention provides a method of treating a disease, disorder or condition in a subject, the method comprising administering to the subject an effective amount of a compound of Formula 1 or a pharmaceutically acceptable salt thereof or a compound selected from the group of compounds and their pharmaceutically acceptable salts as defined above, wherein the disease, disorder or condition is selected from B-cell lymphoma, chronic lymphocytic leukemia, and multiple myeloma.

A further aspect of the invention provides a combination of an effective amount of a compound of Formula 1 or a pharmaceutically acceptable salt thereof or a compound selected from the group of compounds and their pharmaceutically acceptable salts as defined above, and at least one additional pharmacologically active agent.

DETAILED DESCRIPTION OF THE INVENTION

Unless otherwise indicated, this disclosure uses definitions provided below.

"Substituted," when used in connection with a chemical substituent or moiety (e.g., a $C_{1-6}$ alkyl group), means that one or more hydrogen atoms of the substituent or moiety have been replaced with one or more non-hydrogen atoms or groups, provided that valence requirements are met and that a chemically stable compound results from the substitution.

"About" or "approximately," when used in connection with a measurable numerical variable, refers to the indicated value of the variable and to all values of the variable that are within the experimental error of the indicated value or within ±10 percent of the indicated value, whichever is greater.

"Alkyl" refers to straight chain and branched saturated hydrocarbon groups, generally having a specified number of carbon atoms (e.g., $C_{1-4}$ alkyl refers to an alkyl group having 1 to 4 (i.e., 1, 2, 3 or 4) carbon atoms, $C_{1-6}$ alkyl refers to an alkyl group having 1 to 6 carbon atoms, and so on). Examples of alkyl groups include methyl, ethyl, n-propyl, i-propyl, n-butyl, s-butyl, i-butyl, t-butyl, pent-1-yl, pent-2-yl, pent-3-yl, 3-methylbut-1-yl, 3-methylbut-2-yl, 2-methylbut-2-yl, 2,2,2-trimethyleth-1-yl, n-hexyl, and the like.

"Alkenyl" refers to straight chain and branched hydrocarbon groups having one or more carbon-carbon double bonds, and generally having a specified number of carbon atoms. Examples of alkenyl groups include ethenyl, 1-propen-1-yl, 1-propen-2-yl, 2-propen-1-yl, 1-buten-1-yl, 1-buten-2-yl, 3-buten-1-yl, 3-buten-2-yl, 2-buten-1-yl, 2-buten-2-yl, 2-methyl-1-propen-1-yl, 2-methyl-2-propen-1-yl, 1,3-butadien-1-yl, 1,3-butadien-2-yl, and the like.

"Alkynyl" refers to straight chain or branched hydrocarbon groups having one or more triple carbon-carbon bonds, and generally having a specified number of carbon atoms.

Examples of alkynyl groups include ethynyl, 1-propyn-1-yl, 2-propyn-1-yl, 1-butyn-1-yl, 3-butyn-1-yl, 3-butyn-2-yl, 2-butyn-1-yl, and the like.

"Halo," "halogen" and "halogeno" may be used interchangeably and refer to fluoro, chloro, bromo, and iodo.

"Haloalkyl," "haloalkenyl," and "haloalkynyl," refer, respectively, to alkyl, alkenyl, and alkynyl groups substituted with one or more halogen atoms, where alkyl, alkenyl, and alkynyl are defined above, and generally having a specified number of carbon atoms. Examples of haloalkyl groups include fluoromethyl, difluoromethyl, trifluoromethyl, chloromethyl, dichloromethyl, trichloromethyl, and the like.

"Cycloalkyl" refers to saturated monocyclic and bicyclic hydrocarbon groups, generally having a specified number of carbon atoms that comprise the ring or rings (e.g., $C_{3-10}$ cycloalkyl refers to a cycloalkyl group having 3 to 10 carbon atoms as ring members). Bicyclic hydrocarbon groups may include spiro rings (two rings sharing one carbon atom), fused rings (two rings sharing two carbon atoms and the bond between the two common carbon atoms), and bridged rings (two rings sharing two carbon atoms, but not a common bond). The cycloalkyl group may be attached through any ring atom unless such attachment would violate valence requirements. In addition, the cycloalkyl group may include one or more non-hydrogen substituents unless such substitution would violate valence requirements.

Examples of monocyclic cycloalkyl groups include cyclopropyl, cyclobutyl, cyclopentyl, cyclohexyl, and the like. Examples of fused bicyclic cycloalkyl groups include bicyclo[2.1.0]pentanyl (i.e., bicyclo[2.1.0]pentan-1-yl, bicyclo[2.1.0]pentan-2-yl, and bicyclo[2.1.0]pentan-5-yl), bicyclo[3.1.0]hexanyl, bicyclo[3.2.0]heptanyl, bicyclo[4.1.0]heptanyl, bicyclo[3.3.0]octanyl, bicyclo[4.2.0]octanyl, bicyclo[4.3.0]nonanyl, bicyclo[4.4.0]decanyl, and the like. Examples of bridged cycloalkyl groups include bicyclo[2.1.1]hexanyl, bicyclo[2.2.1]heptanyl, bicyclo[3.1.1]heptanyl, bicyclo[2.2.2]octanyl, bicyclo[3.2.1]octanyl, bicyclo[4.1.1]octanyl, bicyclo[3.3.1]nonanyl, bicyclo[4.2.1]nonanyl, bicyclo[3.3.2]decanyl, bicyclo[4.2.2]decanyl, bicyclo[4.3.1]decanyl, bicyclo[3.3.3]undecanyl, bicyclo[4.3.2]undecanyl, bicyclo[4.3.3]dodecanyl, and the like. Examples of spiro cycloalkyl groups include spiro[3.3]heptanyl, spiro[2.4]heptanyl, spiro[3.4]octanyl, spiro[2.5]octanyl, spiro[3.5]nonanyl, and the like.

"Cycloalkylidene" refers to divalent monocyclic cycloalkyl groups, where cycloalkyl is defined above, which are attached through a single carbon atom of the group, and generally having a specified number of carbon atoms that comprise the ring (e.g., $C_{3-6}$ cycloalkylidene refers to a cycloalkylidene group having 3 to 6 carbon atoms as ring members). Examples include cyclopropylidene, cyclobutylidene, cyclopentylidene, and cyclohexylidene.

"Cycloalkenyl" refers to partially unsaturated monocyclic and bicyclic hydrocarbon groups, generally having a specified number of carbon atoms that comprise the ring or rings. As with cycloalkyl groups, the bicyclic cycloalkenyl groups may include spiro, fused, or bridged rings. Similarly, the cycloalkenyl group may be attached through any ring atom and may include one or more non-hydrogen substituents unless such attachment or substitution would violate valence requirements. Examples of cycloalkenyl groups include the partially unsaturated analogs of the cycloalkyl groups described above, such as cyclobutenyl (i.e., cyclobuten-1-yl and cyclobuten-3-yl), cyclopentenyl, cyclohexenyl, bicyclo[2.2.1]hept-2-enyl, and the like.

"Aryl" refers to fully unsaturated monocyclic aromatic hydrocarbons and to polycyclic hydrocarbons having at least one aromatic ring, both monocyclic and polycyclic aryl groups generally having a specified number of carbon atoms that comprise their ring members (e.g., $C_{6-14}$ aryl refers to an aryl group having 6 to 14 carbon atoms as ring members). The group may be attached through any ring atom and may include one or more non-hydrogen substituents unless such attachment or substitution would violate valence requirements. Examples of aryl groups include phenyl, cyclobutabenzenyl, indenyl, naphthalenyl, benzocycloheptanyl, biphenylenyl, fluorenyl, groups derived from cycloheptatriene cation, and the like.

"Arylene" refers to divalent aryl groups, where aryl is defined above. Examples of arylene groups include phenylene (i.e., benzene-1,2-diyl).

"Heterocycle" and "heterocyclyl" may be used interchangeably and refer to saturated or partially unsaturated monocyclic or bicyclic groups having ring atoms composed of carbon atoms and 1 to 4 heteroatoms independently selected from nitrogen, oxygen, and sulfur. Both the monocyclic and bicyclic groups generally have a specified number of carbon atoms in their ring or rings (e.g., $C_{2-6}$ heterocyclyl refers to a heterocyclyl group having 2 to 6 carbon atoms and 1 to 4 heteroatoms as ring members). As with bicyclic cycloalkyl groups, bicyclic heterocyclyl groups may include spiro rings, fused rings, and bridged rings. The heterocyclyl group may be attached through any ring atom and may include one or more non-hydrogen substituents unless such attachment or substitution would violate valence requirements or result in a chemically unstable compound. Examples of monocyclic heterocyclyl groups include oxiranyl, thiiranyl, aziridinyl (e.g., aziridin-1-yl and aziridin-2-yl), oxetanyl, thietanyl, azetidinyl, tetrahydrofuranyl, tetrahydrothiopheneyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thiazepanyl, 1,4-diazepanyl, 3,4-dihydro-2H-pyranyl, 3,6-dihydro-2H-pyranyl, 2H-pyranyl, 1,2-dihydropyridine, 1,2,3,4-tetrahydropyridinyl, and 1,2,5,6-tetrahydropyridinyl.

"Heterocycle-diyl" refers to heterocyclyl groups which are attached through two ring atoms of the group, where heterocyclyl is defined above. They generally have a specified number of carbon atoms in their ring or rings (e.g., $C_{2-6}$ heterocycle-diyl refers to a heterocycle-diyl group having 2 to 6 carbon atoms and 1 to 4 heteroatoms as ring members). Examples of heterocycle-diyl groups include the multivalent analogs of the heterocycle groups described above, such as morpholine-3,4-diyl, pyrrolidine-1,2-diyl, 1-pyrrolidinyl-2-ylidene, 1-pyridinyl-2-ylidene, 1-(4H)-pyrazolyl-5-ylidene, 1-(3H)-imidazolyl-2-ylidene, 3-oxazolyl-2-ylidene, 1-piperidinyl-2-ylidene, 1-piperazinyl-6-ylidene, and the like.

"Heteroaromatic" and "heteroaryl" may be used interchangeably and refer to unsaturated monocyclic aromatic groups and to polycyclic groups having at least one aromatic ring, each of the groups having ring atoms composed of carbon atoms and 1 to 4 heteroatoms independently selected from nitrogen, oxygen, and sulfur. Both the monocyclic and polycyclic groups generally have a specified number of carbon atoms as ring members (e.g., $C_{1-9}$ heteroaryl refers to a heteroaryl group having 1 to 9 carbon atoms and 1 to 4 heteroatoms as ring members) and may include any bicyclic group in which any of the above-listed monocyclic heterocycles are fused to a benzene ring. The heteroaryl group may be attached through any ring atom and may include one or more non-hydrogen substituents unless such attachment or substitution would violate valence requirements or result in a chemically unstable compound. Examples of heteroaryl groups include monocyclic groups such as pyrrolyl (e.g., pyrrol-1-yl, pyrrol-2-yl, and pyrrol-3-yl), furanyl, thiopheneyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, and pyrazinyl.

Examples of heteroaryl groups also include bicyclic groups such as benzofuranyl, isobenzofuranyl, benzothiopheneyl, benzo[c]thiopheneyl, indolyl, 3H-indolyl, isoindolyl, 1H-isoindolyl, indolinyl, isoindolinyl, benzimidazolyl, indazolyl, benzotriazolyl, 1H-pyrrolo[2,3-b]pyridinyl, 1H-pyrrolo[2,3-c]pyridinyl, 1H-pyrrolo[3,2-c]pyridinyl, 1H-pyrrolo[3,2-b]pyridinyl, 3H-imidazo[4,5-b]pyridinyl, 3H-imidazo[4,5-c]pyridinyl, 1H-pyrazolo[4,3-b]pyridinyl, 1H-pyrazolo[4,3-c]pyridinyl, 1H-pyrazolo[3,4-c]pyridinyl, 1H-pyrazolo[3,4-b]pyridinyl, 7H-purinyl, indolizinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, and pyrimido[4,5-d]pyrimidinyl.

"Heteroarylene" refers to heteroaryl groups which are attached through two ring atoms of the group, where heteroaryl is defined above. They generally have a specified number of carbon atoms in their ring or rings (e.g., $C_{3-5}$ heteroarylene refers to a heteroarylene group having 3 to 5 carbon atoms and 1 to 4 heteroatoms as ring members). Examples of heteroarylene groups include the multivalent analogs of the heteroaryl groups described above, such as pyridine-2,3-diyl, pyridine-3,4-diyl, pyrazole-4,5-diyl, pyrazole-3,4-diyl, and the like.

"Oxo" refers to a double bonded oxygen (=O).

"Leaving group" refers to any group that leaves a molecule during a fragmentation process, including substitution reactions, elimination reactions, and addition-elimination reactions. Leaving groups may be nucleofugal, in which the group leaves with a pair of electrons that formerly served as the bond between the leaving group and the molecule, or may be electrofugal, in which the group leaves without the pair of electrons. The ability of a nucleofugal leaving group to leave depends on its base strength, with the strongest bases being the poorest leaving groups. Common nucleofugal leaving groups include nitrogen (e.g., from diazonium salts); sulfonates, including alkylsulfonates (e.g., mesylate), fluoroalkylsulfonates (e.g., triflate, hexaflate, nonaflate, and tresylate), and arylsulfonates (e.g., tosylate, brosylate, closylate, and nosylate). Others include carbonates, halide ions, carboxylate anions, phenolate ions, and alkoxides. Some stronger bases, such as $NH_2^-$ and OFF can be made better leaving groups by treatment with an acid. Common electrofugal leaving groups include the proton, $CO_2$, and metals.

"Opposite enantiomer" refers to a molecule that is a non-superimposable mirror image of a reference molecule, which may be obtained by inverting all of the stereogenic centers of the reference molecule. For example, if the reference molecule has S absolute stereochemical configuration, then the opposite enantiomer has R absolute stereochemical configuration. Likewise, if the reference molecule has S,S absolute stereochemical configuration, then the opposite enantiomer has R,R stereochemical configuration, and so on.

"Stereoisomer" and "stereoisomers" of a compound with given stereochemical configuration refer to the opposite enantiomer of the compound and to any diastereoisomers, including geometrical isomers (Z/E) of the compound. For example, if a compound has S,R,Z stereochemical configuration, its stereoisomers would include its opposite enantiomer having R,S,Z configuration, and its diastereomers having S,S,Z configuration, R,R,Z configuration, S,R,E configuration, R,S,E configuration, S,S,E configuration, and R,R,E configuration. If the stereochemical configuration of a compound is not specified, then "stereoisomer" refers to any one of the possible stereochemical configurations of the compound.

"Substantially pure stereoisomer" and variants thereof refer to a sample containing a compound having a specific stereochemical configuration and which comprises at least about 95% of the sample.

"Pure stereoisomer" and variants thereof refer to a sample containing a compound having a specific stereochemical configuration and which comprises at least about 99.5% of the sample.

"Subject" refers to a mammal, including a human.

"Pharmaceutically acceptable" substances refer to those substances which are suitable for administration to subjects.

"Treating" refers to reversing, alleviating, inhibiting the progress of, or preventing a disease, disorder or condition to which such term applies, or to reversing, alleviating, inhibiting the progress of, or preventing one or more symptoms of such disorder, disease or condition.

"Treatment" refers to the act of "treating," as defined immediately above.

"Drug," "drug substance," "active pharmaceutical ingredient," and the like, refer to a compound (e.g., compounds of Formula 1, including subgeneric compounds and compounds specifically named in the specification) that may be used for treating a subject in need of treatment.

"Effective amount" of a drug, "therapeutically effective amount" of a drug, and the like, refer to the quantity of the drug that may be used for treating a subject and may depend on the weight and age of the subject and the route of administration, among other things.

"Excipient" refers to any diluent or vehicle for a drug.

"Pharmaceutical composition" refers to the combination of one or more drug substances and one or more excipients.

"Drug product," "pharmaceutical dosage form," "dosage form," "final dosage form" and the like, refer to a pharmaceutical composition suitable for treating a subject in need of treatment and generally may be in the form of tablets, capsules, sachets containing powder or granules, liquid solutions or suspensions, patches, films, and the like.

"Condition associated with BTK" and similar phrases relate to a disease, disorder or condition in a subject for which inhibition of BTK may provide a therapeutic or prophylactic benefit.

The following abbreviations are used throughout the specification: Ac (acetyl); ACN (acetonitrile); AIBN (azo-bis-isobutyronitrile); API (active pharmaceutical ingredient); aq (aqueous); Boc (tert-butoxycarbonyl); Cbz (carbobenzyloxy); dba (dibenzylideneacetone); DCC (1,3-dicyclohexylcarbodiimide); DCM (dichloromethane); DIPEA (N,N-diisopropylethylamine, Hünig's Base); DMA (N,N-dimethylacetamide); DMAP (4-dimethylaminopyridine); DMARD (disease modifying antirheumatic drug); DME (1,2-dimethoxyethane); DMF (N,N-dimethylformamide); DMSO (dimethylsulfoxide); DPPA (diphenylphosphoryl azide); dppf (1,1'-bis(diphenylphosphino)ferrocene); DTT (dithiothreitol); EDA ethoxylated dodecyl alcohol, Brj®35); EDC (N-(3-dimethylaminopropyl)-N'-ethylcarbodiimide); EDTA (ethylenediaminetetraacetic acid); ee (enantiomeric excess); eq (equivalents); Et (ethyl); Et$_3$N (triethyl-amine); EtOAc (ethyl acetate); EtOH (ethanol); 5-FAM (5-carboxyfluorescein); HATU (2-(3H-[1,2,3]triazolo[4,5-b]pyridin-3-yl)-1,1,3,3-tetramethyluronium hexafluorophosphate(V)); HEPES (4-(2-hydroxyethyl)piperazine-1-ethanesulfonic acid); HOAc (acetic acid); HOBt (1H-benzo[d][1,2,3]triazol-1-ol); IC$_{50}$ (concentration at 50% inhibition); IPA (isopropanol); IPAc (isopropyl acetate); IPE (isopropylether); LDA (lithium diisopropylamide); LiHMDS (lithium bis(trimethylsilyl)amide); mCPBA (m-chloroperoxybenzoic acid); Me (methyl); MeOH (methanol); MTBE (methyl tert-butyl ether); mp (melting point); NaOt-Bu (sodium tertiary butoxide); NMM (N-methylmorpholine); PE (petroleum ether); Ph (phenyl); pIC$_{50}$ (-log$_{10}$(IC$_{50}$), where IC$_{50}$ is given in molar (M) units); Pr (propyl); i-Pr (isopropyl); PTFE (polytetrafluoroethylene); RT (room temperature, approximately 20° C. to 25° C.); TCEP (tris(2-carboxyethyl)phosphine); TFA (trifluoroacetic acid); TFAA (2,2,2-trifluoroacetic anhydride); THF (tetrahydrofuran); TMS (trimethylsilyl); and Tris buffer (2-amino-2-hydroxymethyl-propane-1,3-diol buffer).

As described, below, this disclosure concerns compounds of Formula 1 and their pharmaceutically acceptable salts. This disclosure also concerns materials and methods for preparing compounds of Formula 1, pharmaceutical compositions which contain them, and the use of compounds of Formula 1 and their pharmaceutically acceptable salts (optionally in combination with other pharmacologically active agents) for treating Type I hypersensitivity reactions, autoimmune diseases, inflammatory disorders, cancer, non-malignant proliferative disorders, and other diseases, disorders or conditions associated with BTK.

In addition to the specific compounds in the examples, compounds of Formula 1 include those in which: (i) R$^2$ and R$^4$ are each independently selected from hydrogen, halo, methyl, and —OCH$_3$; (ii) R$^2$ and R$^4$ are each independently selected from hydrogen, halo, and methyl; (iii) R$^2$ and R$^4$ are each independently selected from hydrogen, fluoro, and methyl; (iv) R$^2$ is hydrogen and R$^4$ is methyl; or (v) R$^2$ and R$^4$ are each hydrogen.

In addition, or as an alternative, to one of embodiments (i) through (v) in the preceding paragraph, compounds of Formula 1 include those in which: (vi) R$^3$ is selected from hydrogen, halo, methyl, —OCH$_3$, and morpholino; (vii) R$^3$ is selected from hydrogen, halo, and methyl; (viii) R$^3$ is selected from hydrogen, fluoro, and methyl; or (ix) R$^3$ is hydrogen.

In addition, or as an alternative, to one or more of embodiments (i) through (ix) in the preceding paragraphs, compounds of Formula 1 include those in which: (x) R$^5$ is a bicyclic C$_{6-8}$ heteroaryl in which an aromatic ring is ortho-fused to a pyrrole, pyrazole, imidazole, triazole, pyrrolidine, pyrazolidine, imidazolidine or triazolidine ring, the aromatic ring is benzene or pyridine, and the bicyclic C$_{6-8}$ heteroaryl is optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xi) R$^5$ is selected from indazolyl, 1H-pyrazolo[4,3-b]pyridinyl, 1H-pyrazolo[3,4-b]pyridinyl, indolyl, isoindolyl, 1H-pyrrolo[3,2-b]pyridinyl, 1H-pyrrolo[2,3-b]pyridinyl, benzimidazolyl, benzotriazolyl, indolinyl, isoindolinyl, and benzimidazolinyl, each optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xii) R$^5$ is selected from 1H-indazol-5-yl, 1H-indazol-6-yl, 1H-pyrazolo[4,3-b]pyridin-5-yl, 1H-pyrazolo[4,3-b]pyridin-6-yl, 1H-pyrazolo[3,4-b]pyridin-5-yl, 1H-pyrazolo[3,4-b]pyridin-6-yl, 1H-indol-5-yl, 1H-indol-6-yl, 2H-isoindol-5-yl, 1H-pyrrolo[3,2-b]pyridin-5-yl, 1H-pyrrolo[3,2-b]pyridin-6-yl, 1H-pyrrolo[2,3-b]pyridin-5-yl, 1H-pyrrolo[2,3-b]pyridin-6-yl, 1H-benzo[d]imidazol-5-yl, 1H-benzo[d]imidazol-6-yl, 1H-benzo[d][1,2,3]triazol-5-yl, 1H-benzo[d][1,2,3]triazol-6-yl, indolin-5-yl, indolin-6-yl, isoindolin-5-yl, and 2,3-dihydro-1H-benzo[d]imidazol-5-yl, each optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xiii) R$^5$ is selected from 1H-indazol-5-yl, 1H-indazol-6-yl, 1H-indol-5-yl, 1H-indol-6-yl, 2H-isoindol-5-yl, 1H-benzo[d]imidazol-5-yl, 1H-benzo[d]imidazol-6-yl, 1H-benzo[d][1,2,3]triazol-5-yl, 1H-benzo[d][1,2,3]triazol-6-yl, and isoindolin-5-yl, each optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xiv) R$^5$ is a bicyclic C$_{6-8}$ heteroaryl having from two to four heteroatoms, each of the heteroatoms being nitrogen, and the bicyclic C$_{6-8}$ heteroaryl is optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xv) R$^5$ is selected from indazolyl, 1H-pyrazolo[4,3-b]pyridinyl, 1H-pyrazolo[3,4-b]pyridinyl, isoindolyl, 1H-pyrrolo[3,2-b]pyridinyl, 1H-pyrrolo[2,3-b]pyridinyl, benzimidazolyl, benzotriazolyl, indolinyl, isoindolinyl, and benzimidazolinyl, each optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xvi) R$^5$ is selected from 1H-indazol-5-yl, 1H-indazol-6-yl, 1H-pyrazolo[4,3-b]pyridin-5-yl, 1H-pyrazolo[4,3-b]pyridin-6-yl, 1H-pyrazolo[3,4-b]pyridin-5-yl, 1H-pyrazolo[3,4-b]pyridin-6-yl, 2H-isoindol-5-yl, 1H-pyrrolo[3,2-b]pyridin-5-yl, 1H-pyrrolo[3,2-b]pyridin-6-yl, 1H-pyrrolo[2,3-b]pyridin-5-yl, 1H-pyrrolo[2,3-b]pyridin-6-yl, 1H-benzo[d]imidazol-5-yl, 1H-benzo[d]imidazol-6-yl, 1H-benzo[d][1,2,3]triazol-5-yl, 1H-benzo[d][1,2,3]triazol-6-yl, indolin-5-yl, indolin-6-yl, isoindolin-5-yl, and 2,3-dihydro-1H-benzo[d]imidazol-5-yl, each optionally substituted with from one to four substituents independently selected from halo, oxo, —CN, R$^6$, and R$^7$.

In addition, or as an alternative, to one or more of embodiments (i) through (ix) in the preceding paragraphs, compounds of Formula 1 include those in which: (xvii) R$^5$ is selected from 1H-indazol-5-yl, 1H-indazol-6-yl, 2H-isoindol-5-yl, 1H-benzo[d]imidazol-5-yl, 1H-benzo[d]imidazol-6-yl, 1H-benzo[d][1,2,3]triazol-5-yl, 1H-benzo[d][1,2,3]triazol-6-yl, and isoindolin-5-yl, each optionally substituted with from one to four substituents independently selected from halo, oxo, —CN, $R^6$, and $R^7$.

In addition, or as an alternative, to one or more of embodiments (i) through (ix) in the preceding paragraphs, compounds of Formula 1 include those in which: (xviii) $R^5$ is selected from 1H-indazol-5-yl and 1H-indazol-6-yl, each optionally substituted with from one to four substituents independently selected from halo, oxo, —CN, $R^6$, and $R^7$.

In addition, or as an alternative, to one or more of embodiments (x) through (xviii) in the preceding paragraphs, compounds of Formula 1 include those in which: (xix) the $R^5$ substituent is optionally substituted with from one to three substituents independently selected from halo, oxo, —CN, $C_{1-4}$ alkyl, and —$OR^8$, wherein $R^8$ is selected from hydrogen and $C_{1-4}$ alkyl; (xx) the $R^5$ substituent is optionally substituted with from one to three substituents independently selected from fluoro, chloro, oxo, —CN, methyl, hydroxy, and methoxy; (xxi) the $R^5$ substituent is optionally substituted with fluoro, chloro, methyl, or methoxy; (xxii) the $R^5$ substituent is optionally substituted with methyl or methoxy; or (xxiii) the $R^5$ substituent is not optionally substituted (is unsubstituted).

In addition, or as an alternative, to one or more of embodiments (i) through (xxiii) in the preceding paragraphs, compounds of Formula 1 include those in which: (xxiv) each $R^7$, $R^8$, and $R^9$ substituent is optionally substituted with one or two substituents; or (xxv) each $R^7$, $R^8$, and $R^9$ substituent is unsubstituted (i.e., contains no optional substituents).

In addition, or as an alternative, to one or more of embodiments (i) through (xxiii) in the preceding paragraphs, compounds of Formula 1 include those in which: (xxvi) each $R^{11}$, $R^{12}$, and $R^{13}$ substituent is optionally substituted with one or two substituents; or (xxvii) each $R^{11}$, $R^{12}$, and $R^{13}$ substituent is unsubstituted.

In addition, or as an alternative, to one or more of embodiments (i) through (xxvii) in the preceding paragraphs, compounds of Formula 1 include those in which: (xxviii) each m is independently selected from 0, 1, 2, and 3; (xxix) each m is independently selected from 0, 1, and 2; (xxx) each m is independently selected from 0 and 1; or (xxxi) each m is 0.

Compounds of Formula 1 include embodiments (i) through (xxxi) described in the preceding paragraphs and all compounds specifically named above and in the examples, and may exist as salts, complexes, solvates, hydrates, and liquid crystals. Likewise, compounds of Formula 1 that are salts may exist as complexes, solvates, hydrates, and liquid crystals.

Compounds of Formula 1 may form pharmaceutically acceptable complexes, salts, solvates and hydrates. These salts include acid addition salts (including di-acids) and base salts. Pharmaceutically acceptable acid addition salts include salts derived from inorganic acids such as hydrochloric acid, nitric acid, phosphoric acid, sulfuric acid, hydrobromic acid, hydroiodic acid, hydrofluoric acid, and phosphorous acids, as well nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts include acetate, adipate, aspartate, benzoate, besylate, bicarbonate, carbonate, bisulfate, sulfate, borate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulfate, naphthylate, 2-napsylate, nicotinate, nitrate, orotate, oxalate, palmitate, pamoate, phosphate, hydrogen phosphate, dihydrogen phosphate, pyroglutamate, saccharate, stearate, succinate, tannate, tartrate, tosylate, trifluoroacetate and xinofoate salts.

Pharmaceutically acceptable base salts include salts derived from bases, including metal cations, such as an alkali or alkaline earth metal cation, as well as amines. Examples of suitable metal cations include sodium, potassium, magnesium, calcium, zinc, and aluminum. Examples of suitable amines include arginine, N,N'-dibenzylethylenediamine, chloroprocaine, choline, diethylamine, diethanolamine, dicyclohexylamine, ethylenediamine, glycine, lysine, N-methylglucamine, olamine, 2-amino-2-hydroxymethyl-propane-1, 3-diol, and procaine. For a discussion of useful acid addition and base salts, see S. M. Berge et al., *J. Pharm. Sci.* (1977) 66:1-19; see also Stahl and Wermuth, *Handbook of Pharmaceutical Salts: Properties, Selection, and Use* (2002).

Pharmaceutically acceptable salts may be prepared using various methods. For example, a compound of Formula 1 may be reacted with an appropriate acid or base to give the desired salt. Alternatively, a precursor of the compound of Formula 1 may be reacted with an acid or base to remove an acid- or base-labile protecting group or to open a lactone or lactam group of the precursor. Additionally, a salt of the compound of Formula 1 may be converted to another salt (or free form) through treatment with an appropriate acid or base or through contact with an ion exchange resin. Following reaction, the salt may be isolated by filtration if it precipitates from solution, or by evaporation to recover the salt. The degree of ionization of the salt may vary from completely ionized to almost non-ionized.

Compounds of Formula 1 may exist in a continuum of solid states ranging from fully amorphous to fully crystalline. The term "amorphous" refers to a state in which the material lacks long range order at the molecular level and, depending upon temperature, may exhibit the physical properties of a solid or a liquid. Typically such materials do not give distinctive X-ray diffraction patterns and, while exhibiting the properties of a solid, are more formally described as a liquid. Upon heating, a change from solid to liquid properties occurs which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

Compounds of Formula 1 may also exist in unsolvated and solvated forms. The term "solvate" describes a molecular complex comprising the compound and one or more pharmaceutically acceptable solvent molecules (e.g., ethanol). The term "hydrate" is a solvate in which the solvent is water. Pharmaceutically acceptable solvates include those in which the solvent may be isotopically substituted (e.g., $D_2O$, acetone-$d_6$, DMSO-$d_6$).

A currently accepted classification system for solvates and hydrates of organic compounds is one that distinguishes between isolated site, channel, and metal-ion coordinated solvates and hydrates. See, e.g., K. R. Morris (H. G. Brittain ed.) *Polymorphism in Pharmaceutical Solids* (1995). Isolated site solvates and hydrates are ones in which the solvent (e.g., water) molecules are isolated from direct contact with each other by intervening molecules of the organic compound. In channel solvates, the solvent molecules lie in lattice channels where they are next to other solvent molecules. In metal-ion coordinated solvates, the solvent molecules are bonded to the metal ion.

When the solvent or water is tightly bound, the complex will have a well-defined stoichiometry independent of humidity. When, however, the solvent or water is weakly bound, as in channel solvates and in hygroscopic compounds, the water or solvent content will depend on humidity and drying conditions. In such cases, non-stoichiometry will typically be observed.

Compounds of Formula 1 may also exist as multi-component complexes (other than salts and solvates) in which the compound (drug) and at least one other component are present in stoichiometric or non-stoichiometric amounts. Complexes of this type include clathrates (drug-host inclusion complexes) and co-crystals. The latter are typically defined as crystalline complexes of neutral molecular constituents which are bound together through non-covalent interactions, but could also be a complex of a neutral molecule with a salt. Co-crystals may be prepared by melt crystallization, by recrystallization from solvents, or by physically grinding the components together. See, e.g., O. Almarsson and M. J. Zaworotko, *Chem. Commun.* (2004) 17:1889-1896. For a general review of multi-component complexes, see J. K. Haleblian, *J. Pharm. Sci.* (1975) 64(8): 1269-88.

When subjected to suitable conditions, compounds of Formula 1 may exist in a mesomorphic state (mesophase or liquid crystal). The mesomorphic state lies between the true crystalline state and the true liquid state (either melt or solution). Mesomorphism arising as the result of a change in temperature is described as "thermotropic" and mesomorphism resulting from the addition of a second component, such as water or another solvent, is described as "lyotropic." Compounds that have the potential to form lyotropic mesophases are described as "amphiphilic" and include molecules which possess a polar ionic moiety (e.g., —$COO^-Na^+$, —$COO^-K^+$, —$SO_3^-Na^+$) or polar non-ionic moiety (such as —$N^-N^+$ $(CH_3)_3$). See, e.g., N. H. Hartshorne and A. Stuart, *Crystals and the Polarizing Microscope* (4th ed, 1970).

Each compound of Formula 1 may exist as polymorphs, stereoisomers, tautomers, or some combination thereof, may be isotopically-labeled, may result from the administration of a prodrug, or form a metabolite following administration.

"Prodrugs" refer to compounds having little or no pharmacological activity that can, when metabolized in vivo, undergo conversion to compounds having desired pharmacological activity. Prodrugs may be prepared by replacing appropriate functionalities present in pharmacologically active compounds with "pro-moieties" as described, for example, in H. Bundgaar, *Design of Prodrugs* (1985). Examples of prodrugs include ester, ether or amide derivatives of compounds of Formula 1 having carboxylic acid, hydroxy, or amino functional groups, respectively. For further discussions of prodrugs, see e.g., T. Higuchi and V. Stella "Pro-drugs as Novel Delivery Systems," *ACS Symposium Series* 14 (1975) and E. B. Roche ed., *Bioreversible Carriers in Drug Design* (1987).

"Metabolites" refer to compounds formed in vivo upon administration of pharmacologically active compounds. Examples include hydroxymethyl, hydroxy, secondary amino, primary amino, phenol, and carboxylic acid derivatives of compounds of Formula 1 having methyl, alkoxy, tertiary amino, secondary amino, phenyl, and amide groups, respectively.

Compounds of Formula 1 may exist as stereoisomers that result from the presence of one or more stereogenic centers, one or more double bonds, or both. The stereoisomers may be pure, substantially pure, or mixtures. Such stereoisomers may also result from acid addition or base salts in which the counter-ion is optically active, for example, when the counter-ion is D-lactate or L-lysine.

Compounds of Formula 1 may exist as tautomers, which are isomers resulting from tautomerization. Tautomeric isomerism includes, for example, imine-enamine, keto-enol, oxime-nitroso, and amide-imidic acid tautomerism.

Compounds of Formula 1 may exhibit more than one type of isomerism.

Geometrical (cis/trans) isomers may be separated by conventional techniques such as chromatography and fractional crystallization.

Conventional techniques for preparing or isolating a compound having a specific stereochemical configuration include chiral synthesis from a suitable optically pure precursor or resolution of the racemate (or the racemate of a salt or derivative) using, for example, chiral high pressure liquid chromatography (HPLC). Alternatively, the racemate (or a racemic precursor) may be reacted with a suitable optically active compound, for example, an alcohol, or, in the case where the compound of Formula 1 contains an acidic or basic moiety, an acid or base such as tartaric acid or 1-phenylethylamine. The resulting diastereomeric mixture may be separated by chromatography, fractional crystallization, etc., and the appropriate diastereoisomer converted to the compound having the requisite stereochemical configuration. For a further discussion of techniques for separating stereoisomers, see E. L. Eliel and S. H. Wilen, *Stereochemistry of Organic Compounds* (1994).

Compounds of Formula 1 may possess isotopic variations, in which at least one atom is replaced by an atom having the same atomic number, but an atomic mass different from the atomic mass usually found in nature. Isotopes suitable for inclusion in compounds of Formula 1 include, for example, isotopes of hydrogen, such as $^2H$ and $^3H$; isotopes of carbon, such as $^{11}C$, $^{13}C$ and $^{14}C$; isotopes of nitrogen, such as $^{13}N$ and $^{15}N$; isotopes of oxygen, such as $^{15}O$, $^{17}O$ and $^{18}O$; isotopes of sulfur, such as $^{35}S$; isotopes of fluorine, such as $^{18}F$; isotopes of chlorine, such as $^{36}Cl$, and isotopes of iodine, such as $^{123}I$ and $^{125}I$. Use of isotopic variations (e.g., deuterium, $^2H$) may afford certain therapeutic advantages resulting from greater metabolic stability, for example, increased in vivo half-life or reduced dosage requirements. Additionally, certain isotopic variations of the disclosed compounds may incorporate a radioactive isotope (e.g., tritium, $^3H$, or $^{14}C$), which may be useful in drug and/or substrate tissue distribution studies. Substitution with positron emitting isotopes, such as $^{11}C$, $^{18}F$, $^{15}O$, and $^{13}N$, may be useful in Positron Emission Topography (PET) studies for examining substrate receptor occupancy. Isotopically-labeled compounds may be prepared by processes analogous to those described elsewhere in the disclosure using an appropriate isotopically-labeled reagent in place of a non-labeled reagent.

The compounds of Formula 1 may be prepared using the techniques described below. Some of the schemes and examples may omit details of common reactions, including oxidations, reductions, and so on, separation techniques (extraction, evaporation, precipitation, chromatography, filtration, trituration, crystallization, and the like), and analytical procedures, which are known to persons of ordinary skill in the art of organic chemistry. The details of such reactions and techniques can be found in a number of treatises, including Richard Larock, *Comprehensive Organic Transformations* (1999), and the multi-volume series edited by Michael B. Smith and others, *Compendium of Organic Synthetic Methods* (1974 et seq.). Starting materials and reagents may be obtained from commercial sources or may be prepared using literature methods. Some of the reaction schemes may omit minor products resulting from chemical transformations (e.g., an alcohol from the hydrolysis of an ester, $CO_2$ from the decarboxylation of a di-acid, etc.). In addition, in some instances, reaction intermediates may be used in subsequent steps without isolation or purification (i.e., in situ).

In some of the reaction schemes and examples below, certain compounds may be prepared using protecting groups, which prevent undesirable chemical reaction at otherwise reactive sites. Protecting groups may also be used to enhance solubility or otherwise modify physical properties of a compound. For a discussion of protecting group strategies, a description of materials and methods for installing and removing protecting groups, and a compilation of useful protecting groups for common functional groups, including amines, carboxylic acids, alcohols, ketones, aldehydes, and so on, see T. W. Greene and P. G. Wuts, *Protecting Groups in Organic Chemistry* (1999) and P. Kocienski, *Protective Groups* (2000).

Generally, the chemical transformations described throughout the specification may be carried out using substantially stoichiometric amounts of reactants, though certain reactions may benefit from using an excess of one or more of the reactants. Additionally, many of the reactions disclosed throughout the specification may be carried out at about room temperature (RT) and ambient pressure, but depending on reaction kinetics, yields, and so on, some reactions may be run at elevated pressures or employ higher temperatures (e.g., reflux conditions) or lower temperatures (e.g., −78° C. to 0° C.). Any reference in the disclosure to a stoichiometric range, a temperature range, a pH range, etc., whether or not expressly using the word "range," also includes the indicated endpoints.

Many of the chemical transformations may also employ one or more compatible solvents, which may influence the reaction rate and yield. Depending on the nature of the reactants, the one or more solvents may be polar protic solvents (including water), polar aprotic solvents, non-polar solvents, or some combination. Representative solvents include saturated aliphatic hydrocarbons (e.g., n-pentane, n-hexane, n-heptane, n-octane); aromatic hydrocarbons (e.g., benzene, toluene, xylenes); halogenated hydrocarbons (e.g., methylene chloride, chloroform, carbon tetrachloride); aliphatic alcohols (e.g., methanol, ethanol, propan-1-ol, propan-2-ol, butan-1-ol, 2-methyl-propan-1-ol, butan-2-ol, 2-methyl-propan-2-ol, pentan-1-ol, 3-methyl-butan-1-ol, hexan-1-ol, 2-methoxy-ethanol, 2-ethoxy-ethanol, 2-butoxy-ethanol, 2-(2-methoxy-ethoxy)-ethanol, 2-(2-ethoxy-ethoxy)-ethanol, 2-(2-butoxy-ethoxy)-ethanol); ethers (e.g., diethyl ether, di-isopropyl ether, dibutyl ether, 1,2-dimethoxy-ethane, 1,2-diethoxy-ethane, 1-methoxy-2-(2-methoxy-ethoxy)-ethane, 1-ethoxy-2-(2-ethoxy-ethoxy)-ethane, tetrahydrofuran, 1,4-dioxane); ketones (e.g., acetone, methyl ethyl ketone); esters (methyl acetate, ethyl acetate); nitrogen-containing solvents (e.g., formamide, N,N-dimethylformamide, acetonitrile, N-methyl-pyrrolidone, pyridine, quinoline, nitrobenzene); sulfur-containing solvents (e.g., carbon disulfide, dimethyl sulfoxide, tetrahydro-thiophene-1,1,-dioxide); and phosphorus-containing solvents (e.g., hexamethylphosphoric triamide).

In the schemes, below, substituent identifiers (e.g., $R^1$, $R^2$, $R^3$, etc.) are as defined above for Formula 1. As mentioned earlier, however, some of the starting materials and intermediates may include protecting groups, which are removed prior to the final product. In such cases, the substituent identifier refers to moieties defined in Formula 1 and to those moieties with appropriate protecting groups. For example, a starting material or intermediate in the schemes may include a substituent identifier that is a moiety having a potentially reactive amine. In such cases, the substituent identifier would include the moiety with or without, say, a Boc or Cbz group attached to the amine.

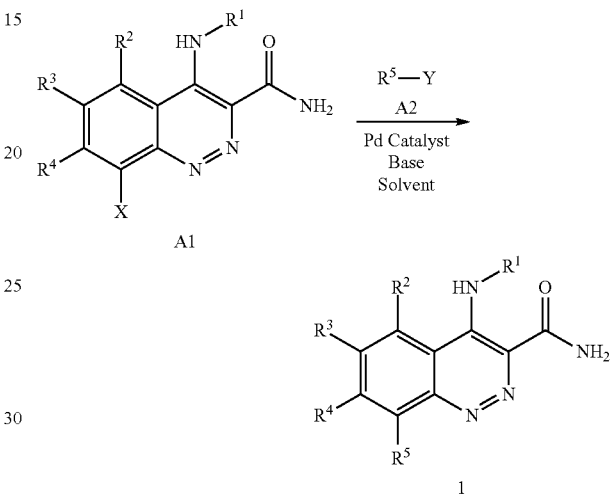

Scheme A

Scheme A shows a general method for preparing compounds of Formula 1 by reacting a cinnoline halide or pseudohalide (A1) with a boronic acid or ester (A2) under Suzuki conditions. As shown in Scheme A, the cinnoline halide or pseudohalide (A1, e.g. X is Br, Cl, I, or triflate) may be reacted with a boronic acid or ester (A2 e.g. Y is —B(OR')$_2$, where each R' is H or $C_{1-4}$ alkyl or each R' together forms a $C_{1-8}$ alkanediyl such as 2,3-dimethylbutan-2,3-diyl) in the presence of a palladium catalyst (e.g., Pd(PPh$_3$)$_4$, (PPh$_3$)$_2$PdCl$_2$, PdCl$_2$(dppf), etc.), a base (e.g., KF, Na$_2$CO$_3$, NaHCO$_3$, Cs$_2$CO$_3$), and one or more solvents (e.g., dioxane, DCM, DMF, H$_2$O, etc.) at elevated temperature (e.g., 90-145° C.). The method depicted in Scheme A may be varied as desired. For example, the halide or pseudohalide (A1) may be reacted with the boronic acid or boronate ester (A2) and the resulting intermediate (not shown) further elaborated via, for example, alkylation, acylation, hydrolysis, oxidation, reduction, amidation, sulfonation, alkynation, alkyenation, and the like, to give the compound of Formula 1.

Scheme B shows a general method for preparing the cinnoline halide or pseudohalide (A1) depicted in Scheme A. According to the method, aniline derivative B1 undergoes diazotization via reaction with aqueous sodium nitrite and hydrochloric acid at reduced temperature (5° C. or less). The resulting diazonium salt B2 (in solution) is reacted with 2-cyanoacetamide in the presence of aqueous sodium acetate at reduced temperature (about 10° C. or less). Heating the resulting azo intermediate B3 with a Lewis acid (e.g., AlCl$_3$) at elevated temperature (e.g., 100-115° C.) in a suitable solvent (e.g., chlorobenzene, toluene, etc.) gives, following treatment with hydrochloric acid at elevated temperature (e.g., 90-110° C.), the compound of formula A1.

Scheme B

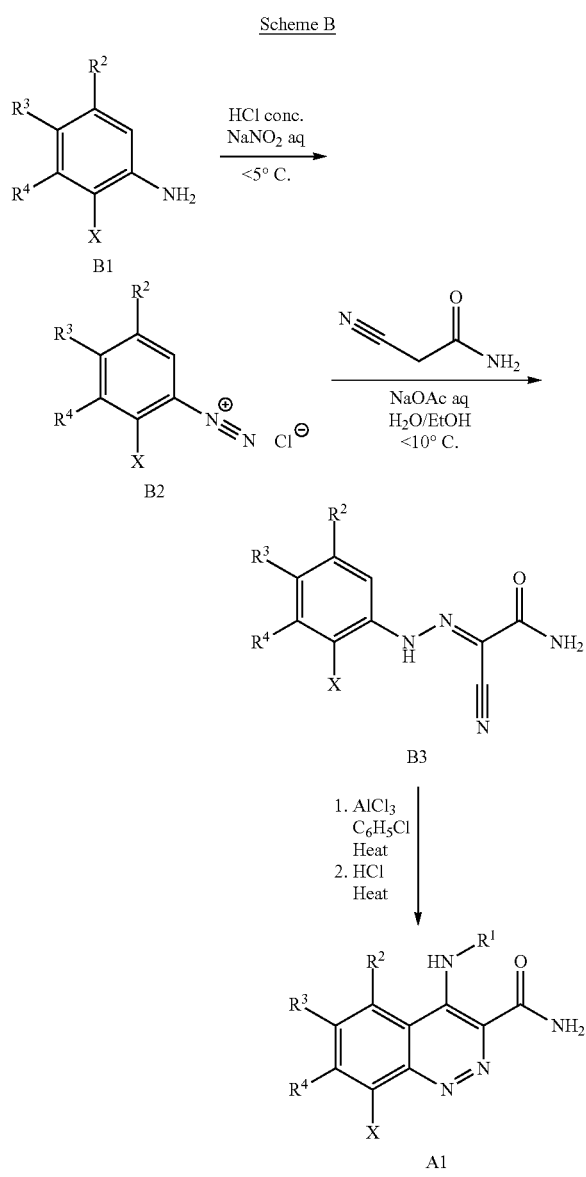

Compounds of Formula 1, which include compounds named above, and their pharmaceutically acceptable complexes, salts, solvates and hydrates, should be assessed for their biopharmaceutical properties, such as solubility and solution stability across pH, permeability, and the like, to select an appropriate dosage form and route of administration. Compounds that are intended for pharmaceutical use may be administered as crystalline or amorphous products, and may be obtained, for example, as solid plugs, powders, or films by methods such as precipitation, crystallization, freeze drying, spray drying, evaporative drying, microwave drying, or radio frequency drying.

Compounds of Formula 1 may be administered alone or in combination with one another or with one or more pharmacologically active compounds which are different than the compounds of Formula 1. Generally, one or more these compounds are administered as a pharmaceutical composition (a formulation) in association with one or more pharmaceutically acceptable excipients. The choice of excipients depends on the particular mode of administration, the effect of the excipient on solubility and stability, and the nature of the dosage form, among other things. Useful pharmaceutical compositions and methods for their preparation may be found, for example, in A. R. Gennaro (ed.), *Remington: The Science and Practice of Pharmacy* (20th ed., 2000).

Compounds of Formula 1 may be administered orally. Oral administration may involve swallowing in which case the compound enters the bloodstream via the gastrointestinal tract. Alternatively or additionally, oral administration may involve mucosal administration (e.g., buccal, sublingual, supralingual administration) such that the compound enters the bloodstream through the oral mucosa.

Formulations suitable for oral administration include solid, semi-solid and liquid systems such as tablets; soft or hard capsules containing multi- or nano-particulates, liquids, or powders; lozenges which may be liquid-filled; chews; gels; fast dispersing dosage forms; films; ovules; sprays; and buccal or mucoadhesive patches. Liquid formulations include suspensions, solutions, syrups and elixirs. Such formulations may be employed as fillers in soft or hard capsules (made, e.g., from gelatin or hydroxypropylmethylcellulose) and typically comprise a carrier (e.g., water, ethanol, polyethylene glycol, propylene glycol, methylcellulose, or a suitable oil) and one or more emulsifying agents, suspending agents or both. Liquid formulations may also be prepared by the reconstitution of a solid (e.g., from a sachet).

Compounds of Formula 1 may also be used in fast-dissolving, fast-disintegrating dosage forms such as those described in Liang and Chen, *Expert Opinion in Therapeutic Patents* (2001) 11(6):981-986.

For tablet dosage forms, depending on dose, the active pharmaceutical ingredient (API) may comprise from about 1 wt % to about 80 wt % of the dosage form or more typically from about 5 wt % to about 60 wt % of the dosage form. In addition to the API, tablets may include one or more disintegrants, binders, diluents, surfactants, glidants, lubricants, anti-oxidants, colorants, flavoring agents, preservatives, and taste-masking agents. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, $C_{1-6}$ alkyl-substituted hydroxypropylcellulose, starch, pregelatinized starch, and sodium alginate. Generally, the disintegrant will comprise from about 1 wt % to about 25 wt % or from about 5 wt % to about 20 wt % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinized starch, hydroxypropylcellulose and hydroxypropylmethylcellulose. Tablets may also contain diluents, such as lactose (monohydrate, spray-dried monohydrate, anhydrous), mannitol, xylitol, dextrose, sucrose, sorbitol, microcrystalline cellulose, starch and dibasic calcium phosphate dihydrate.

Tablets may also include surface active agents, such as sodium lauryl sulfate and polysorbate 80, and glidants such as silicon dioxide and talc. When present, surface active agents may comprise from about 0.2 wt % to about 5 wt % of the tablet, and glidants may comprise from about 0.2 wt % to about 1 wt % of the tablet.

Tablets may also contain lubricants such as magnesium stearate, calcium stearate, zinc stearate, sodium stearyl fumarate, and mixtures of magnesium stearate with sodium lauryl sulfate. Lubricants may comprise from about 0.25 wt % to about 10 wt % or from about 0.5 wt % to about 3 wt % of the tablet.

Tablet blends may be compressed directly or by roller compaction to form tablets. Tablet blends or portions of blends may alternatively be wet-, dry-, or melt-granulated, melt congealed, or extruded before tableting. If desired, prior to blending one or more of the components may be sized by screening or milling or both. The final dosage form may comprise one or more layers and may be coated, uncoated, or encapsulated. Exemplary tablets may contain up to about 80 wt % of API, from about 10 wt % to about 90 wt % of binder, from about 0 wt % to about 85 wt % of diluent, from about 2 wt % to about 10 wt % of disintegrant, and from about 0.25 wt % to about 10 wt % of lubricant. For a discussion of blending, granulation, milling, screening, tableting, coating, as well as a description of alternative techniques for preparing drug products, see A. R. Gennaro (ed.), *Remington: The Science and Practice of Pharmacy* (20th ed., 2000); H. A. Lieberman et al. (ed.), *Pharmaceutical Dosage Forms: Tablets*, Vol. 1-3 (2d ed., 1990); and D. K. Parikh & C. K. Parikh, *Handbook of Pharmaceutical Granulation Technology*, Vol. 81 (1997).

Consumable oral films for human or veterinary use are pliable water-soluble or water-swellable thin film dosage forms which may be rapidly dissolving or mucoadhesive. In addition to the API, a typical film includes one or more film-forming polymers, binders, solvents, humectants, plasticizers, stabilizers or emulsifiers, viscosity-modifying agents, and solvents. Other film ingredients may include antioxidants, colorants, flavorants and flavor enhancers, preservatives, salivary stimulating agents, cooling agents, co-solvents (including oils), emollients, bulking agents, antifoaming agents, surfactants, and taste-masking agents. Some components of the formulation may perform more than one function.

In addition to dosing requirements, the amount of API in the film may depend on its solubility. If water soluble, the API would typically comprise from about 1 wt % to about 80 wt % of the non-solvent components (solutes) in the film or from about 20 wt % to about 50 wt % of the solutes in the film. A less soluble API may comprise a greater proportion of the composition, typically up to about 88 wt % of the non-solvent components in the film.

The film-forming polymer may be selected from natural polysaccharides, proteins, or synthetic hydrocolloids and typically comprises from about 0.01 wt % to about 99 wt % or from about 30 wt % to about 80 wt % of the film.

Film dosage forms are typically prepared by evaporative drying of thin aqueous films coated onto a peelable backing support or paper, which may carried out in a drying oven or tunnel (e.g., in a combined coating-drying apparatus), in lyophilization equipment, or in a vacuum oven.

Useful solid formulations for oral administration may include immediate release formulations and modified release formulations. Modified release formulations include delayed-, sustained-, pulsed-, controlled-, targeted-, and programmed-release. For a general description of suitable modified release formulations, see U.S. Pat. No. 6,106,864. For details of other useful release technologies, such as high energy dispersions and osmotic and coated particles, see Verma et al, *Pharmaceutical Technology On-line* (2001) 25(2):1-14.

Compounds of Formula 1 may also be administered directly into the blood stream, muscle, or an internal organ of the subject. Suitable techniques for parenteral administration include intravenous, intraarterial, intraperitoneal, intrathecal, intraventricular, intraurethral, intrasternal, intracranial, intramuscular, intrasynovial, and subcutaneous administration. Suitable devices for parenteral administration include needle injectors, including microneedle injectors, needle-free injectors, and infusion devices.

Parenteral formulations are typically aqueous solutions which may contain excipients such as salts, carbohydrates and buffering agents (e.g., pH of from about 3 to about 9). For some applications, however, compounds of Formula 1 may be more suitably formulated as a sterile non-aqueous solution or as a dried form to be used in conjunction with a suitable vehicle such as sterile, pyrogen-free water. The preparation of parenteral formulations under sterile conditions (e.g., by lyophilization) may be readily accomplished using standard pharmaceutical techniques.

The solubility of compounds which are used in the preparation of parenteral solutions may be increased through appropriate formulation techniques, such as the incorporation of solubility-enhancing agents. Formulations for parenteral administration may be formulated to be immediate or modified release. Modified release formulations include delayed, sustained, pulsed, controlled, targeted, and programmed release. Thus, compounds of Formula 1 may be formulated as a suspension, a solid, a semi-solid, or a thixotropic liquid for administration as an implanted depot providing modified release of the active compound. Examples of such formulations include drug-coated stents and semi-solids and suspensions comprising drug-loaded poly(DL-lactic-coglycolic) acid (PGLA) microspheres.

Compounds of Formula 1 may also be administered topically, intradermally, or transdermally to the skin or mucosa. Typical formulations for this purpose include gels, hydrogels, lotions, solutions, creams, ointments, dusting powders, dressings, foams, films, skin patches, wafers, implants, sponges, fibers, bandages and microemulsions. Liposomes may also be used. Typical carriers may include alcohol, water, mineral oil, liquid petrolatum, white petrolatum, glycerin, polyethylene glycol and propylene glycol. Topical formulations may also include penetration enhancers. See, e.g., Finnin and Morgan, *J. Pharm. Sci.* 88(10):955-958 (1999).

Other means of topical administration include delivery by electroporation, iontophoresis, phonophoresis, sonophoresis and microneedle or needle-free (e.g. Powderject™ and Bioject™) injection. Formulations for topical administration may be formulated to be immediate or modified release as described above.

Compounds of Formula 1 may also be administered intranasally or by inhalation, typically in the form of a dry powder, an aerosol spray, or nasal drops. An inhaler may be used to administer the dry powder, which comprises the API alone, a powder blend of the API and a diluent, such as lactose, or a mixed component particle that includes the API and a phospholipid, such as phosphatidylcholine. For intranasal use, the powder may include a bioadhesive agent, e.g., chitosan or cyclodextrin. A pressurized container, pump, sprayer, atomizer, or nebulizer, may be used to generate the aerosol spray from a solution or suspension comprising the API, one or more agents for dispersing, solubilizing, or extending the release of the API (e.g., EtOH with or without water), one or more solvents (e.g., 1,1,1,2-tetrafluoroethane or 1,1,1,2,3,3, 3-heptafluoropropane) which serve as a propellant, and an optional surfactant, such as sorbitan trioleate, oleic acid, or an oligolactic acid. An atomizer using electrohydrodynamics may be used to produce a fine mist.

Prior to use in a dry powder or suspension formulation, the drug product is usually comminuted to a particle size suitable for delivery by inhalation (typically 90% of the particles, based on volume, having a largest dimension less than 5 microns). This may be achieved by any appropriate size reduction method, such as spiral jet milling, fluid bed jet milling, supercritical fluid processing, high pressure homogenization, or spray drying.

Capsules, blisters and cartridges (made, for example, from gelatin or hydroxypropylmethyl cellulose) for use in an inhaler or insufflator may be formulated to contain a powder mixture of the active compound, a suitable powder base such as lactose or starch, and a performance modifier such as L-leucine, mannitol, or magnesium stearate. The lactose may be anhydrous or monohydrated. Other suitable excipients include dextran, glucose, maltose, sorbitol, xylitol, fructose, sucrose, and trehalose.

A suitable solution formulation for use in an atomizer using electrohydrodynamics to produce a fine mist may contain from about 1 µg to about 20 mg of the API per actuation and the actuation volume may vary from about 1 µL to about 100 µL. A typical formulation may comprise one or more compounds of Formula 1, propylene glycol, sterile water, EtOH, and NaCl. Alternative solvents, which may be used instead of propylene glycol, include glycerol and polyethylene glycol.

Formulations for inhaled administration, intranasal administration, or both, may be formulated to be immediate or modified release using, for example, PGLA. Suitable flavors, such as menthol and levomenthol, or sweeteners, such as saccharin or sodium saccharin, may be added to formulations intended for inhaled/intranasal administration.

In the case of dry powder inhalers and aerosols, the dosage unit is determined by means of a valve that delivers a metered amount. Units are typically arranged to administer a metered dose or "puff" containing from about 10 µg to about 1000 µg of the API. The overall daily dose will typically range from about 100 µg to about 10 mg which may be administered in a single dose or, more usually, as divided doses throughout the day.

The active compounds may be administered rectally or vaginally, e.g., in the form of a suppository, pessary, or enema. Cocoa butter is a traditional suppository base, but various alternatives may be used as appropriate. Formulations for rectal or vaginal administration may be formulated to be immediate or modified release as described above.

Compounds of Formula 1 may also be administered directly to the eye or ear, typically in the form of drops of a micronized suspension or solution in isotonic, pH-adjusted, sterile saline. Other formulations suitable for ocular and aural administration include ointments, gels, biodegradable implants (e.g. absorbable gel sponges, collagen), non-biodegradable implants (e.g. silicone), wafers, lenses, and particulate or vesicular systems, such as niosomes or liposomes. The formulation may include one or more polymers and a preservative, such as benzalkonium chloride. Typical polymers include crossed-linked polyacrylic acid, polyvinylalcohol, hyaluronic acid, cellulosic polymers (e.g., hydroxypropylmethylcellulose, hydroxyethylcellulose, methyl cellulose), and heteropolysaccharide polymers (e.g., gelan gum). Such formulations may also be delivered by iontophoresis. Formulations for ocular or aural administration may be formulated to be immediate or modified release as described above.

To improve their solubility, dissolution rate, taste-masking, bioavailability, or stability, compounds of Formula 1 may be combined with soluble macromolecular entities, including cyclodextrin and its derivatives and polyethylene glycol-containing polymers. For example, API-cyclodextrin complexes are generally useful for most dosage forms and routes of administration. Both inclusion and non-inclusion complexes may be used. As an alternative to direct complexation with the API, the cyclodextrin may be used as an auxiliary additive, i.e. as a carrier, diluent, or solubilizer. Alpha-, beta- and gamma-cyclodextrins are commonly used for these purposes. See, e.g., WO 91/11172, WO 94/02518, and WO 98/55148.

As noted above, one or more compounds of Formula 1, including compounds specifically named in the examples, and their pharmaceutically active complexes, salts, solvates and hydrates, may be combined with each other or with one or more other active pharmaceutically active compounds to treat various diseases, disorders or conditions. In such cases, the active compounds may be combined in a single dosage form as described above or may be provided in the form of a kit which is suitable for coadministration of the compositions. The kit comprises (1) two or more different pharmaceutical compositions, at least one of which contains a compound of Formula 1; and (2) a device for separately retaining the two pharmaceutical compositions, such as a divided bottle or a divided foil packet. An example of such a kit is the familiar blister pack used for the packaging of tablets or capsules. The kit is suitable for administering different types of dosage forms (e.g., oral and parenteral) or for administering different pharmaceutical compositions at separate dosing intervals, or for titrating the different pharmaceutical compositions against one another. To assist with patient compliance, the kit typically comprises directions for administration and may be provided with a memory aid.

For administration to human patients, the total daily dose of the claimed and disclosed compounds is typically in the range of about 0.1 mg to about 3000 mg depending on the route of administration. For example, oral administration may require a total daily dose of from about 1 mg to about 3000 mg, while an intravenous dose may only require a total daily dose of from about 0.1 mg to about 300 mg. The total daily dose may be administered in single or divided doses and, at the physician's discretion, may fall outside of the typical ranges given above. Although these dosages are based on an average human subject having a mass of about 60 kg to about 70 kg, the physician will be able to determine the appropriate dose for a patient (e.g., an infant) whose mass falls outside of this weight range.

As noted above, the compounds of Formula 1 may be used to treat diseases, disorders or conditions for which inhibition of BTK is indicated. Such diseases, disorders or conditions generally relate to any unhealthy or abnormal state in a subject for which the inhibition of BTK provides a therapeutic benefit. More particularly, such diseases, disorders or conditions may involve the immune system and inflammation, including Type I hypersensitivity (allergic) reactions (allergic rhinitis, allergic asthma, and atopic dermatitis); autoimmune diseases (rheumatoid arthritis, multiple sclerosis, systemic lupus erythematosus, psoriasis, immune thrombocytopenic purpura, Sjögren's syndrome, ankylosing spondylitis, and Behcet's disease); inflammatory bowel disease; inflammation of the lung (chronic obstructive pulmonary disease), atherosclerosis, thrombosis, and myocardial infarction. The compounds of Formula 1 may also be used to treat diseases, disorders or conditions related to abnormal cell growth, including hematological malignancies, such as acute myeloid leukemia, B-cell chronic lymphocytic leukemia, B-cell lymphoma (e.g., mantle cell lymphoma), T-cell lymphoma (e.g., peripheral T-cell lymphoma), and multiple myeloma, as well as epithelial cancers (i.e., carcinomas), such as lung cancer (small cell lung cancer and non-small cell lung cancer), pancreatic cancer, and colon cancer.

In addition to the hematological malignancies and epithelial cancers noted above, the compounds of Formula 1 may also be used to treat other types of cancer, including leukemia (chronic myelogenous leukemia and chronic lymphocytic leukemia); breast cancer, genitourinary cancer, skin cancer, bone cancer, prostate cancer, and liver cancer; brain cancer; cancer of the larynx, gall bladder, rectum, parathyroid, thyroid, adrenal, neural tissue, bladder, head, neck, stomach, bronchi, and kidneys; basal cell carcinoma, squamous cell carcinoma, metastatic skin carcinoma, osteosarcoma, Ewing's sarcoma, veticulum cell sarcoma, and Kaposi's sarcoma; myeloma, giant cell tumor, islet cell tumor, acute and chronic lymphocytic and granulocytic tumors, hairy-cell tumor, adenoma, medullary carcinoma, pheochromocytoma, mucosal neuromas, intestinal ganglioneuromas, hyperplastic corneal nerve tumor, marfanoid habitus tumor, Wilms' tumor, seminoma, ovarian tumor, leiomyomater tumor, cervical dysplasia, neuroblastoma, retinoblastoma, myelodysplastic syndrome, rhabdomyosarcoma, astrocytoma, non-Hodgkin's lymphoma, malignant hypercalcemia, polycythermia vera, adenocarcinoma, glioblastoma multiforma, glioma, lymphomas, and malignant melanomas, among others.

In addition to cancer, the compounds of Formula 1 may also be used to treat other diseases, disorders or conditions related to abnormal cell growth, including non-malignant proliferative diseases such as benign prostatic hypertrophy, restinosis, hyperplasia, synovial proliferation disorder, idiopathic plasmacytic lymphadenopathy, retinopathy or other neovascular disorders of the eye, among others.

The compounds of Formula 1 may also be used to treat autoimmune diseases, disorders or conditions in addition to those listed above. Such diseases, disorders or conditions include Crohns disease, dermatomyositis, diabetes mellitus type 1, Goodpasture's syndrome, Graves' disease, Guillain-Barré syndrome, Hashimoto's disease, mixed connective tissue damage, myasthenia gravis, narcolepsy, pemphigus vulgaris, pernicious anemia, polymyositis, primary biliary cirrhosis, temporal arteritis, ulcerative colitis, vasculitis, and Wegener's granulomatosis, among others.

The compounds of Formula 1 may be used to treat inflammatory diseases, disorders or conditions including asthma, chronic inflammation, chronic prostatitis, glomerulonephritis, hypersensitivities, inflammatory bowel diseases (ulcerative colitis in addition to Crohn's disease), pelvic inflammatory disease, reperfusion injury, transplant rejection, vasculitis, and systemic inflammatory response syndrome.

The compounds of Formula 1 may also be used to treat specific diseases, disorders or conditions that may fall within one or more general disorders described above, including arthritis. In addition to rheumatoid arthritis, Sjögren's syndrome, systemic lupus erythematosus, SLE in children and adolescents, compounds of Formula 1 may also be used to treat other arthritis diseases, including ankylosing spondylitis, avascular necrosis, Behcet's disease, bursitis, calcium pyrophosphate dihyrate crystal deposition disease (pseudo gout), carpal tunnel syndrome, Ehlers-Danlos syndrome, fibromyalgia, Fifth disease, giant cell arteritis, gout, juvenile dermatomyositis, juvenile rheumatoid arthritis, juvenile spondyloarthopathy, Lyme disease, Marfan syndrome, myositis, osteoarthritis, osteogenesis imperfect, osteoporosis, Paget's disease, psoriatic arthritis, Raynaud's phenomenon, reactive arthritis, reflex sympathetic dystrophy syndrome, scleroderma, spinal stenosis, Still's disease, and tendinitis, among others.

The claimed and disclosed compounds may be combined with one or more other pharmacologically active compounds or therapies for the treatment of one or more diseases, disorders or conditions for which BTK is indicated, including those involving the immune system, inflammation, and abnormal cell growth. For example, compounds of Formula 1, which include compounds specifically named in the examples, and their pharmaceutically acceptable complexes, salts, solvates and hydrates, may be administered simultaneously, sequentially or separately in combination with one or more compounds or therapies for treating arthritis, including rheumatoid arthritis and osteoarthritis, or for treating cancer, including hematological malignancies, such as acute myeloid leukemia, B-cell chronic lymphocytic leukemia, B-cell lymphoma, T-cell lymphoma, multiple myeloma, and carcinomas, such as lung cancer, pancreatic cancer, and colon cancer. Such combinations may offer significant therapeutic advantages, including fewer side effects, improved ability to treat underserved patient populations, or synergistic activity.

For example, when used to treat arthritis, the compounds of Formula 1 may be combined with one or more nonsteroidal anti-inflammatory drugs (NSAIDs), analgesics, corticosteroids, biological response modifiers, and protein-A immunoadsorption therapy. Alternatively or additionally, when treating rheumatoid arthritis, the compounds of Formula 1 may be combined with one or more disease modifying anti-rheumatic drugs (DMARDs), and when treating osteoarthritis, the compounds of Formula 1 may be combined with one or more osteoporosis agents.

Representative NSAIDs include apazone, aspirin, celecoxib, diclofenac (with and without misoprostol), diflunisal, etodolac, fenoprofen, flurbiprofen, ibuprofen, indomethacin, ketoprofen, meclofenamate sodium, mefenamic acid, meloxicam, nabumetone, naproxen, oxaprozin, phenylbutazone, piroxicam, choline and magnesium salicylates, salsalate, and sulindac. Representative analgesics include acetaminophen and morphine sulfate, as well as codeine, hydrocodone, oxycodone, propoxyphene, and tramadol, all with or without acetaminophen. Representative corticosteroids include betamethasone, cortisone acetate, dexamethasone, hydrocortisone, methylprednisolone, prednisolone, and prednisone. Representative biological response modifiers include TNF-α inhibitors, such as adalimumab, etanercept, and infliximab; selective B-cell inhibitors, such as rituximab; IL-1 inhibitors, such as anakinra, and selective costimulation modulators, such as abatacept.

Representative DMARDs include auranofin (oral gold), azathioprine, chlorambucil, cyclophosamide, cyclosporine, gold sodium thiomalate (injectable gold), hydroxychloroquine, leflunomide, methotrexate, minocycline, myophenolate mofetil, penicillamine, and sulfasalazine. Representative osteoporosis agents include bisphosphonates, such as alendronate, ibandronate, risedronate, and zoledronic acid; selective estrogen receptor modulators, such as droloxifene, lasofoxifene, and raloxifene; hormones, such as calcitonin, estrogens, and parathyroid hormone; and immunosuppressant agents such as azathioprine, cyclosporine, and rapamycin.

Particularly useful combinations for treating rheumatoid arthritis include a compound of Formula 1 and methotrexate; a compound of Formula 1 and one or more biological response modifiers, such as lefluonomide, etanercept, adalimumab, and infliximab; or a compound of Formula 1, methotrexate, and one or more biological response modifiers, such as lefluonomide, etanercept, adalimumab, and infliximab.

For the treatment of thrombis and restensosis, the compounds of Formula 1 may be combined with one or more cardiovascular agents such as calcium channel blockers, statins, fibrates, beta-blockers, ACE inhibitors, and platelet aggregation inhibitors.

The compounds of Formula 1 may also be combined with one or more compounds or therapies for treating cancer. These include chemotherapeutic agents (i.e., cytotoxic or antineoplastic agents) such as alkylating agents, antibiotics, antimetabolic agents, plant-derived agents, and topoisomerase inhibitors, as well as molecularly targeted drugs which block the growth and spread of cancer by interfering with specific molecules involved in tumor growth and progression. Molecularly targeted drugs include both small molecules and biologics.

Representative alkylating agents include bischloroethylamines (nitrogen mustards, e.g., chlorambucil, cyclophosphamide, ifosfamide, mechlorethamine, melphalan, and uracil mustard); aziridines (e.g., thiotepa); alkyl alkone sulfonates (e.g., busulfan); nitrosoureas (e.g., carmustine, lomustine, and streptozocin); nonclassical alkylating agents (e.g., altretamine, dacarbazine, and procarbazine); and platinum compounds (e.g., carboplatin, cisplatin, nedaplatin, oxaliplatin, satraplatin, and triplatin tetranitrate).

Representative antibiotic agents include anthracyclines (e.g., aclarubicin, amrubicin, daunorubicin, doxorubicin, epirubicin, idarubicin, pirarubicin, valrubicin, and zorubicin); anthracenediones (e.g., mitoxantrone and pixantrone); and *streptomyces* (e.g., actinomycin, bleomycin, dactinomycin, mitomycin C, and plicamycin).

Representative antimetabolic agents include dihydrofolate reductase inhibitors (e.g., aminopterin, methotrexate, and pemetrexed); hymidylate synthase inhibitors (e.g., raltitrexed and pemetrexed); folinic acid (e.g., leucovorin); adenosine deaminase inhibitors (e.g., pentostatin); halogenated/ribonucleotide reductase inhibitors (e.g., cladribine, clofarabine, and fludarabine); thiopurines (e.g., thioguanine and mercaptopurine); thymidylate synthase inhibitors (e.g., fluorouracil, capecitabine, tegafur, carmofur, and floxuridine); DNA polymerase inhibitors (e.g., cytarabine); ribonucleotide reductase inhibitors (e.g., gemcitabine); hypomethylating agent (e.g., azacitidine and decitabine); and ribonucleotide reductase inhibitor (e.g., hydroxyurea); and an asparagine depleter (e.g., asparaginase)

Representative plant-derived agents include vinca alkaloids (e.g., vincristine, vinblastine, vindesine, vinzolidine, and vinorelbine), podophyllotoxins (e.g., etoposide and teniposide), and taxanes (e.g., docetaxel, larotaxel, ortataxel, paclitaxel, and tesetaxel).

Representative type I topoisomerase inhibitors include camptothecins, such as belotecan, irinotecan, rubitecan, and topotecan. Representative type II topoisomerase inhibitors include amsacrine, etoposide, etoposide phosphate, and teniposide, which are derivatives of epipodophyllotoxins.

Molecularly targeted therapies include biologic agents such as cytokines and other immune-regulating agents. Useful cytokines include interleukin-2 (IL-2, aldesleukin), interleukin 4 (IL-4), interleukin 12 (IL-12), and interferon, which includes more than 23 related subtypes. Other cytokines include granulocyte colony stimulating factor (CSF) (filgrastim) and granulocyte macrophage CSF (sargramostim). Other immuno-modulating agents include *bacillus* Calmette-Guerin, levamisole, and octreotide; monoclonal antibodies against tumor antigens, such as trastruzumab and rituximab; and cancer vaccines, which induce an immune response to tumors.

In addition, molecularly targeted drugs that interfere with specific molecules involved in tumor growth and progression include inhibitors of epidermal growth factor (EGF), transforming growth factor-alpha (TGF$_\alpha$), TGF$_\beta$, heregulin, insulin-like growth factor (IGF), fibroblast growth factor (FGF), keratinocyte growth factor (KGF), colony stimulating factor (CSF), erythropoietin (EPO), interleukin-2 (IL-2), nerve growth factor (NGF), platelet-derived growth factor (PDGF), hepatocyte growth factor (HGF), vascular endothelial growth factor (VEGF), angiopoietin, epidermal growth factor receptor (EGFR), human epidermal growth factor receptor 2 (HER2), HER4, insulin-like growth factor 1 receptor (IGF 1R), IGF2R, fibroblast growth factor 1 receptor (FGF1R), FGF2R, FGF3R, FGF4R, vascular endothelial growth factor receptor (VEGFR), tyrosine kinase with immunoglobulin-like and epidermal growth factor-like domains 2 (Tie-2), platelet-derived growth factor receptor (PDGFR), Abl, Bcr-Abl, Raf, FMS-like tyrosine kinase 3 (FLT3), c-Kit, Src, protein kinase c (PKC), tropomyosin receptor kinase (Trk), Ret, mammalian target of rapamycin (mTOR), Aurora kinase, polo-like kinase (PLK), mitogen activated protein kinase (MAPK), mesenchymal-epithelial transition factor (c-MET), cyclin-dependant kinase (CDK), Akt, extracellular signal-regulated kinases (ERK), poly(ADP) ribose polymerase (PARP), and the like.

Specific molecularly targeted drugs include selective estrogen receptor modulators, such as tamoxifen, toremifene, fulvestrant, and raloxifene; antiandrogens, such as bicalutamide, nilutamide, megestrol, and flutamide; and aromatase inhibitors, such as exemestane, anastrozole, and letrozole. Other specific molecularly targeted drugs include agents which inhibit signal transduction, such as imatinib, dasatinib, nilotinib, trastuzumab, gefitinib, erlotinib, cetuximab, lapatinib, panitumumab, and temsirolimus; agents that induce apoptosis, such as bortezomib; agents that block angiogenesis, such as bevacizumab, sorafenib, and sunitinib; agents that help the immune system destroy cancel cells, such as rituximab and alemtuzumab; and monoclonal antibodies which deliver toxic molecules to cancer cells, such as gemtuzumab ozogamicin, tositumomab, 131I-tositumoab, and ibritumomab tiuxetan.

Biological Activity

The activity of compounds as BTK inhibitors may be determined by a variety of methods, including in vitro and in vivo methods. The following in vitro assay measures a test compound's ability to inhibit BTK-mediated phosphorylation of a FAM-labeled substrate, 5-FAM-EEPLYWSFPAKKK-NH$_2$.

Purified BTK may be obtained as follows (Clone SBVC-1603_9P is used). A cDNA sequence encoding residues 382 to 659 of human BTK is cloned into the vector pSXB4. This construct engineers an in-frame translational fusion with the Glutathione-S-Transferase (GST) protein for use in affinity purification. The fusion protein derived from this construct contains a protease recognition sequence to liberate the BTK from the GST affinity tag. High-titer baculoviral stocks, generated using the Bac-to-Bac® system (Invitrogen), are used to express the recombinant protein in *Spodoptera frugiperda* Sf9 cells in 10 L Wave bags. Recombinant proteins are isolated from cellular extracts by passage over Glutathione Sepharose 4B (GE Healthcare) and the BTK moiety is released from the GST affinity tag by treatment with PreScission protease. The BTK recombinant protein is further purified by size exclusion chromatography (HiLoad 16/60 Superdex 200, GE Healthcare) in a buffer containing 20 mM Hepes (pH 7.4), 50 mM NaCl, 10 mM MgCl$_2$, 0.25 mM TCEP and 0.1 mM EDTA. The purity of the fractions is assessed by SDS PAGE and the peak protein fractions are pooled and concentrated using Amicon Ultra-15 Centrifugal Filter Devices (Millipore).

The inhibitory properties of compounds relative to BTK is determined using a black 384-well-plate format in a buffer which contains 50 mM Hepes, 10 mM NaCl, 10 mM MgCl$_2$, 0.2 mM EDTA, 0.01% Brij35®, 1 mM DTT, and 0.1 mg/mL BSA at pH 7.3. The test compound is prepared in DMSO using 2-fold serial dilutions for 11 data points, which are added to the buffer so that each dilution contains 3% DMSO. To initiate the assay, 5 µL of 3 µM 5FAM-EEPLYWSFPA- KKK-NH$_2$ (in buffer), 5 µL of diluted test compound (3% DMSO in buffer), and 5 µL of 9 nM BTK and 150 µM ATP in buffer are combined in each well. The reaction mixtures are incubated at room temperature for 60 minutes and then quenched by adding 25 µL of 50 mM EDTA. To quantify the fluorescent-labeled substrate and product following reaction, the test plate is loaded on a Caliper LC-3000, which measures percent of conversion by microfluidic-based separation. Corresponding IC$_{50}$ values are calculated by non-linear curve fitting of the compound concentrations and percent of inhibition to the standard IC$_{50}$ equation and reported as pIC$_{50}$, i.e., $-\log(IC_{50})$, where IC$_{50}$ is molar concentration at 50% inhibition.

EXAMPLES

The following examples are intended to be illustrative and non-limiting, and represent specific embodiments of the present invention.

$^1$H Nuclear magnetic resonance (NMR) spectra were obtained for many of the compounds in the following examples. Characteristic chemical shifts (δ) are given in parts-per-million downfield from tetramethylsilane using conventional abbreviations for designation of major peaks, including s (singlet), d (doublet), t (triplet), q (quartet), m (multiplet), and br (broad). The following abbreviations are used for common solvents: CDCl$_3$ (deuterochloroform), DMSO-d$_6$ (deuterodimethylsulfoxide), CD$_3$OD (deuteromethanol), CD$_3$CN (deuteroacetonitrile), and THF-d$_8$ (deuterotetrahydrofuran). The mass spectra (M+H) were recorded using either electrospray ionization (ESI-MS) or atmospheric pressure chemical ionization (APCI-MS).

Where indicated, products of certain preparations and examples are purified by mass-triggered HPLC (Pump: Waters™ 2525; MS: ZQ™; Software: MassLynx™), flash chromatography or preparative thin layer chromatography (TLC). Reverse phase chromatography is typically carried out on a column (e.g., Gemini™ 5 µm C18 110 Å, Axia™, 30×75 mm, 5 µm) under acidic conditions ("acid mode") eluting with ACN and water mobile phases containing 0.035% and 0.05% trifluoroacetic acid (TFA), respectively, or under basic conditions ("basic mode") eluting with water and 20/80 (v/v) water/acetonitrile mobile phases, both containing 10 mM NH$_4$HCO$_3$. Preparative TLC is typically carried out on silica gel 60 F$_{254}$ plates. After isolation by chromatography, the solvent is removed and the product is obtained by drying in a centrifugal evaporator (e.g., GeneVac™), rotary evaporator, evacuated flask, etc. Reactions in an inert (e.g., nitrogen) or reactive (e.g., H$_2$) atmosphere are typically carried out at a pressure of about 1 atmosphere (14.7 psi).

Preparation x1

4-amino-8-bromocinnoline-3-carboxamide

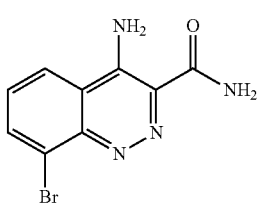 [SMILES: NC(=O)c1nnc2c(Br)cccc2c1N]

Step A: (E)-2-amino-N'-(2-bromophenyl)-2-oxoacetohydrazonoyl cyanide

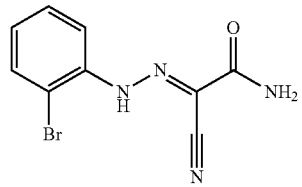 [SMILES: N#C/C(=N\Nc1ccccc1Br)C(N)=O]

To a stirred vessel containing 2-bromoaniline (10.3 g, 59.9 mmol) was added concentrated hydrochloric acid (15 mL) dropwise while maintaining the mixture temperature <5° C. To the cold suspension was added dropwise a solution of sodium nitrite (4.13 g, 59.9 mmol) in water (12.5 mL). The mixture was stirred and cooled for 15 minutes. A solution of sodium acetate (14.74 g, 180.0 mmol) in water (60 mL) was added dropwise to the reaction mixture. The resulting diazonium salt solution (cloudy yellow suspension) was set aside. While the diazonium salt solution was stirred and cooled, a solution of sodium acetate (4.91 g, 59.9 mmol) in water (17.5 mL) was added to a solution of 2-cyanoacetamide (5.03 g, 59.9 mmol) in water (85 mL) and EtOH (60 mL). The mixture was cooled to a temperature <10° C. at which point the diazonium salt solution was added portion-wise and with vigorous stirring over a span of 25 minutes while maintaining the reaction temperature <10° C. Upon completion of the addition, a thick reddish yellow precipitate formed, which was stirred overnight at room temperature. The solid product was collected by vacuum filtration, washed with water (500 mL), EtOH (500 mL), and Et$_2$O (500 mL), and then dried in a vacuum to afford the title compound as a yellow solid (8.0 g, 53%). $^1$H NMR (400 MHz, DMSO-d$_6$) δ ppm 7.06-7.13 (m, 1H), 7.43 (t, J=7.71 Hz, 1H), 7.57-7.72 (m, 2H), 7.92-8.02 (m, 2H), 10.03 (s, 1H).

Step B: 4-amino-8-bromocinnoline-3-carboxamide (E)-2-Amino-N'-(2-bromophenyl)-2-oxoacetohydrazonoyl cyanide (50.1 g, 187.5 mmol), AlCl$_3$ (100 g, 750 mmol), and chlorobenzene (419 mL, 412 mol) were stirred at 115° C. overnight under N$_2$. The reaction mixture was subsequently cooled to RT and 2M HCl (820 mL) was slowly added. The reaction mixture was stirred at 100° C. for 1 hour and then cooled. The product was collected by vacuum filtration, rinsed with EtOH (200 mL) and Et$_2$O (100 mL), and dried under high vacuum to give an HCl salt of the title compound as a yellow solid (31.25 g, 62.5%). $^1$H NMR (400 MHz, DMSO-d$_6$) δ ppm 9.91 (1H, s), 9.43 (1H, s), 8.61-8.59 (1H, d, J=8.4 Hz), 8.43 (1H, s), 8.32-8.30 (1H, d, J=7.6 Hz), 7.94 (1H, s), 7.69-7.65 (1H, m); LC-MS (5-95% ACN in H$_2$O gradient with 0.02% NH$_4$OAc, t$_R$ 2.659 minutes) ESI+APCI m/z [M+H]$^+$ 267.

Preparation x2

4-amino-8-bromo-7-methylcinnoline-3-carboxamide

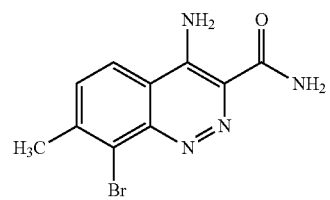 [SMILES: Cc1ccc2c(N)c(C(N)=O)nnc2c1Br]

The title compound was prepared in a manner similar to PREPARATION x1, using 2-bromo-3-methylaniline in place of 2-bromoaniline. $^1$H NMR (400 MHz, DMSO-d$_6$) δ ppm 2.60-2.70 (m, 3 H), 7.79 (d, J=8.84 Hz, 1 H), 8.00-8.13 (m, 1 H), 8.34 (br s, 1 H), 8.61 (d, J=8.59 Hz, 1 H), 9.76-10.31 (m, 2 H); ESI-MS m/z [M+H]$^+$ 281.5.

Preparations x3 and x4

4-amino-8-bromo-6-(trifluoromethyl)cinnoline-3-carboxamide and 4-amino-8-bromo-7-(trifluoromethyl)cinnoline-3-carboxamide

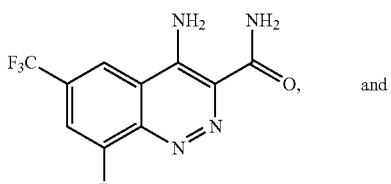

and

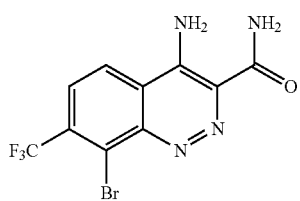

To a solution of 4-amino-8-bromocinnoline-3-carboxamide (500 mg, 1.872 mmol) in DCM (7 mL) and water (3 mL) was added sodium trifluoromethanesulfinate (876 mg, 5.62 mmol). The mixture was cooled to 0° C. and DMSO (7 mL) was added to homogenize the mixture. Next, 2-hydroperoxy-2-methylpropane (1.339 mL, 9.36 mmol) was slowly added, and the mixture was allowed to warm to RT. A second batch of sodium trifluoromethylsulfinate (117 mg, 0.75 mmol) was added, followed by 2-hydroperoxy-2-methylpropane (1.339 mL, 9.36 mmol). The reaction mixture was stirred vigorously and allowed to warm to room temperature. The progress of the reaction was monitored by UPLC. When product was formed, the mixture was partitioned between DCM (2.0 mL) and saturated sodium bicarbonate (2.0 mL). The organic layer was separated, and the aqueous layer was extracted with additional DCM (3×2.0 mL). The organic layers were combined, dried over sodium sulfate, and concentrated. The residue was reconstituted in a minimal amount of DCM and any solid residue was discarded. The solution was then purified by silica gel chromatography (30 μm Moritex® column) eluting with EtOAc/hexane (0-100% gradient). The appropriate fractions were collected to afford the title compounds. PREPARATION x3: $^1$H NMR (400 MHz, CD$_3$OD) δ ppm 4.17 (s, 3 H), 7.64 (d, J=9.09 Hz, 1 H), 7.80 (d, J=8.84 Hz, 1 H), 8.06 (s, 1 H), 8.15 (s, 1 H), 8.21 (d, J=1.26 Hz, 1 H), 8.99 (s, 1 H); ESI-MS m/z [M+H]$^+$ 335.1; and PREPARATION x4: $^1$H NMR (400 MHz, CD$_3$OD) δ ppm 4.19 (s, 3 H) 7.45 (dd, J=8.59, 0.76 Hz, 1 H) 7.79 (d, J=8.59 Hz, 1 H) 7.90 (s, 1 H) 8.13 (d, J=0.76 Hz, 1 H) 8.23 (d, J=9.09 Hz, 1 H) 8.73 (dd, J=8.97, 0.63 Hz, 1 H); ESI-MS m/z [M+H]$^+$ 335.1.

Preparation x5

4-amino-8-bromo-5-methoxycinnoline-3-carboxamide

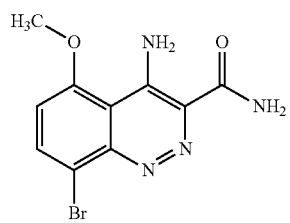 [SMILES: COc1ccc(Br)c2nnc(C(N)=O)c(N)c12]

The title compound was prepared in a manner similar to PREPARATION x1, using 2-bromo-5-methoxyaniline in place of 2-bromoaniline. $^1$H NMR (500 MHz, DMSO-d$_6$) δ ppm 4.01 (s, 3 H), 7.05 (d, J=8.30 Hz, 1 H), 7.66 (br s, 1 H), 8.10 (d, J=8.30 Hz, 1 H), 8.27 (br s, 1 H), 8.53 (br s, 1 H), 9.69 (br s, 1 H). ESI-MS m/z [M+H]$^+$ 297.3

Preparation x6

4-amino-8-bromo-7-methoxycinnoline-3-carboxamide

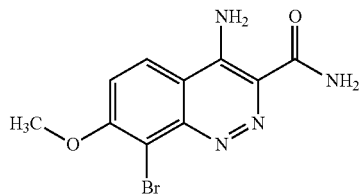 [SMILES: COc1ccc2c(N)c(C(N)=O)nnc2c1Br]

The title compound was prepared in a manner similar to PREPARATION x1, using 2-bromo-3-methoxyaniline in place of 2-bromoaniline. $^1$H NMR (500 MHz, DMSO-d$_6$) δ ppm 4.12 (s, 3 H), 7.74-7.81 (m, 1 H), 7.96 (br s, 1 H), 8.29 (br s, 1 H), 8.67 (d, J=9.27 Hz, 1 H); ESI-MS m/z [M+H]$^+$ 297.3.

Preparation x7

4-amino-8-bromo-5-methoxy-7-methylcinnoline-3-carboxamide

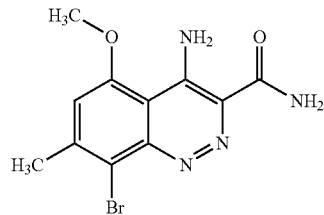 [SMILES: COc1cc(C)c(Br)c2nnc(C(N)=O)c(N)c12]

The title compound was prepared in a manner similar to PREPARATION x1, using 2-bromo-5-methoxy-3-methylaniline in place of 2-bromoaniline; ESI-MS m/z [M+H]+ 313.1.

Preparation x8

4-amino-8-fluorocinnoline-3-carboxamide

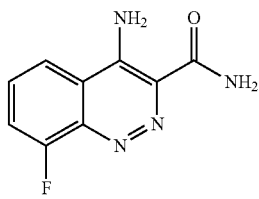 [SMILES: NC(=O)c1nnc2c(F)cccc2c1N]

The title compound was prepared in a manner similar to PREPARATION x1, using 2-fluoroaniline in place of 2-bromoaniline. $^1$H NMR (500 MHz, DMSO-d$_6$) δ ppm 7.80 (td, J=8.30, 5.37 Hz, 1 H), 7.85-7.93 (m, 1 H), 7.98 (br s, 1 H), 8.41 (d, J=8.79 Hz, 1 H), 8.47 (br s, 1 H), 9.66 (br s, 1 H), 10.13 (br s, 1 H); ESI-MS m/z [M+H]+ 207.5

Preparation x9

4-amino-8-bromo-5-fluorocinnoline-3-carboxamide

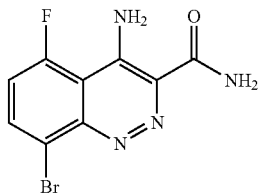 [SMILES: NC(=O)c1nnc2c(Br)ccc(F)c2c1N]

Step A: (E)-2-amino-N'-(2-bromo-5-fluorophenyl)-2-oxoacetohydrazonoyl cyanide

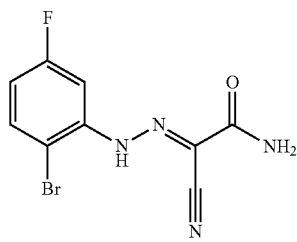 [SMILES: N#C/C(=N\Nc1cc(F)ccc1Br)C(N)=O]

To a stirred vessel containing 2-bromo-5-fluoroaniline (20.0 g, 105 mmol) was added concentrated hydrochloric acid (26 mL, 3.0 eq) dropwise while maintaining the mixture temperature <5° C. To the cooled suspension was added dropwise a solution of sodium nitrite (7.1 g, 103 mmol) in water (25 mL). The mixture was stirred and cooled for 15 minutes. A solution of sodium acetate (26.0 g, 317 mmol) in water (120 mL) was added dropwise to the reaction mixture. The resulting diazonium salt solution (cloudy yellow suspension) was set aside. While the diazonium salt solution was stirred and cooled, a solution of sodium acetate (8.6 g, 105 mmol) in water (30 mL) was added to a solution of 2-cyanoacetamide (8.8 g, 105 mmol) in water (150 mL) and EtOH (120 mL). The mixture was cooled to a temperature <10° C. at which point the diazonium salt solution was added portion-wise and with vigorous stirring over a span of 25 minutes while maintaining the reaction temperature <10° C. Upon addition of the diazonium salt solution, a thick reddish yellow precipitate formed, and the mixture was stirred overnight at room temperature. The solid product was collected by vacuum filtration, washed with water (300 mL) and EtOH (800 mL), and dried in a vacuum to afford the title compound as a red solid (20.0 g, 66.9%). $^1$H NMR (400 MHz, DMSO-d$_6$) δ ppm 14.52 (1H, s), 8.31 (1H, s), 8.12 (1H, s), 7.73-7.70 (1H, m), 7.36-7.33 (1H, m), 7.00-6.95 (1H, m).

Step B:
4-amino-8-bromo-5-fluorocinnoline-3-carboxamide (E)-2-Amino-N'-(2-bromo-5-fluorophenyl)-2-oxoacetohydrazonoyl cyanide (10 g, 35 mmol), AlCl$_3$ (20 g, 4.0 eq), and toluene (200 mL) were stirred at 120° C. overnight under N$_2$. The reaction mixture was subsequently cooled to 0° C. and 2N HCl (200 mL) was added. The reaction mixture was stirred at 0° C. for 10 minutes and then filtered to afford a crude solid (4.5 g), which was dispersed in EtOH (500 mL). The mixture was stirred at RT for 4 hours and filtered. The filtrate was concentrated to give the title compound (1.5 g, 15%). $^1$H NMR (400 MHz, DMSO-d$_6$) δ ppm 9.72 (1H, s), 8.62 (1H, s), 8.23-8.20 (1H, m), 8.00 (1H, s), 7.80 (1H, s), 7.47-7.42 (1H, m); LC-MS (5-95% ACN in H$_2$O gradient with 0.02% NH$_4$OAc, t$_R$ 3.020 minutes) ESI+APCI m/z [M+H]+ 285.

Preparation x10

4-amino-8-bromo-5,7-dimethylcinnoline-3-carboxamide

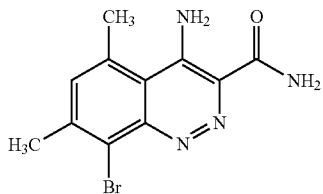 [SMILES: Cc1cc(C)c2c(N)c(C(N)=O)nnc2c1Br]

Step A: 2-bromo-1,5-dimethyl-3-nitrobenzene

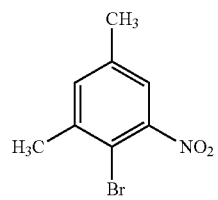

To a suspension of 2,4-dimethyl-6-nitroaniline (5 g, 30.12 mmol) in water (38 mL) was added HBr (15 mL, 40%). The mixture was heated to reflux for 10 minutes and then cooled to 0° C. A solution of NaNO$_2$ (2.07 g) in water (12 mL) was added dropwise with cooling. The mixture was stirred for 30 minutes and then added slowly to a stirred mixture of CuBr (4.33 g) in HBr (12 mL) and water (23 mL) at RT. The reaction mixture was stirred at RT for 30 minutes, heated to reflux for 3 hours, and then steam distilled. The distillate was extracted with DCM (3×30 mL), washed with aqueous saturated NaHCO$_3$ and saturated NaCl, and concentrated to give the title compound as a solid (1.8 g, 26%). $^1$H NMR (400 MHz, CDCl$_3$) δ ppm 7.26 (1H, s), 7.17 (1H, s), 2.39 (3H, s), 2.27 (3H, s).

Step B: 2-bromo-3,5-dimethylaniline

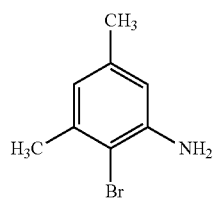

A mixture of 2-bromo-1,5-dimethyl-3-nitrobenzene (1.8 g, 7.8 mmol), Fe powder (2.2 g), concentrated hydrochloric acid (0.3 mL), and EtOH (20 mL) was stirred at 80° C. overnight. Ethyl acetate (20 mL) was subsequently added. The resulting suspension was filtered and the filtrate concentrated. The residue was treated with H$_2$O (10 mL), extracted with ethyl acetate (2×20 mL), washed with brine, dried over anhydrous Na$_2$SO$_4$, and concentrated to give the title compound as a solid (1.2 g, 77%).

Step C: 4-amino-8-bromo-5,7-dimethylcinnoline-3-carboxamide

The title compound was prepared in a manner similar to PREPARATION x1, using 2-bromo-3,5-dimethylaniline in place of 2-bromoaniline. $^1$H NMR (400 MHz, DMSO-d$_6$) δ ppm 8.58 (1H, s), 7.73 (1H, s), 7.42 (1H, s), 2.83 (3H, s), 2.56 (3H, s); LC-MS (5-95% ACN in H$_2$O gradient with 0.02% NH$_4$OAc, t$_R$ 3.283 minutes) ESI+APCI m/z [M+H]$^+$ 295.

Preparation x11

4-amino-8-bromo-7-chlorocinnoline-3-carboxamide

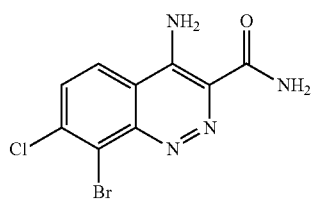 [SMILES: NC(=O)c1nnc2c(Br)c(Cl)ccc2c1N]

Step A: tert-butyl(2-bromo-3-chlorophenyl)carbamate

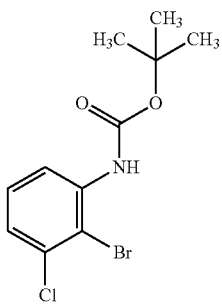 [SMILES: CC(C)(C)OC(=O)Nc1cccc(Cl)c1Br]

To a solution of 2-bromo-3-chlorobenzoic acid (0.5 g, 2.12 mmol) in toluene (5 mL) were added Et$_3$N (0.3 mL), DPPA (0.69 mL), and t-butanol (7.2 mL). The reaction mixture was heated at 100° C. overnight, cooled, and concentrated. This residue was extracted with ethyl acetate (20 mL). The organic phase was washed with aqueous HCl (5%, 20 mL), saturated NaHCO$_3$, and saturated NaCl, was dried over anhydrous Na$_2$SO$_4$, and was concentrated to give the title compound as a solid (0.4 g, 65%). $^1$H NMR (400 MHz, CDCl$_3$) δ 8.01 (1H, d, J=8.0 Hz), 7.19-7.12 (1H, m), 7.07-7.05 (2H, m), 1.46 (9H, s).

Step B: 2-bromo-3-chloroaniline

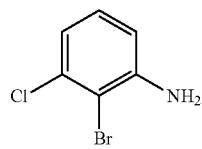

To tert-butyl(2-bromo-3-chlorophenyl)carbamate (0.4 g) in DCM (20 mL) was added TFA (10 mL). The reaction mixture was stirred at RT for 3 hours and then concentrated. Water (10 mL) was added to the residue, and the mixture was extracted with DCM (2×20 mL). The organic phase was separated, washed with aqueous saturated NaHCO$_3$ and saturated NaCl, dried over anhydrous Na$_2$SO$_4$, and concentrated to give the title compound as a solid (0.2 g, 77%). $^1$H NMR (400 MHz, CDCl$_3$) δ 7.03-6.99 (1H, m), 6.85-6.83 (1H, d, J=8.0 Hz), 6.65-6.63 (1H, d, J=8.0 Hz), 4.25 (2H, s).

Step C: 4-amino-8-bromo-7-chlorocinnoline-3-carboxamide

The title compound was prepared in a manner similar to PREPARATION x1, using 2-bromo-3-chloroaniline in place of 2-bromoaniline. $^1$H NMR (400 MHz, DMSO-d$_6$) δ 9.50 (1H, s), 8.76 (1H, s), 8.54 (1H, s), 8.50 (1H, d, J=8.8 Hz), 7.92

(1H, d, J=8.8 Hz), 7.81 (1H, s); LC-MS (5-95% ACN in H$_2$O gradient with 0.02% NH$_4$OAc, t$_R$ 3.228 minutes) ESI+APCI m/z [M+H]$^+$ 301.

Preparation x12

4-amino-8-bromo-5-fluoro-7-methylcinnoline-3-carboxamide

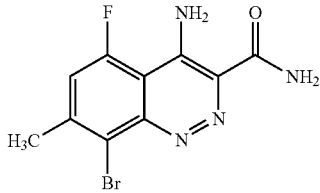 [SMILES: Cc1cc(F)c2c(N)c(C(N)=O)nnc2c1Br]

Step A: N-(4-fluoro-2-methylphenyl)acetamide

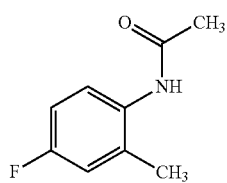

A mixture of 4-fluoro-2-methylaniline (20 g) and (CH$_3$CO)$_2$O (400 mL) was stirred at RT for 3 hours. The reaction mixture was subsequently poured into ice water (1000 mL), stirred for 10 minutes, filtered, and dried under vacuum to give the title compound (20 g, 74%).

Step B: N-(4-fluoro-2-methyl-6-nitrophenyl)acetamide

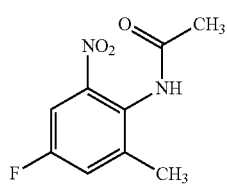

To a mixture of N-(4-fluoro-2-methylphenyl)acetamide (19 g, 113.1 mmol, 1 eq) and (CH$_3$CO)$_2$O (190 mL) was added HNO$_3$ (11.4 mL, 1.0 eq) dropwise at 0° C. The reaction mixture was allowed to warm to RT overnight and was subsequently poured onto ice and extracted with DCM. The organic phase was washed with aqueous NaHCO$_3$ until the pH of the aqueous layer was >7. The organic phase was washed with water and then dried over Na$_2$SO$_4$. The solvent was evaporated to give the title compound as a crude solid (20 g, 84%). $^1$H NMR (400 MHz, DMSO-d$_6$) δ ppm 9.82 (1H, s), 7.71 (1H, dd, J$_1$=2.8 Hz, J$_2$=8.0 Hz), 7.56 (1H, dd, J$_1$=2.8 Hz, J$_2$=9.2 Hz), 2.32 (3H, s), 2.02 (3H, s).

Step C: 4-fluoro-2-methyl-6-nitroaniline

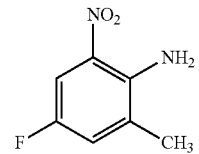

A mixture of N-(4-fluoro-2-methyl-6-nitrophenyl)acetamide (20 g, crude), concentrated hydrochloric acid (100 mL), and H$_2$O (100 mL) was refluxed overnight. The reaction mixture was subsequently extracted with DCM. The organic phase was washed with aqueous NaHCO$_3$ until the pH of the aqueous layer was >7. The organic phase was washed with water and dried over Na$_2$SO$_4$. The solvent was evaporated to give the title compound as a solid (5.5 g, 34%). $^1$H NMR (400 MHz, CDCl$_3$) δ ppm 7.68 (1H, dd, J$_1$=2.8 Hz, J$_2$=9.2 Hz), 7.05 (1H, dd, J$_1$=2.8 Hz, J$_2$=8.0 Hz), 5.99 (2H, s), 2.19 (3H, s).

Step D: 2-bromo-5-fluoro-1-methyl-3-nitrobenzene

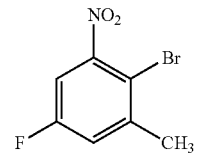

A suspension of 4-fluoro-2-methyl-6-nitroaniline (5.1 g, 30 mmol) in water (38 mL) and aqueous HBr (15 mL, 40%) was refluxed for 10 minutes and then cooled to 0° C. A solution of NaNO$_2$ (2.07 g, 30 mmol) in H$_2$O (12 mL) was added dropwise at a temperature <10° C. The diazonium solution was stirred for 30 minutes at a temperature of 0° C. to 5° C. and was then added slowly to a stirred mixture of CuBr (4.33 g, 30 mmol) in aqueous HBr (12 mL, 40%) and water (23 mL) at RT. The mixture was stirred at RT for 30 minutes and then on a steam bath for 1 hour. The reaction mixture was cooled to RT, DCM (50 mL) was added, and the mixture was washed with saturated NaHCO$_3$ and brine, dried over MgSO$_4$, and concentrated. The residue was purified by column chromatography, eluting with petroleum ether to give the title compound as an oil (2.0 g, 28%). $^1$H NMR (400 MHz, CDCl$_3$) δ ppm 7.23 (1H, dd, J$_1$=2.4 Hz, J$_2$=7.2 Hz), 7.14 (1H, dd, J$_1$=2.8 Hz, J$_2$=8.8 Hz), 2.44 (3H, s).

Step E: 2-bromo-5-fluoro-3-methylaniline

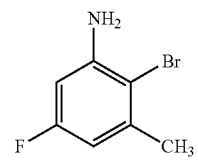

A suspension of 2-bromo-5-fluoro-1-methyl-3-nitrobenzene (2.0 g, 8.6 mmol), iron powder (2.4 g) in EtOH (20 mL), and concentrated hydrochloric acid (0.3 mL) was refluxed for 5 hours and then filtered and concentrated. Water (10 mL) was added to the residue and the resulting mixture was extracted with ethyl acetate (2×20 mL). The organic phase was washed with brine and concentrated to give the title compound as a solid (1.4 g, 80%). $^1$H NMR (400 MHz, CDCl$_3$) δ ppm 6.32-6.26 (2H, m), 4.15 (2H, s), 2.27 (3H, s).

Step F: 4-amino-8-bromo-5-fluoro-7-methylcinnoline-3-carboxamide

The title compound was prepared in a manner similar to PREPARATION x1, using 2-bromo-5-fluoro-3-methylaniline in place of 2-bromoaniline. $^1$H NMR (400 MHz, DMSO-d$_6$) δ 9.65 (1H, s), 8.59 (1H, s), 7.78-7.72 (2H, br s), 7.58 (1H, d, J=12.8 Hz), 2.61 (3H, s); LC-MS (5-95% ACN in H$_2$O gradient with 0.05% TFA, t$_R$ 2.581 minutes) ESI+APCI m/z [M+H]$^+$ 299.

Preparation x13

4-amino-8-bromo-6-fluorocinnoline-3-carboxamide

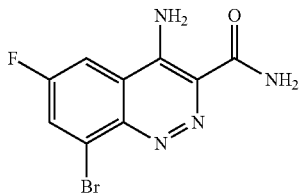 [SMILES: NC(=O)c1nnc2c(Br)cc(F)cc2c1N]

The title compound was prepared in a manner similar to PREPARATION x1, using 2-bromo-4-fluoroylaniline in place of 2-bromoaniline. $^1$H NMR (400 MHz, DMSO-d$_6$) δ 13.01 (1H, s), 9.16 (1H, br s), 8.42 (1H, s), 8.32 (1H, d, J=2.4 Hz), 8.22 (1H, br s), 8.05 (1H, s), 8.72 (1H, d, J=2.8 Hz), 7.64 (2H, s), 7.41 (1H, s), 2.01 (3H, s); LC-MS (20-95% ACN in H$_2$O gradient with 0.02% NH$_4$OAc, t$_R$ 2.579 minutes) ESI+APCI m/z [M+H]$^+$ 337.

Preparation x14

4-amino-8-bromo-7-ethylcinnoline-3-carboxamide

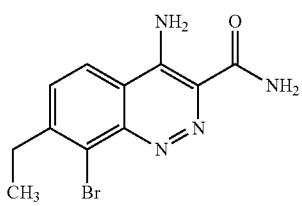 [SMILES: CCc1ccc2c(N)c(C(N)=O)nnc2c1Br]

Step A: N-(2-ethylphenyl)acetamide

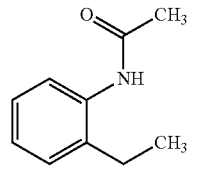

Acetyl chloride was slowly added to a chilled mixture of 2-ethylaniline (12.1 g, 100 mmol), Et$_3$N (20 mL, 145 mmol) and DCM (200 mL). Water (200 mL) was added and the layers separated. The organic layer was washed with water and brine, dried over Na$_2$SO$_4$, and concentrated to give the title compound as a yellow solid (16 g, 100%). $^1$H NMR (400 MHz, CDCl$_3$) δ 7.75 (1H, d, J=8.0 Hz), 7.20-7.24 (2H, m), 7.47 (1H, d, J=7.2 Hz), 6.95 (1H, s), 2.61 (2H, q, J=7.2 Hz), 2.21 (3H, s), 1.24 (3H, t, J=7.2 Hz).

Step B: N-(2-ethyl-6-nitrophenyl)acetamide

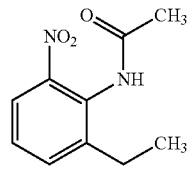

To a mixture of N-(2-ethylphenyl)acetamide (6.2 g, 38 mmol) in acetic acid (50 mL) was added dropwise fuming HNO$_3$ (13 mL, 310 mmol) at a temperature of 50° C. to 55° C. The mixture was allowed to react at 55° C. for 2 hours and was subsequently cooled to RT, poured onto ice, and extracted with DCM. The organic layer was washed with water until the pH of the aqueous phase was >7. The organic layer was washed again with water, dried over Na$_2$SO$_4$, and the solvent evaporated. The residue was purified using flash chromatography eluting with MeOH/DCM (1:400) to give the title compound as a yellow solid (2.4 g, 30%; 48% purity). $^1$H NMR (400 MHz, CD$_3$OD) δ 7.75 (1H, d, J=7.6 Hz), 7.62 (1H, d, J=7.6 Hz), 7.43 (1H, t, J=7.6 Hz), 2.71 (2H, q, J=7.6 Hz), 2.14 (3H, s), 1.21 (3H, t, J=7.6 Hz).

Step C: 2-ethyl-6-nitroaniline

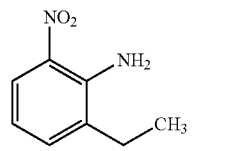

A mixture of crude N-(2-ethyl-6-nitrophenyl)acetamide (2.4 g, 12 mmol), H$_2$SO$_4$ (3.4 g, 36 mmol), and H$_2$O (10 mL) was refluxed for 2 hours and steam distilled. The distillate was extracted with Et$_2$O and the organic phase was washed with brine and dried over Na$_2$SO$_4$. The solvent was evaporated to give the title compound as a yellow liquid (0.5 g, 25%). $^1$H NMR (400 MHz, CD$_3$OD) δ 7.95 (1H, d, J=8.8 Hz), 7.31 (1H, d, J=6.8 Hz), 6.62 (1H, dd, J=8.8, 7.6 Hz), 2.63 (2H, q, J=7.6 Hz), 1.27 (3H, t, J=7.6 Hz).

Step D: 2-bromo-1-ethyl-3-nitrobenzene

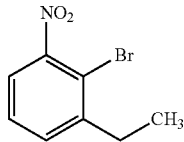

A suspension of 2-ethyl-6-nitroaniline (1.7 g, 10 mmol) in water (10 mL) and aqueous HBr (5 mL, 40%, 25 mmol) was refluxed for 10 minutes and then cooled to 0° C. A solution of NaNO$_2$ (0.7 g, 10 mmol) in H$_2$O (4 mL) was added dropwise at a temperature <10° C. The diazonium-containing solution was stirred for 30 minutes at a temperature of 0° C. to 5° C. and was then slowly added to a stirred mixture of CuBr (1.4 g, 10 mmol) in aqueous HBr (4 mL, 40%, 20 mmol) and water (8 mL) at RT. The mixture was stirred at RT for 30 minutes and then on a steam bath for 1 hour. The mixture was subsequently washed with aqueous saturated NaHCO$_3$ and brine, dried over MgSO$_4$, and concentrated. The residue was purified by column chromatography eluting with petroleum ether to give the title compound as a pale yellow oil (1.7 g, 75%). $^1$H NMR (400 MHz, CDCl$_3$) δ 7.50 (1H, dd, J=7.6, 1.6 Hz), 7.43 (1H, dd, J=8.0, 1.6 Hz), 7.37 (1H, dd, J=8.0, 7.6 Hz), 2.88 (2H, q, J=7.6 Hz), 1.28 (3H, t, J=7.6 Hz).

Step E: 2-bromo-3-ethylaniline

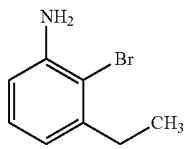

A suspension of 2-bromo-1-ethyl-3-nitrobenzene (9.2 g, 40 mmol) in EtOH (100 mL) in concentrated hydrochloric acid (0.17 mL, 2 mmol) was refluxed for 2 hours. The mixture was subsequently purified by column chromatography, eluting with petroleum ether to give the title compound as a red oil (6.5 g, 81%). $^1$H NMR (400 MHz, CDCl$_3$) δ 7.03 (1H, dd, J=7.6, 8.0 Hz), 6.64-6.62 (2H, m), 2.73 (2H, q, J=7.6 Hz), 1.22 (3H, t, J=7.6 Hz).

Step F:
4-amino-8-bromo-7-ethylcinnoline-3-carboxamide

An HCl salt of the title compound was prepared in a manner similar to PREPARATION x1, using 2-bromo-3-ethylaniline in place of 2-bromoaniline. $^1$H NMR (400 MHz, CD$_3$OD) δ 8.43 (1H, d, J=8.8 Hz), 7.85 (1H, d, J=8.8 Hz), 3.12 (2H, q, J=7.6 Hz), 1.36 (3H, t, J=7.6 Hz); LC-MS (5-95% ACN in H$_2$O gradient with 0.02% NH$_4$OAc, t$_R$ 3.203 minutes, 93% purity); ESI+APCI m/z [M+H]$^+$ 295.

Preparation x15

4-amino-8-bromo-6-methylcinnoline-3-carboxamide

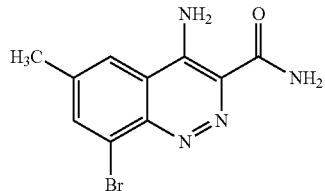 [SMILES: Cc1cc(Br)c2nnc(C(N)=O)c(N)c2c1]

The title compound was prepared in a manner similar to PREPARATION x1, using 2-bromo-4-methylaniline in place of 2-bromoaniline. $^1$H NMR (500 MHz, DMSO-d$_6$) δ ppm 2.51 (s, 3 H), 7.92 (s, 1 H), 8.21 (s, 1 H) 8.40 (m, 2 H), 9.25 (br s, 1 H), 9.82 (br s, 1 H). ESI-MS m/z [M+H]$^+$ 281.

Preparation x16

1-methyl-5-(4,4,5,5-tetramethyl-1,3,2-dioxaborolan-2-yl)-1H-benzo[d]imidazole

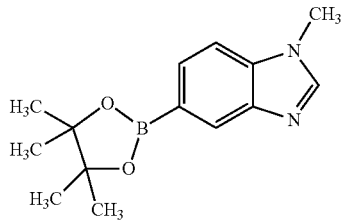 [SMILES: Cn1cnc2cc(B3OC(C)(C)C(C)(C)O3)ccc21]

5-bromo-1-methyl-1H-benzo[d]imidazole (500 mg, 2.369 mmol), potassium acetate (694 mg, 7.07 mmol), and 4,4,4',4',5,5,5',5'-octamethyl-2,2'-bi(1,3,2-dioxaborolane) (719 mg, 2.83 mmol) were mixed in dioxane and degassed with N$_2$ for 20 minutes. PdCl$_2$(dppf)CH$_2$Cl$_2$ adduct (193 mg, 0.236 mmol) was added in one portion and the reaction mixture was sealed and heated to 100° C. for 4 hours. The mixture, which contained the title compound, was used without further purification.

Preparation x17

1-isopropyl-5-(4,4,5,5-tetramethyl-1,3,2-dioxaborolan-2-yl)-1H-benzo[d]imidazole

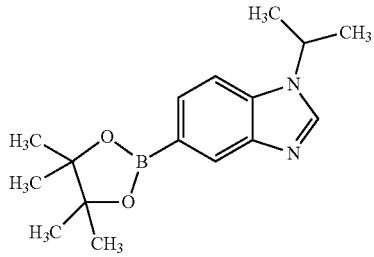 [SMILES: CC(C)n1cnc2cc(B3OC(C)(C)C(C)(C)O3)ccc21]

5-Bromo-1-isopropyl-1H-benzo[d]imidazole (500 mg, 2.091 mmol), potassium acetate (694 mg, 7.07 mmol) and 4,4,4',4',5,5,5',5'-octamethyl-2,2'-bi(1,3,2-dioxaborolane) (719 mg, 2.83 mmol) were mixed in dioxane and degassed with N$_2$ for 20 minutes. PdCl$_2$(dppf)CH$_2$Cl$_2$ adduct (193 mg, 0.236 mmol) was added in one portion and the reaction mixture was sealed and heated to 100° C. for 4 hours. The mixture, which contained the title compound, was used without further purification.

Preparation x18

1-cyclohexyl-5-(4,4,5,5-tetramethyl-1,3,2-dioxaborolan-2-yl)-1H-benzo[d]imidazole

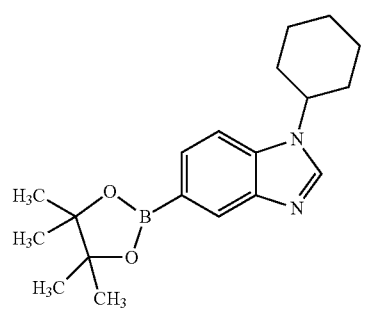 [SMILES: CC1(C)OB(c2ccc3c(c2)ncn3C2CCCCC2)OC1(C)C]

5-Bromo-1-cyclohexyl-1H-benzo[d]imidazole (500 mg, 1.791 mmol), potassium acetate (694 mg, 7.07 mmol) and 4,4,4',4',5,5,5',5'-octamethyl-2,2'-bi(1,3,2-dioxaborolane) (719 mg, 2.83 mmol) were mixed in dioxane and degassed with $N_2$ for 20 minutes. $PdCl_2$(dppf)$CH_2Cl_2$ adduct (193 mg, 0.236 mmol) was added in one portion and the reaction mixture was sealed and heated to 100 C for 4 hours. The mixture, which contained the title compound, was used without further purification.

Preparation x19

1-tert-butyl-5-(4,4,5,5-tetramethyl-1,3,2-dioxaborolan-2-yl)-1H-benzo[d]imidazole

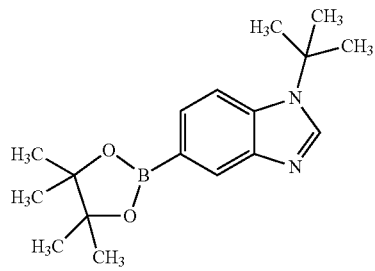 [SMILES: CC(C)(C)n1cnc2cc(B3OC(C)(C)C(C)(C)O3)ccc21]

5-Bromo-1-tert-butyl-1H-benzo[d]imidazole (500 mg, 1.975 mmol), potassium acetate (694 mg, 7.07 mmol) and 4,4,4',4',5,5,5',5'-octamethyl-2,2'-bi(1,3,2-dioxaborolane) (719 mg, 2.83 mmol) were mixed in dioxane and degassed with $N_2$ for 20 minutes. $PdCl_2$(dppf)$CH_2Cl_2$ adduct (193 mg, 0.236 mmol) was added in one portion and the reaction mixture was sealed and heated to 100° C. in a heating block for 4 hours. The mixture, which contained the title compound, was used without further purification.

Preparation x20

5-(4,4,5,5-tetramethyl-1,3,2-dioxaborolan-2-yl)isoindolin-1-one

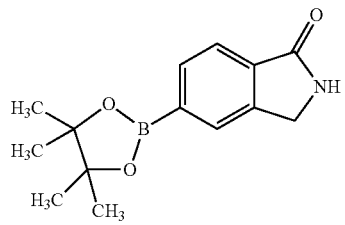 [SMILES: CC1(C)OB(c2ccc3c(c2)CNC3=O)OC1(C)C]

Step A: 5-bromoisoindolin-1-one

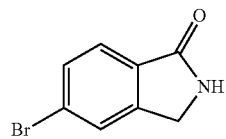

Methyl 4-bromo-2-(bromomethyl)benzoate (0.157 g, 0.510 mmol) was suspended in ammonia (2M solution in MeOH, 0.255 mL, 1.784 mmol). Ammonium hydroxide (0.517 mL, 7.65 mmol) was added and the mixture was stirred at RT overnight. A resulting white solid was collected by vacuum filtration, washed with water, and dried under high vacuum overnight to give the title compound as a white solid (0.066 g, 61%). $^1$H NMR (500 MHz, $CDCl_3$) δ ppm 4.45 (s, 2 H), 6.35 (br s, 1 H), 7.60-7.68 (m, 2 H), 7.74 (d, J=8.30 Hz, 1 H); ESI-MS m/z $[M+H]^+$ 212.3.

Step B: 5-(4,4,5,5-tetramethyl-1,3,2-dioxaborolan-2-yl)isoindolin-1-one

5-Bromoisoindolin-1-one (0.066 g, 0.311 mmol), bis(pinacolato)diboron (0.119 g, 0.467 mmol), potassium acetate (0.092 g, 0.934 mmol), and $PdCl_2$(dppf)$CH_2Cl_2$ adduct (0.013 g, 0.016 mmol) were suspended in DMA (0.6 mL), degassed with $N_2$, and stirred in a sand bath at 100° C. overnight. The reaction mixture was subsequently cooled, diluted with EtOAc (10 mL), and passed through a syringe filter. The filtrate was diluted with water (10 mL) and the layers were separated. The aqueous layer was washed with EtOAc (2×5 mL). The organic layers were combined and concentrated in vacuo to give the title compound as brown oil, which was used without further purification.

Preparation x21

2-methyl-5-(4,4,5,5-tetramethyl-1,3,2-dioxaborolan-2-yl)isoindolin-1-one

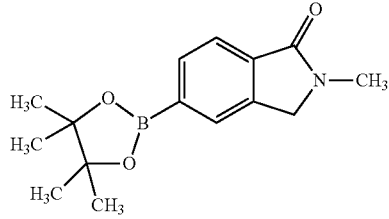

Step A: 5-bromo-2-methylisoindolin-1-one

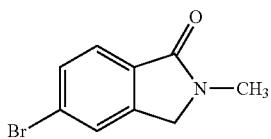

Methyl 4-bromo-2-(bromomethyl)benzoate (0.153 g, 0.497 mmol) was suspended in methanamine (2M solution in MeOH, 2.484 mL, 4.97 mmol) and the mixture was heated to reflux (90° C.) for 24 hours. The reaction mixture was cooled, concentrated in vacuo, and dried under high vacuum to give the title compound (0.112 g). $^1$H NMR (500 MHz, CDCl$_3$) δ ppm 3.19 (s, 3 H), 4.36 (s, 2 H), 7.57-7.62 (m, 2 H), 7.70 (d, J=8.30 Hz, 1 H); ESI-MS m/z [M+H]$^+$ 226.3.

Step B: 2-methyl-5-(4,4,5,5-tetramethyl-1,3,2-dioxaborolan-2-yl)isoindolin-1-one 5-Bromo-2-methylisoindolin-1-one (0.112 g, 0.495 mmol), bis(pinacolato)diboron (0.189 g, 0.743 mmol), potassium acetate (0.146 g, 1.486 mmol), and PdCl$_2$(dppf)CH$_2$Cl$_2$ adduct (0.020 g, 0.025 mmol) were suspended in DMA (1.0 mL). The mixture was degassed with N$_2$ and heated in a sand bath at 100° C. overnight. The reaction mixture was subsequently cooled, diluted with EtOAc (10 mL), and passed through a syringe filter. The filtrate was diluted with water (10 mL) and the layers were separated. The aqueous layer was washed with EtOAc (2×5 mL). The organic layers were combined and concentrated in vacuo to give the title compound as a brown residue, which was used without further purification.

Preparation x22

2-(3-hydroxy-3-methylbutyl)-5-(4,4,5,5-tetramethyl-1,3,2-dioxaborolan-2-yl)isoindolin-1-one

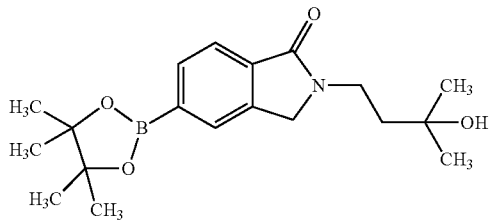 [SMILES: CC(C)(O)CCN1Cc2cc(B3OC(C)(C)C(C)(C)O3)ccc2C1=O]

Step A: 5-bromo-2-(3-hydroxy-3-methylbutyl)isoindolin-1-one

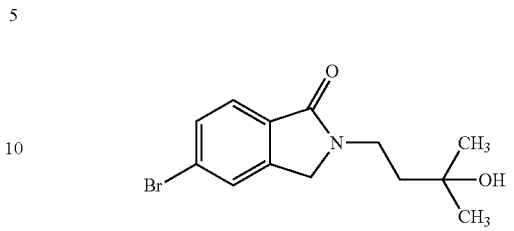

To methyl 4-bromo-2-(bromomethyl)benzoate (0.220 g, 0.714 mmol) suspended in MeOH (6.0 mL) were added 4-amino-2-methylbutan-2-ol (0.077 g, 0.750 mmol) and Et$_3$N (0.156 mL, 1.107 mmol). The mixture was heated to reflux (85° C.) for 24 hours, then cooled to RT, and concentrated in vacuo to give the title compound, which was used without further purification.

Step B: 2-(3-hydroxy-3-methylbutyl)-5-(4,4,5,5-tetramethyl-1,3,2-dioxaborolan-2-yl)isoindolin-1-one 5-Bromo-2-(3-hydroxy-3-methylbutyl)isoindolin-1-one (0.358 g, 1.201 mmol), bis(pinacolato)diboron (0.457 g, 1.801 mmol), potassium acetate (0.353 g, 3.60 mmol), and PdCl$_2$(dppf)CH$_2$Cl$_2$ adduct (0.049 g, 0.060 mmol) were suspended in DMA (4.0 mL), degassed with N$_2$, and heated in a sand bath at 100° C. overnight. The reaction mixture was subsequently cooled, diluted with EtOAc (40 mL), and passed through a pad of Celite. The filtrate was diluted with water (50 mL) and saturated brine (30 mL) and the layers were separated. The organic phase was dried over MgSO$_4$, filtered, and concentrated in vacuo. The crude product was purified by flash chromatography, eluting with 5% MeOH in DCM. The pure fractions were collected and concentrated to give the title compound as a brown oil. $^1$H NMR (500 MHz, DMSO-d$_6$) δ ppm 1.14 (s, 6 H), 1.28-1.35 (m, 12H), 1.65-1.72 (m, 2 H), 3.56-3.64 (m, 2 H), 4.33-4.36 (m, 1 H), 4.47 (s, 2 H), 7.63-7.68 (m, 1 H), 7.73-7.79 (m, 1H), 7.87 (s, 1 H); ESI-MS m/z [M+H]$^+$ 346.4.

Preparation x23

6-bromo-5-chloro-1H-indazole

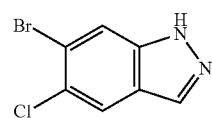

To 5-bromo-4-chloro-2-methylaniline (1 g, 4.54 mmol) in acetic acid (10 mL) was added a solution of sodium nitrite (0.329 g, 4.76 mmol) in water (1 mL). The mixture was heated at reflux for 2 hours and was subsequently cooled and concentrated. The residue was partitioned in water and extracted with EtOAc. The combined organic layers were washed with brine, dried over magnesium sulfate, and concentrated to give the title compound as a red-brown solid (0.67 g, 64%). ESI-MS m/z [M+H]+ 232.2.

Preparation x24

5-methoxy-6-(4,4,5,5-tetramethyl-1,3,2-dioxaborolan-2-yl)-1H-indazole

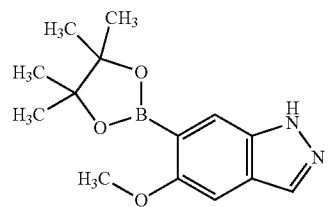 [SMILES: COc1cc2cn[nH]c2cc1B1OC(C)(C)C(C)(C)O1]

To a mixture of 6-bromo-5-methoxy-1H-indazole (2 g, 8.81 mmol), DMF (16 mL), potassium acetate (3.03 g, 30.8 mmol), and bis(pinacolato)diboron (3.36 g, 13.21 mmol), was added PdCl$_2$(dppf) (645 mg, 0.881 mmol). The mixture was purged with N$_2$ for one minute and then heated at 110° C. for 2 hours with stirring. The mixture was subsequently cooled and the product was purified by preparative HPLC, eluting with a gradient of ACN (5-30%) in H$_2$O. The relevant fractions were collected, concentrated, and dried in vacuo to give the title compound as a brown solid (1.71 g, 70.8%).

Example 1

4-amino-8-(1-methyl-1H-indazol-6-yl)cinnoline-3-carboxam

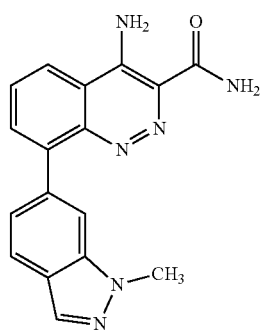 [SMILES: Cn1ncc2ccc(-c3cccc4c(N)c(C(N)=O)nnc34)cc21]

4-Amino-8-bromocinnoline-3-carboxamide hydrochloride (0.090 g, 0.296 mmol), 1-methyl-6-(4,4,5,5-tetramethyl-1,3,2-dioxaborolan-2-yl)-1H-indazole (0.115 g, 0.445 mmol) and 2M Na$_2$CO$_3$ (0.296 mL, 0.593 mmol) were suspended in dioxane. PdCl$_2$(dppf) (0.022 g, 0.030 mmol) was added and the mixture was heated in a microwave reactor at 140° C. for 45 minutes. The reaction mixture was filtered and concentrated. The residue was taken up in MeOH (5 mL) and purified by preparative HPLC (Sunfire Prep 5 µm C18, 75×30 mm column) eluting with a gradient of 15-40% ACN (containing 0.035% TFA) in water (containing 0.05% TFA). The pure fractions were collected, evaporated to a minimal volume, and lyophilized to give a TFA salt of the title compound (25 mg, 27%). $^1$H NMR (400 MHz, DMSO-d$_6$) δ ppm 4.09 (s, 3 H), 7.40 (dd, J=8.34, 1.01 Hz, 1 H), 7.77-7.93 (m, 3 H), 7.99 (dd, J=7.20, 1.14 Hz, 1 H), 8.14 (d, J=1.01 Hz, 1 H), 8.44 (br s, 1 H), 8.55 (d, J=8.59 Hz, 1H); ESI-MS m/z [M+H]+ 319.2.

Example 2

4-amino-8-(1-methyl-1H-indazol-5-yl)cinnoline-3-carboxamide

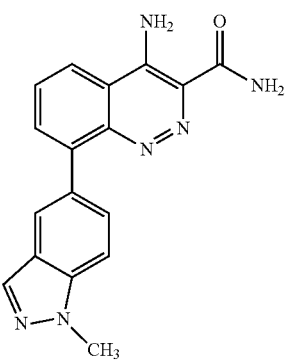 [SMILES: Cn1ncc2cc(-c3cccc4c(N)c(C(N)=O)nnc34)ccc21]

A TFA salt of the title compound was prepared in a manner similar to EXAMPLE 1 using 1-methyl-5-(4,4,5,5-tetramethyl-1,3,2-dioxaborolan-2-yl)-1H-indazole and 4-amino-8-bromocinnoline-3-carboxamide. $^1$H NMR (400 MHz, DMSO-d$_6$) δ ppm 4.14 (s, 3 H), 7.61 (dd, J=8.59, 1.52 Hz, 1 H), 7.82 (d, J=8.59 Hz, 1 H), 7.87-7.95 (m, 1 H), 7.96-8.05 (m, 2H), 8.17 (d, J=0.76 Hz, 1 H), 8.33 (s, 1 H), 8.61 (d, J=8.08 Hz, 1 H).

Example 3

4-amino-8-(1H-pyrrolo[3,2-b]pyridin-6-yl)cinnoline-3-carboxamide

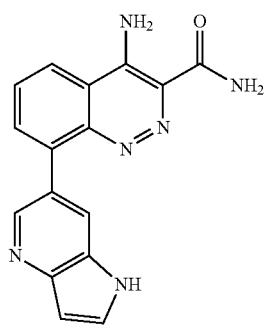 [SMILES: NC(=O)c1nnc2c(-c3cnc4cc[nH]c4c3)cccc2c1N]

A TFA salt of the title compound was prepared in a manner similar to EXAMPLE 1 using 6-(4,4,5,5-tetramethyl-1,3,2-dioxaborolan-2-yl)-1H-pyrrolo[3,2-b]pyridine and 4-amino-8-bromocinnoline-3-carboxamide. $^1$H NMR (500 MHz, CD$_3$OD) δ ppm 6.95 (dd, J=3.42, 0.98 Hz, 1 H), 7.90 (dd, J=8.30, 7.32 Hz, 1 H), 8.06-8.11 (m, 1 H), 8.19 (d, J=2.93 Hz, 1 H), 8.47 (dd, J=8.30, 0.98 Hz, 1 H), 8.80 (s, 1 H), 8.90 (d, J=1.46 Hz, 1 H).

Example 4

4-amino-8-(1H-benzo[d]imidazol-6-yl)cinnoline-3-carboxamide

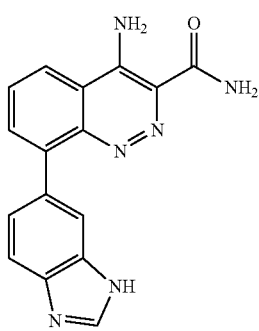 [SMILES: NC(=O)c1nnc2c(-c3ccc4nc[nH]c4c3)cccc2c1N]

A TFA salt of the title compound was prepared in a manner similar to EXAMPLE 1 using 6-(4,4,5,5-tetramethyl-1,3,2-dioxaborolan-2-yl)-1H-benzo[d]imidazole and 4-amino-8-bromocinnoline-3-carboxamide. $^1$H NMR (500 MHz, CD$_3$OD) δ ppm 7.78 (d, J=8.30 Hz, 1H), 7.95-8.00 (m, 1 H), 8.05 (d, J=7.81 Hz, 1 H), 8.07-8.10 (m, 2 H), 8.57 (d, J=8.30 Hz, 1H), 9.32 (br s, 1 H).

Example 5

4-amino-8-(1-methyl-1H-indol-5-yl)cinnoline-3-carboxamide

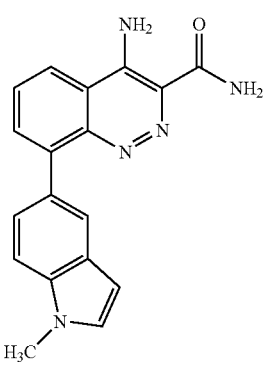 [SMILES: Cn1ccc2cc(-c3cccc4c(N)c(C(N)=O)nnc34)ccc21]

A TFA salt of the title compound was prepared in a manner similar to EXAMPLE 1 using 1-methyl-1H-indol-5-ylboronic acid and 4-amino-8-bromocinnoline-3-carboxamide. ESI-MS m/z [M+H]$^+$ 318.

Example 6

4-amino-8-(7-fluoro-2-oxoindolin-5-yl)cinnoline-3-carboxamide

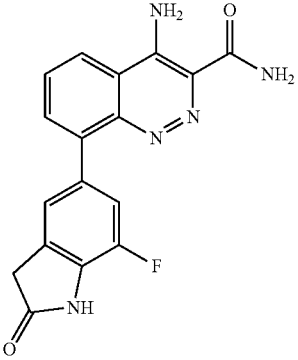 [SMILES: NC(=O)c1nnc2c(-c3cc(F)c4c(c3)CC(=O)N4)cccc2c1N]

A TFA salt of the title compound was prepared in a manner similar to EXAMPLE 1 using 7-fluoro-5-(4,4,5,5-tetramethyl-1,3,2-dioxaborolan-2-yl)indolin-2-one and 4-amino-8-bromocinnoline-3-carboxamide. ESI-MS m/z [M+H]$^+$ 337.

Example 7

4-amino-8-(1-methylindolin-5-yl)cinnoline-3-carboxamide

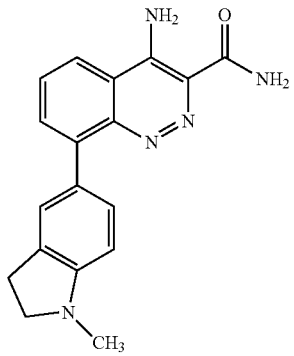 [SMILES: CN1CCc2cc(-c3cccc4c(N)c(C(N)=O)nnc34)ccc21]

A TFA salt of the title compound was prepared in a manner similar to EXAMPLE 1 using 1-methyl-5-(4,4,5,5-tetramethyl-1,3,2-dioxaborolan-2-yl)indoline and 4-amino-8-bromocinnoline-3-carboxamide. ESI-MS m/z [M+H]$^+$ 320.

Example 8

4-amino-8-(2-oxoindolin-5-yl)cinnoline-3-carboxamide

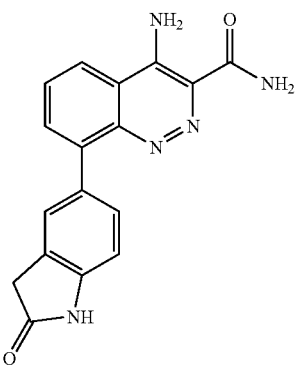 [SMILES: NC(=O)c1nnc2c(-c3ccc4c(c3)CC(=O)N4)cccc2c1N]

A TFA salt of the title compound was prepared in a manner similar to EXAMPLE 1 using 5-(4,4,5,5-tetramethyl-1,3,2-dioxaborolan-2-yl)indolin-2-one and 4-amino-8-bromocinnoline-3-carboxamide. ESI-MS m/z [M+H]⁺ 320.

Example 9

4-amino-8-(1-methyl-1H-indol-6-yl)cinnoline-3-carboxamide

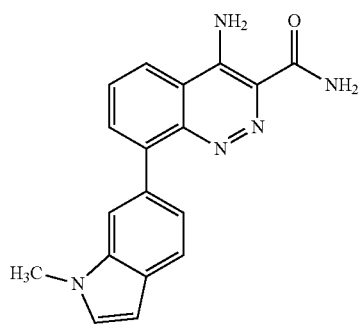 [SMILES: Cn1ccc2ccc(-c3cccc4c(N)c(C(N)=O)nnc34)cc21]

A TFA salt of the title compound was prepared in a manner similar to EXAMPLE 1 using 1-methyl-6-(4,4,5,5-tetramethyl-1,3,2-dioxaborolan-2-yl)-1H-indole and 4-amino-8-bromocinnoline-3-carboxamide. ESI-MS m/z [M+H]⁺ 318.

Example 10

4-amino-8-(imidazo[1,2-a]pyridin-6-yl)cinnoline-3-carboxamide

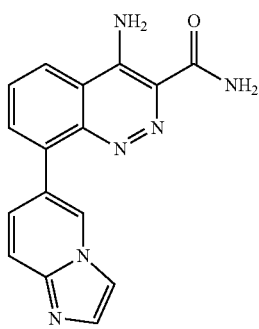 [SMILES: NC(=O)c1nnc2c(-c3ccc4nccn4c3)cccc2c1N]

A TFA salt of the title compound was prepared in a manner similar to EXAMPLE 1 using imidazo[1,2-a]pyridin-6-ylboronic acid and 4-amino-8-bromocinnoline-3-carboxamide. ESI-MS m/z [M+H]⁺ 305.

Example 11

4-amino-8-(2-methyl-2H-indazol-5-yl)cinnoline-3-carboxamide

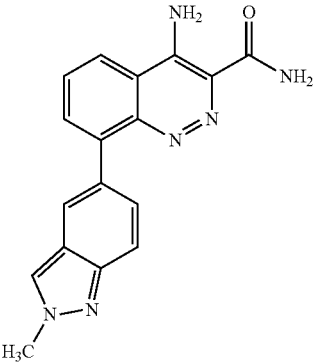 [SMILES: Cn1cc2cc(-c3cccc4c(N)c(C(N)=O)nnc34)ccc2n1]

A TFA salt of the title compound was prepared in a manner similar to EXAMPLE 1 using 2-methyl-5-(4,4,5,5-tetramethyl-1,3,2-dioxaborolan-2-yl)-2H-indazole and 4-amino-8-bromocinnoline-3-carboxamide. ESI-MS m/z [M+H]⁺ 319.

Example 12

4-amino-8-(1-methyl-1H-benzo[d]imidazol-5-yl)cinnoline-3-carboxamide

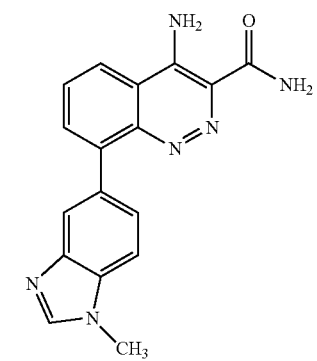 [SMILES: Cn1cnc2cc(-c3cccc4c(N)c(C(N)=O)nnc34)ccc21]

A formic acid salt of the title compound was prepared in a manner similar to EXAMPLE 1 using 1-methyl-5-(4,4,5,5-tetramethyl-1,3,2-dioxaborolan-2-yl)-1H-benzo[d]imidazole and 4-amino-8-bromocinnoline-3-carboxamide. ¹H NMR (500 MHz, CD₃OD) δ ppm 3.91 (s, 3 H), 8.54 (s, 1 H), 8.64 (d, J=8 Hz 1 H), 8.73 (d, J=8 Hz 2 H), 8.84 (d, J=16 Hz 1 H), 9.29 (d, J=8 Hz 1 H), 9.99 (s, 1 H); ESI-MS m/z [M+H]⁺ 319.2.

Example 13

4-amino-8-(3-methyl-3H-imidazo[4,5-b]pyridin-6-yl)cinnoline-3-carboxamide

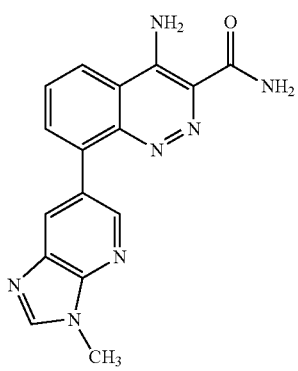 [SMILES: Cn1cnc2cc(-c3cccc4c(N)c(C(N)=O)nnc34)cnc21]

A TFA salt of the title compound was prepared in a manner similar to EXAMPLE 1 using 3-methyl-6-(4,4,5,5-tetramethyl-1,3,2-dioxaborolan-2-yl)-3H-imidazo[4,5-b]pyridine and 4-amino-8-bromocinnoline-3-carboxamide. $^1$H NMR (500 MHz, CD$_3$OD) δ ppm 4.03-4.12 (m, 3 H), 7.99 (dd, J=8.79, 7.32 Hz, 1 H), 8.11 (dd, J=7.32, 0.98 Hz, 1 H), 8.38 (s, 1 H), 8.54-8.64 (m, 1 H), 8.69 (d, J=1.95 Hz, 1 H), 8.84 (br s, 1 H).

Example 14

4-amino-8-(2-oxo-2,3-dihydro-1H-benzo[d]imidazol-5-yl)cinnoline-3-carboxamide

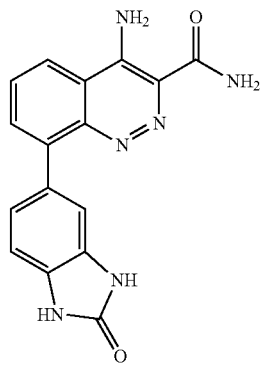 [SMILES: NC(=O)c1nnc2c(-c3ccc4[nH]c(=O)[nH]c4c3)cccc2c1N]

A TFA salt of the title compound was prepared in a manner similar to EXAMPLE 1 using 5-(4,4,5,5-tetramethyl-1,3,2-dioxaborolan-2-yl)-1H-benzo[d]imidazol-2(3H)-one and 4-amino-8-bromocinnoline-3-carboxamide. $^1$H NMR (400 MHz, CD$_3$OD) δ ppm 2.17 (s, 3 H), 6.29 (br s, 1 H), 6.32-6.45 (m, 1 H), 6.54 (d, J=7.07 Hz, 1 H), 7.08 (d, J=8.59 Hz, 1 H), 7.62 (br s, 1 H); ESI-MS m/z [M+H]$^+$ 321.2.

Example 15

4-amino-8-(1H-indol-6-yl)cinnoline-3-carboxamide

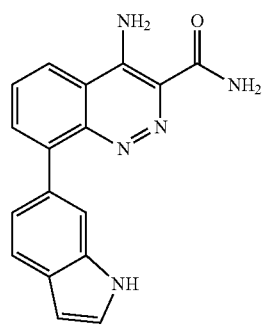 [SMILES: NC(=O)c1nnc2c(-c3ccc4cc[nH]c4c3)cccc2c1N]

A TFA salt of the title compound was prepared in a manner similar to EXAMPLE 1 using (1H-indol-6-yl)boronic acid and 4-amino-8-bromocinnoline-3-carboxamide. $^1$H NMR (400 MHz, DMSO-d$_6$) δ ppm 6.53 (br s, 1 H), 7.25 (d, J=8.08 Hz, 1 H), 7.47 (t, J=2.65 Hz, 1H), 7.61-7.73 (m, 2 H), 7.80-7.91 (m, 2 H), 7.91-8.01 (m, 1 H), 8.37 (br s, 1 H), 8.51 (d, J=8.59 Hz, 1 H), 11.29 (br s, 1 H); ESI-MS m/z [M+H]$^+$ 304.2.

Example 16

4-amino-8-(2-methyl-1H-benzo[d]imidazol-6-yl)cinnoline-3-carboxamide

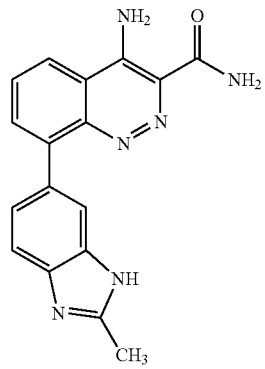 [SMILES: Cc1nc2ccc(-c3cccc4c(N)c(C(N)=O)nnc34)cc2[nH]1]

A TFA salt of the title compound was prepared in a manner similar to EXAMPLE 1 using 2-methyl-6-(4,4,5,5-tetramethyl-1,3,2-dioxaborolan-2-yl)-1H-benzo[d]imidazole and 4-amino-8-bromocinnoline-3-carboxamide. $^1$H NMR (400 MHz, CD$_3$OD) δ ppm 2.94 (s, 3 H), 7.71-7.82 (m, 1 H), 7.91-8.03 (m, 3 H), 8.04-8.10 (m, 1 H), 8.57 (d, J=8.08 Hz, 1 H); ESI-MS m/z [M+H]⁺ 319.2.

Example 17

4-amino-8-(1-isopropyl-1H-benzo[d]imidazol-5-yl)cinnoline-3-carboxamide

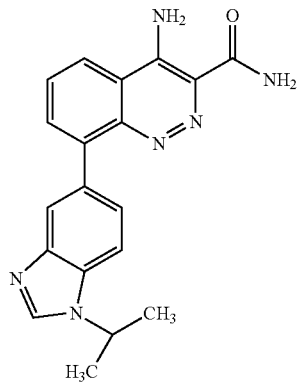 [SMILES: CC(C)n1cnc2cc(-c3cccc4c(N)c(C(N)=O)nnc34)ccc21]

The title compound was prepared in a manner similar to EXAMPLE 1 using 1-isopropyl-5-(4,4,5,5-tetramethyl-1,3,2-dioxaborolan-2-yl)-1H-benzo[d]imidazole and 4-amino-8-bromocinnoline-3-carboxamide. ¹H NMR (400 MHz, CD₃OD) δ ppm 1.70 (d, J=8 Hz, 6 H), 7.61 (dd, J=8, 4 Hz, 1 H), 7.76 (dd, J=8, 4 Hz, 1 H), 7.78-7.84 (m, 1 H), 7.85-7.92 (m, 1 H), 7.93 (m, 1 H), 8.30 (dd, J=8, 4 Hz, 1 H), 8.37 (s, 1 H); ESI-MS m/z [M+H]⁺ 347.3.

Example 18

4-amino-8-(1-cyclohexyl-1H-benzo[d]imidazol-5-yl)cinnoline-3-carboxamide

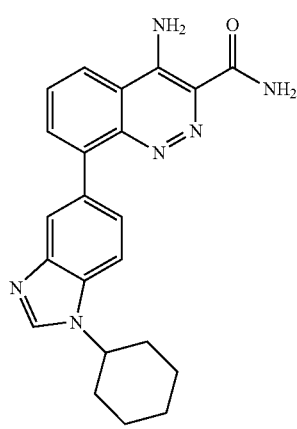 [SMILES: NC(=O)c1nnc2c(-c3ccc4c(c3)ncn4C3CCCCC3)cccc2c1N]

The title compound was prepared in a manner similar to EXAMPLE 1 using 1-cyclohexyl-5-(4,4,5,5-tetramethyl-1,3,2-dioxaborolan-2-yl)-1H-benzo[d]imidazole and 4-amino-8-bromocinnoline-3-carboxamide. ¹H NMR (400 MHz, CD₃OD) δ ppm 1.29 (t, J=8 Hz, 1 H), 1.44 (br s, 1 H), 1.52-1.71 (m, 2 H), 1.83 (d, J=12 Hz, 1 H), 1.88-2.08 (m, 3 H), 2.13-2.30 (m, 2 H), 7.58 (d, J=8 Hz, 1 H), 7.66-7.83 (m, 2 H), 7.83-7.96 (m, 2 H), 8.28 (d, J=8 Hz, 1 H), 8.35 (br s, 1 H), 8.62 (s, 1 H); ESI-MS m/z [M+H]⁺ 387.4.

Example 19

4-amino-8-(1-tert-butyl-1H-benzo[d]imidazol-5-yl)cinnoline-3-carboxamide

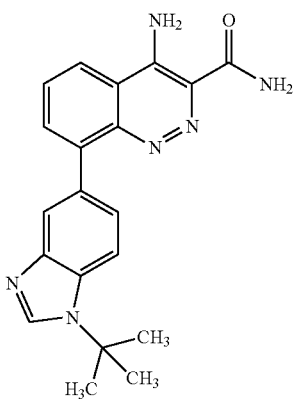 [SMILES: CC(C)(C)n1cnc2cc(-c3cccc4c(N)c(C(N)=O)nnc34)ccc21]

The title compound was prepared in a manner similar to EXAMPLE 1 using 1-tert-butyl-5-(4,4,5,5-tetramethyl-1,3,2-dioxaborolan-2-yl)-1H-benzo[d]imidazole and 4-amino-8-bromocinnoline-3-carboxamide. ¹H NMR (400 MHz, CD₃OD) δ ppm 1.85 (s, 9 H), 7.58 (m, 1 H), 7.76-7.83 (m, 1 H), 7.88 (d, J=8 Hz, 1 H), 7.91-7.96 (m, 2 H), 8.29 (m, 1 H), 8.32 (s, 1 H); ESI-MS m/z [M+H]⁺ 361.3.

Example 20

4-amino-8-(2-oxoindolin-6-yl)cinnoline-3-carboxamide

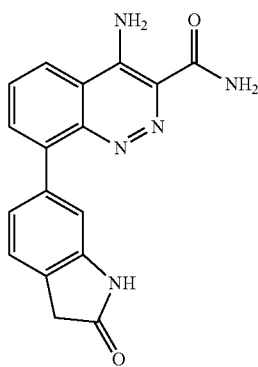 [SMILES: NC(=O)c1nnc2c(-c3ccc4c(c3)NC(=O)C4)cccc2c1N]

The title compound was prepared in a manner similar to EXAMPLE 1 using 2-oxoindolin-5-ylboronic acid and 4-amino-8-bromocinnoline-3-carboxamide. ESI-MS m/z [M+H]+ 320.2.

Example 21

4-amino-7-methyl-8-(1H-pyrrolo[3,2-b]pyridin-6-yl)cinnoline-3-carboxamide

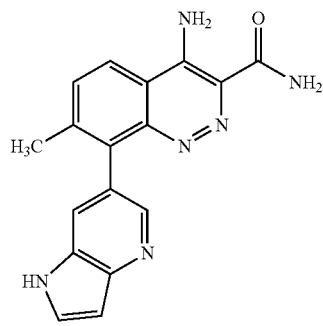 [SMILES: Cc1ccc2c(N)c(C(N)=O)nnc2c1-c1cnc2cc[nH]c2c1]

The title compound was prepared in a manner similar to EXAMPLE 1 using 6-(4,4,5,5-tetramethyl-1,3,2-dioxaborolan-2-yl)-1H-pyrrolo[3,2-b]pyridine and 4-amino-8-bromo-7-methylcinnoline-3-carboxamide. $^1$H NMR (400 MHz, DMSO-d$_6$) δ ppm 2.40 (s, 3H), 6.84 (br s, 1 H), 6.93 (br s, 1 H), 7.85 (d, J=8.59 Hz, 1 H), 8.15 (br s, 1 H), 8.27-8.30 (m, 1 H), 8.35 (s, 1 H), 8.54 (d, J=8.59 Hz, 1 H), 8.58 (s, 1 H), 8.71 (br s, 1 H), 8.76 (s, 1 H); ESI-MS m/z [M+H]+ 319.2.

Example 22

4-amino-8-(1H-benzo[d]imidazol-6-yl)-7-methylcinnoline-3-carboxamide

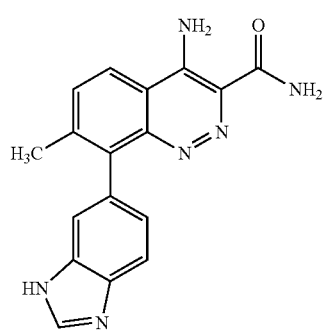 [SMILES: Cc1ccc2c(N)c(C(N)=O)nnc2c1-c1ccc2nc[nH]c2c1]

A TFA salt of the title compound was prepared in a manner similar to EXAMPLE 1 using 6-(4,4,5,5-tetramethyl-1,3,2-dioxaborolan-2-yl)-1H-benzo[d]imidazole and 4-amino-8-bromo-7-methylcinnoline-3-carboxamide. $^1$H NMR (400 MHz, DMSO-d$_6$) δ ppm 2.28 (s, 3H), 7.44 (d, J=8.08 Hz, 1 H), 7.78 (s, 1 H), 7.83 (d, J=8.84 Hz, 2 H), 7.95 (d, J=8.34 Hz, 1H), 8.24 (br s, 1 H), 8.51 (d, J=8.84 Hz, 1 H), 9.40 (br s, 1 H); ESI-MS m/z [M+H]+ 319.4.

Example 23

4-amino-7-methyl-8-(1-methyl-1H-benzo[d]imidazol-6-yl)cinnoline-3-carboxamide

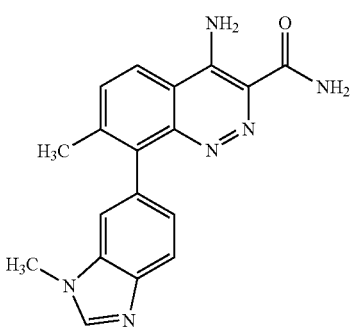 [SMILES: Cc1ccc2c(N)c(C(N)=O)nnc2c1-c1ccc2ncn(C)c2c1]

The title compound was prepared in a manner similar to EXAMPLE 1 using (1-methyl-1H-benzo[d]imidazol-6-yl)boronic acid and 4-amino-8-bromo-7-methylcinnoline-3-carboxamide. $^1$H NMR (400 MHz, DMSO-d$_6$) δ ppm 2.30 (s, 3 H), 3.83 (s, 3 H), 7.11 (dd, J=8.34, 1.52 Hz, 1 H), 7.49 (d, J=1.01 Hz, 1 H), 7.55 (br s, 1 H), 7.72 (t, J=8.46 Hz, 2 H), 8.22 (s, 1 H), 8.35 (s, 1 H), 8.37 (s, 1 H); ESI-MS m/z [M+H]+ 333.3.

Example 24

4-amino-8-(1H-indol-5-yl)-7-methylcinnoline-3-carboxamide

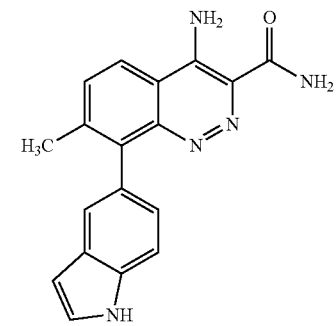 [SMILES: Cc1ccc2c(N)c(C(N)=O)nnc2c1-c1ccc2[nH]ccc2c1]

A TFA salt of the title compound was prepared in a manner similar to EXAMPLE 1 using 5-(4,4,5,5-tetramethyl-1,3,2-dioxaborolan-2-yl)-1H-indole and 4-amino-8-bromo-7-methylcinnoline-3-carboxamide. $^1$H NMR (400 MHz, DMSO-d$_6$) δ ppm 2.22-2.31 (m, 3 H), 6.52 (br s, 1 H), 6.94-7.03 (m, 1 H), 7.41-7.52 (m, 2 H), 7.57 (d, J=8.34 Hz, 1 H), 7.86 (d, J=8.84 Hz, 1 H), 7.98-8.18 (m, 2 H), 8.55 (d, J=8.84 Hz, 1 H), 11.33 (br s, 1 H); ESI-MS m/z [M+H]+ 318.3.

Example 25

4-amino-7-methyl-8-(1-methyl-1H-indazol-5-yl)cinnoline-3-carboxamide

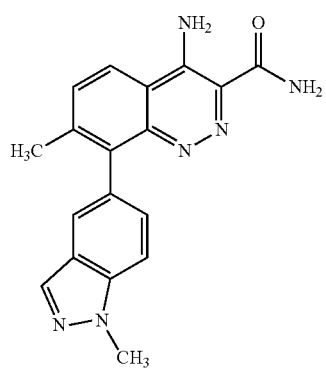 [SMILES: Cc1ccc2c(N)c(C(N)=O)nnc2c1-c1ccc2c(cnn2C)c1]

A TFA salt of the title compound was prepared in a manner similar to EXAMPLE 1 using 1-methyl-5-(4,4,5,5-tetramethyl-1,3,2-dioxaborolan-2-yl)-1H-indazole and 4-amino-8-bromocinnoline-3-carboxamide. $^1$H NMR (500 MHz, CD$_3$OD) δ ppm 2.34 (s, 3 H), 4.17-4.20 (m, 3 H), 7.40 (dd, J=8.30, 1.46 Hz, 1 H), 7.84-7.87 (m, 2 H), 7.90 (d, J=8.79 Hz, 1 H), 8.15 (d, J=0.98 Hz, 1 H), 8.46 (d, J=8.79 Hz, 1 H).

Example 26

4-amino-8-(1H-indol-6-yl)-7-methylcinnoline-3-carboxamide

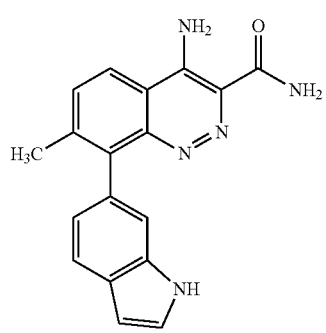 [SMILES: Cc1ccc2c(N)c(C(N)=O)nnc2c1-c1ccc2cc[nH]c2c1]

A TFA salt of the title compound was prepared in a manner similar to EXAMPLE 1 using (1H-indol-6-yl)boronic acid and 4-amino-8-bromo-7-methylcinnoline-3-carboxamide. $^1$H NMR (400 MHz, CD$_3$OD) δ ppm 2.39 (s, 3 H), 6.63-6.68 (m, 1 H), 7.01 (dd, J=8.08, 1.52 Hz, 1 H), 7.45 (ddt, J=5.40, 2.81, 1.07, 1.07 Hz, 2 H), 7.72-7.98 (m, 2 H), 8.45 (d, J=8.59 Hz, 1 H), 10.90 (br s, 1 H); ESI-MS m/z [M+H]+ 318.2.

Example 27

4-amino-8-(1H-indol-5-yl)cinnoline-3-carboxamide

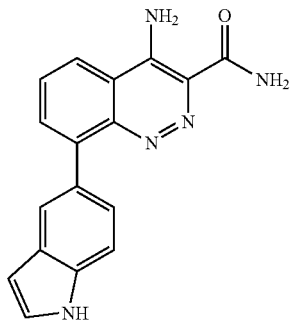 [SMILES: NC(=O)c1nnc2c(-c3ccc4[nH]ccc4c3)cccc2c1N]

A TFA salt of the title compound was prepared in a manner similar to EXAMPLE 1 using 5-(4,4,5,5-tetramethyl-1,3,2-dioxaborolan-2-yl)-1H-indole and 4-amino-8-bromocinnoline-3-carboxamide. $^1$H NMR (400 MHz, DMSO-d$_6$) δ ppm 6.53 (br s, 1 H), 7.29-7.61 (m, 3 H), 7.66-8.04 (m, 4 H), 8.27-8.61 (m, 2 H), 11.27 (br s, 1 H); ESI-MS m/z [M+H]+ 304.3.

Example 28

4-amino-8-(1H-indazol-6-yl)-7-methylcinnoline-3-carboxamide

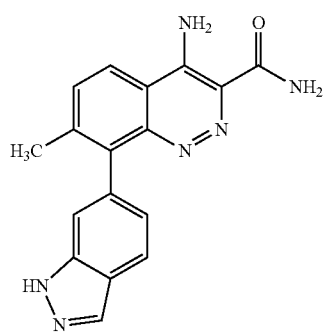 [SMILES: Cc1ccc2c(N)c(C(N)=O)nnc2c1-c1ccc2cn[nH]c2c1]

A TFA salt of the title compound was prepared in a manner similar to EXAMPLE 1 using (1H-indazol-6-yl)boronic acid and 4-amino-8-bromocinnoline-3-carboxamide. $^1$H NMR (500 MHz, CD$_3$OD) δ ppm 2.36 (s, 3 H), 7.13 (dd, J=8.30, 1.46 Hz, 1 H), 7.63-7.64 (m, 1 H), 7.90 (d, J=8.79 Hz, 1 H), 8.08 (d, J=8.30 Hz, 1 H), 8.23 (d, J=0.98 Hz, 1 H), 8.46 (d, J=8.30 Hz, 1 H); ESI-MS m/z [M+H]+ 319.3.

Example 29

4-amino-8-(1H-indazol-5-yl)-7-methylcinnoline-3-carboxamide

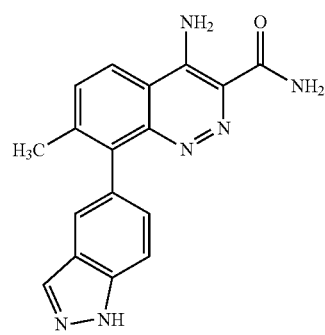 [SMILES: Cc1ccc2c(N)c(C(N)=O)nnc2c1-c1ccc2[nH]ncc2c1]

A TFA salt of the title compound was prepared in a manner similar to EXAMPLE 1 using (1H-indazol-5-yl)boronic acid and 4-amino-8-bromo-7-methylcinnoline-3-carboxamide. $^1$H NMR (400 MHz, DMSO-d$_6$) δ ppm 2.58 (br s, 3 H), 7.04-7.31 (m, 1 H), 7.56 (br s, 1 H), 7.67-7.85 (m, 1 H), 8.29 (s, 1 H), 8.43 (d, J=8 Hz, 1 H); ESI-MS m/z [M+H]+ 319.3.

Example 30

4-amino-8-(1,4-dimethyl-1H-indazol-5-yl)cinnoline-3-carboxamide

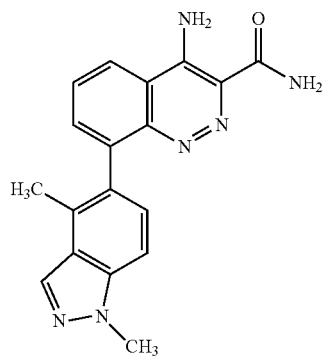 [SMILES: Cc1c(-c2cccc3c(N)c(C(N)=O)nnc23)ccc2c1cnn2C]

A TFA salt of the title compound was prepared in a manner similar to EXAMPLE 1 using (1,4-dimethyl-1H-indazol-5-yl)boronic acid and 4-amino-8-bromocinnoline-3-carboxamide. $^1$H NMR (500 MHz, DMSO-d$_6$) δ ppm 2.25 (s, 3 H), 4.11 (s, 3 H), 7.27 (d, J=8.79 Hz, 1 H), 7.58 (d, J=8.79 Hz, 1 H), 7.84-7.93 (m, 2 H), 7.96 (br s, 1 H), 8.22 (s, 1H), 8.25 (br s, 1 H), 8.62 (d, J=7.32 Hz, 1 H); ESI-MS m/z [M+H]+ 333.3.

Example 31

4-amino-8-(4-methyl-1H-indazol-5-yl)cinnoline-3-carboxamide

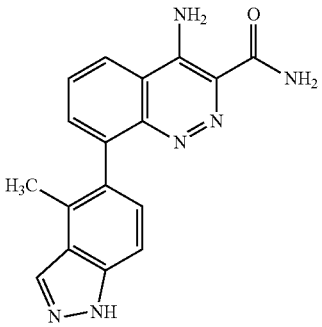 [SMILES: Cc1c(-c2cccc3c(N)c(C(N)=O)nnc23)ccc2[nH]ncc12]

A TFA salt of the title compound was prepared in a manner similar to EXAMPLE 1 using (4-methyl-1H-indazol-5-yl)boronic acid and 4-amino-8-bromocinnoline-3-carboxamide. $^1$H NMR (500 MHz, DMSO-d$_6$) δ ppm 2.26 (s, 3 H), 7.22 (d, J=8.79 Hz, 1 H), 7.47 (d, J=8.30 Hz, 1 H), 7.82-7.99 (m, 3 H), 8.24 (s, 2 H), 8.61 (d, J=7.32 Hz, 1 H); ESI-MS m/z [M+H]+ 319.3.

Example 32

4-amino-8-(1,7-dimethyl-1H-indazol-5-yl)-7-methylcinnoline-3-carboxamide

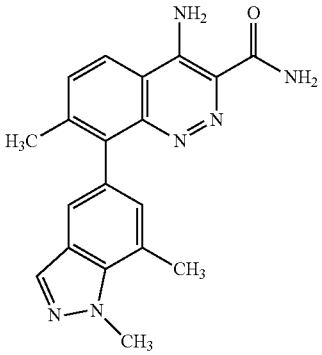 [SMILES: Cc1ccc2c(N)c(C(N)=O)nnc2c1-c1cc(C)c2c(cnn2C)c1]

A TFA salt of the title compound was prepared in a manner similar to EXAMPLE 1 using (1,7-dimethyl-1H-indazol-5-yl)boronic acid and 4-amino-8-bromo-7-methylcinnoline-3-carboxamide. $^1$H NMR (500 MHz, DMSO-d$_6$) δ ppm 2.27 (s, 3 H), 2.81 (s, 3 H), 4.36 (s, 3 H), 7.03 (d, J=1.46 Hz, 1 H), 7.53

(s, 1 H), 7.85 (d, J=8.79 Hz, 1 H), 7.99 (br s, 1 H), 8.05 (s, 1 H), 8.16 (br s, 1 H), 8.54 (d, J=8.79 Hz, 1 H); ESI-MS m/z [M+H]$^+$ 347.3.

Example 33

4-amino-7-methyl-8-(7-methyl-1H-indazol-5-yl)cinnoline-3-carboxamide

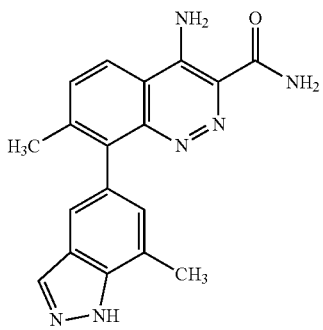 [SMILES: Cc1ccc2c(N)c(C(N)=O)nnc2c1-c1cc(C)c2[nH]ncc2c1]

A TFA salt of the title compound was prepared in a manner similar to EXAMPLE 1 using (7-methyl-1H-indazol-5-yl) boronic acid and 4-amino-8-bromo-7-methylcinnoline-3-carboxamide. $^1$H NMR (500 MHz, DMSO-d$_6$) δ ppm 2.27 (s, 3 H), 2.58 (s, 3 H), 7.04 (s, 1H), 7.54 (s, 1 H), 7.85 (d, J=8.79 Hz, 1 H), 7.97 (br s, 1 H), 8.15 (s, 2 H), 8.54 (d, J=8.79 Hz, 1 H); ESI-MS m/z [M+H]$^+$ 333.3.

Example 34

4-amino-8-(1-methyl-1H-indazol-5-yl)-6-(trifluoromethyl)cinnoline-3-carboxamide

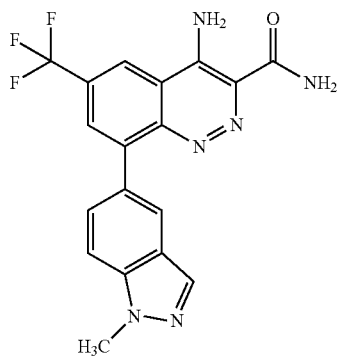 [SMILES: Cn1ncc2cc(-c3cc(C(F)(F)F)cc4c(N)c(C(N)=O)nnc34)ccc21]

A TFA salt of the title compound was prepared in a manner similar to EXAMPLE 1 using (1-methyl-1H-indazol-5-yl) boronic acid and 4-amino-8-bromo-6-(trifluoromethyl)cinnoline-3-carboxamide. $^1$H NMR (400 MHz, CD$_3$OD) δ ppm 4.17 (s, 3 H), 7.64 (d, J=9.09 Hz, 1 H), 7.80 (d, J=8.84 Hz, 1 H), 8.06 (s, 1 H), 8.15 (s, 1 H), 8.21 (d, J=1.26 Hz, 1 H), 8.99 (s, 1 H); ESI-MS m/z [M+H]$^+$ 387.2.

Example 35

4-amino-8-(1-methyl-1H-indazol-5-yl)-7-(trifluoromethyl)cinnoline-3-carboxamide

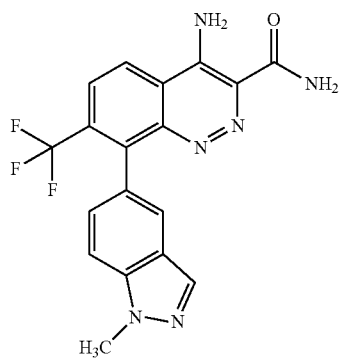 [SMILES: Cn1ncc2cc(-c3c(C(F)(F)F)ccc4c(N)c(C(N)=O)nnc34)ccc21]

A TFA salt of the title compound was prepared in a manner similar to EXAMPLE 1 using (1-methyl-1H-indazol-5-yl) boronic acid and 4-amino-8-bromo-7-(trifluoromethyl)cinnoline-3-carboxamide. $^1$H NMR (400 MHz, CD$_3$OD) δ ppm 4.19 (s, 3 H), 7.45 (dd, J=8.59, 0.76 Hz, 1 H), 7.79 (d, J=8.59 Hz, 1 H), 7.90 (s, 1 H), 8.13 (d, J=0.76 Hz, 1 H), 8.23 (d, J=9.09 Hz, 1 H), 8.73 (dd, J=8.97, 0.63 Hz, 1 H); ESI-MS m/z [M+H]$^+$ 387.2.

Example 36

4-amino-8-(1,3-dimethyl-1H-indazol-5-yl)-7-methylcinnoline-3-carboxamide

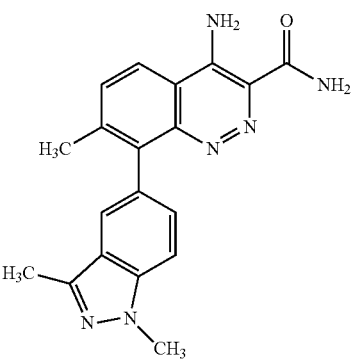 [SMILES: Cc1ccc2c(N)c(C(N)=O)nnc2c1-c1ccc2c(c1)c(C)nn2C]

A TFA salt of the title compound was prepared in a manner similar to EXAMPLE 1 using (1,3-dimethyl-1H-indazol-5-yl)boronic acid and 4-amino-8-bromo-7-methylcinnoline-3-carboxamide. $^1$H NMR (500 MHz, DMSO-d$_6$) δ ppm 2.27 (s, 3 H), 2.47-2.49 (m, 3 H), 4.05 (s, 3 H), 7.29 (dd, J=8.30, 1.46 Hz, 1 H), 7.68 (s, 1 H), 7.72 (d, J=8.30 Hz, 1 H), 7.86 (d, J=8.79 Hz, 1 H), 7.96 (br s, 1 H), 8.17 (br s, 1 H), 8.54 (d, J=8.79 Hz, 1 H); ESI-MS m/z [M+H]+ 347.4.

Example 37

4-amino-8-(1,3-dimethyl-1H-indazol-5-yl)cinnoline-3-carboxamide

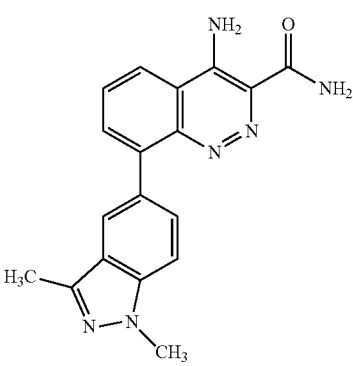 [SMILES: Cc1nn(C)c2ccc(-c3cccc4c(N)c(C(N)=O)nnc34)cc12]

A TFA salt of the title compound was prepared in a manner similar to EXAMPLE 1 using (1,3-dimethyl-1H-indazol-5-yl)boronic acid and 4-amino-8-bromocinnoline-3-carboxamide. $^1$H NMR (500 MHz, DMSO-$d_6$) δ ppm 2.51 (br s, 3 H), 4.03 (s, 3 H), 7.67 (s, 2H), 7.81 (br s, 1 H), 7.83-7.89 (m, 1 H), 7.92-7.98 (m, 2 H), 8.44 (br s, 1 H), 8.50 (d, J=8.30 Hz, 1 H); ESI-MS m/z [M+H]+ 333.4.

Example 38

4-amino-8-(1H-indazol-6-yl)-5-methoxycinnoline-3-carboxamide

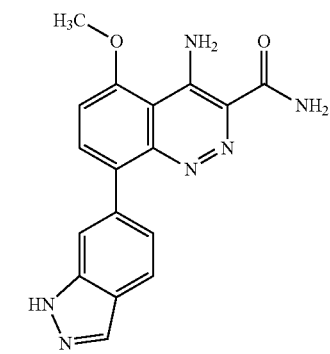 [SMILES: COc1ccc(-c2ccc3cn[nH]c3c2)c2nnc(C(N)=O)c(N)c12]

A TFA salt of the title compound was prepared in a manner similar to EXAMPLE 1 using (1H-indazol-6-yl)boronic acid and 4-amino-8-bromo-5-methoxycinnoline-3-carboxamide. $^1$H NMR (500 MHz, DMSO-$d_6$) δ ppm 2.54 (s, 2 H), 4.08 (s, 3 H), 7.29 (dd, J=19.04, 8.30 Hz, 2 H), 7.71 (s, 1 H), 7.78-7.89 (m, 2 H), 8.12 (s, 1 H), 8.44 (s, 1 H); ESI-MS m/z [M+H]+ 335.3.

Example 39

4-amino-5-methoxy-8-(5-methyl-1H-indazol-6-yl)cinnoline-3-carboxamide

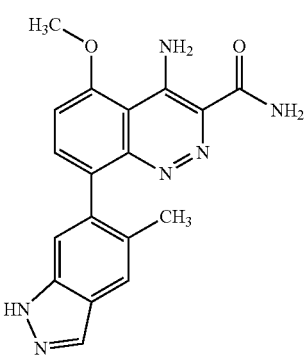 [SMILES: COc1ccc(-c2cc3[nH]ncc3cc2C)c2nnc(C(N)=O)c(N)c12]

A TFA salt of the title compound was prepared in a manner similar to EXAMPLE 1 using (5-methyl-1H-indazol-6-yl)boronic acid and 4-amino-8-bromo-5-methoxycinnoline-3-carboxamide. $^1$H NMR (500 MHz, DMSO-$d_6$) δ ppm 2.02 (s, 3 H), 4.12 (s, 3 H), 7.29-7.40 (m, 2 H), 7.68 (s, 1 H), 7.76 (d, J=4.88 Hz, 1 H), 8.06 (s, 1 H), 8.25 (br s, 1 H); ESI-MS m/z [M+H]+ 349.3.

Example 40

4-amino-8-(5-methyl-1H-indazol-6-yl)cinnoline-3-carboxamide

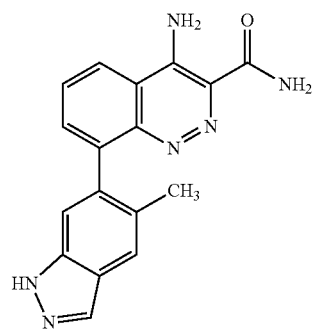 [SMILES: Cc1cc2cn[nH]c2cc1-c1cccc2c(N)c(C(N)=O)nnc12]

A TFA salt of the title compound was prepared in a manner similar to EXAMPLE 1 using (5-methyl-1H-indazol-6-yl)boronic acid and 4-amino-8-bromocinnoline-3-carboxamide. $^1$H NMR (500 MHz, DMSO-$d_6$) δ ppm 2.02 (s, 3 H), 7.43 (s, 1 H), 7.71 (s, 1H), 7.82-7.97 (m, 3 H), 8.09 (d, J=0.98 Hz, 1 H), 8.27 (br s, 1 H), 8.62 (d, J=8.30 Hz, 1 H), 10.06 (br s, 1 H); ESI-MS m/z [M+H]⁺ 319.4.

Example 41

4-amino-8-(1H-indazol-6-yl)-7-methoxycinnoline-3-carboxamide

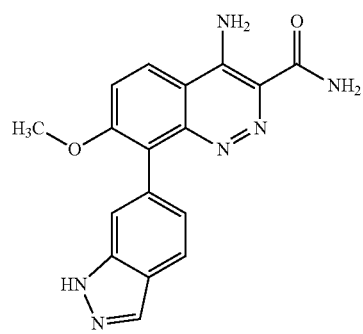 [SMILES: COc1ccc2c(N)c(C(N)=O)nnc2c1-c1ccc2cn[nH]c2c1]

A TFA salt of the title compound was prepared in a manner similar to EXAMPLE 1 using (1H-indazol-6-yl)boronic acid and 4-amino-8-bromo-7-methoxycinnoline-3-carboxamide. ¹H NMR (500 MHz, DMSO-d₆) δ ppm 3.93 (s, 3 H), 7.04 (dd, J=8.30, 1.46 Hz, 1 H), 7.51 (s, 1 H), 7.79-7.91 (m, 2 H), 8.15 (s, 2 H), 8.68 (br s, 1 H), 13.14 (br s, 1 H); ESI-MS m/z [M+H]⁺ 335.4.

Example 42

4-amino-8-(1H-indazol-6-yl)-5-methoxy-7-methyl-cinnoline-3-carboxamide

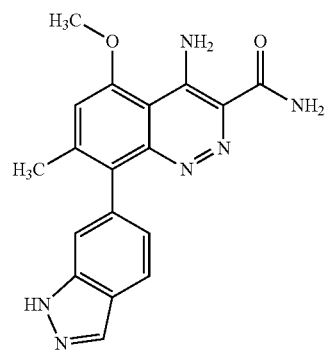 [SMILES: COc1cc(C)c(-c2ccc3cn[nH]c3c2)c2nnc(C(N)=O)c(N)c12]

A TFA salt of the title compound was prepared in a manner similar to EXAMPLE 1 using (1H-indazol-6-yl)boronic acid and 4-amino-8-bromo-5-methoxy-7-methylcinnoline-3-carboxamide. ¹H NMR (400 MHz, CD₃OD) δ ppm 2.33 (s, 3 H), 4.24 (s, 3 H), 7.11 (dd, J=8.08, 1.26 Hz, 1 H), 7.39 (s, 1 H), 7.61 (s, 1 H), 8.08 (dd, J=8.34, 0.76 Hz, 1 H), 8.28 (br s, 1H); ESI-MS m/z [M+H]⁺ 349.2.

Example 43

4-amino-5-fluoro-8-(5-methyl-1H-indazol-6-yl)cinnoline-3-carboxamide

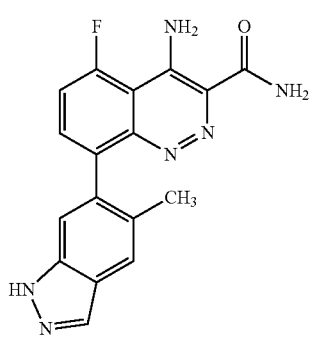

The title compound was prepared in a manner similar to EXAMPLE 1 using (6-methyl-1H-indazol-5-yl)boronic acid and 4-amino-8-bromo-5-fluorocinnoline-3-carboxamide. ¹H NMR (500 MHz, DMSO-d₆) δ ppm 1.98 (s, 3H), 7.34 (s, 1 H), 7.58 (dd, J=12.69, 7.81 Hz, 1 H), 7.61-7.70 (m, 3 H), 7.74 (dd, J=7.81, 5.37 Hz, 1 H), 8.03 (d, J=1.46 Hz, 1 H), 8.46 (br s, 1 H), 9.58 (br s, 1 H), 12.95 (s, 1 H); ESI-MS m/z [M+H]⁺ 337.4.

Example 44

4-amino-8-(1,5-dimethyl-1H-indazol-6-yl)cinnoline-3-carboxamide

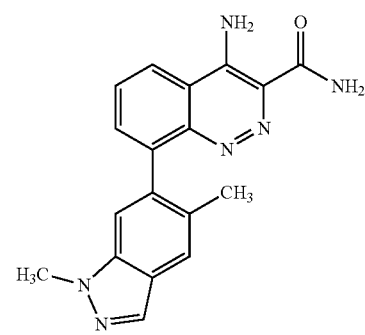 [SMILES: Cc1cc2cnn(C)c2cc1-c1cccc2c(N)c(C(N)=O)nnc12]

A TFA salt of the title compound was prepared in a manner similar to EXAMPLE 1 using 1,5-dimethyl-6-(4,4,5,5-tetramethyl-1,3,2-dioxaborolan-2-yl)-1H-indazole and 4-amino-8-bromocinnoline-3-carboxamide. ¹H NMR (500 MHz, CD₃OD) δ ppm 2.15 (s, 3 H), 4.07 (s, 3 H), 7.63 (s, 1 H), 7.85 (s, 1 H), 7.97-8.04 (m, 2 H), 8.07 (s, 1 H), 8.60 (dd, J=8.05, 1.71 Hz, 1 H); ESI-MS m/z [M+H]+ 333.4.

Example 45

4-amino-7-methyl-8-(1-methyl-1H-indazol-6-yl)cinnoline-3-carboxamide

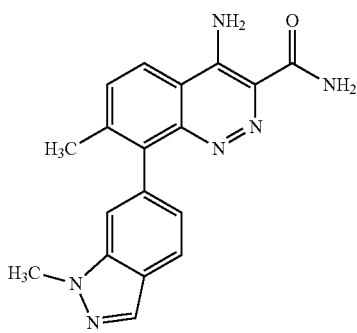 [SMILES: Cc1ccc2c(N)c(C(N)=O)nnc2c1-c1ccc2cnn(C)c2c1]

A TFA salt of the title compound was prepared in a manner similar to EXAMPLE 1 using 1-methyl-6-(4,4,5,5-tetramethyl-1,3,2-dioxaborolan-2-yl)-1H-indazole and 4-amino-8-bromo-7-methylcinnoline-3-carboxamide. $^1$H NMR (500 MHz, CD$_3$OD) δ ppm 2.34-2.38 (m, 3 H), 4.12 (s, 3 H), 7.15 (dd, J=8.30, 1.46 Hz, 1 H), 7.69 (d, J=0.98 Hz, 1 H), 7.91 (d, J=8.79 Hz, 1 H), 8.05 (dd, J=8.30, 0.98 Hz, 1H), 8.17 (s, 1 H), 8.47 (d, J=8.79 Hz, 1H); ESI-MS m/z [M+H]+ 333.4.

Example 46

4-amino-8-(1H-benzo[d]imidazol-6-yl)-7-methoxy-cinnoline-3-carboxamide

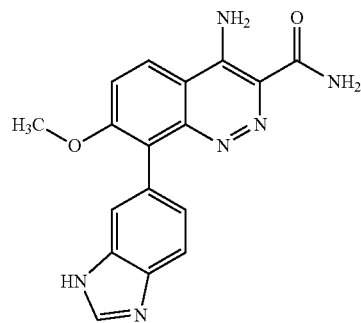 [SMILES: COc1ccc2c(N)c(C(N)=O)nnc2c1-c1ccc2nc[nH]c2c1]

A TFA salt of the title compound was prepared in a manner similar to EXAMPLE 1 using 6-(4,4,5,5-tetramethyl-1,3,2-dioxaborolan-2-yl)-1H-benzo[d]imidazole and 4-amino-8-bromo-7-methoxycinnoline-3-carboxamide. $^1$H NMR (500 MHz, CD$_3$OD) δ ppm 4.00 (s, 3H), 7.56 (dd, J=8.54, 1.22 Hz, 1 H), 7.78-7.95 (m, 2 H), 8.01 (d, J=8.79 Hz, 1 H), 8.65 (d, J=9.76 Hz, 1 H), 9.23 (s, 1 H); ESI-MS m/z [M+H]+ 335.4.

Example 47

4-amino-7-methyl-8-(1H-pyrazolo[3,4-b]pyridin-5-yl)cinnoline-3-carboxamide

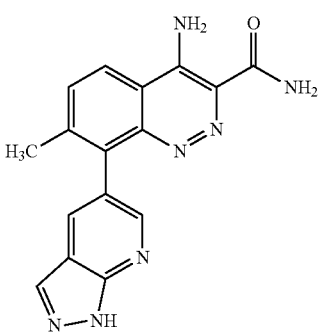

A TFA salt of the title compound was prepared in a manner similar to EXAMPLE 1 using 5-(4,4,5,5-tetramethyl-1,3,2-dioxaborolan-2-yl)-1H-pyrazolo[3,4-b]pyridine and 4-amino-8-bromo-7-methylcinnoline-3-carboxamide. $^1$H NMR (500 MHz, CD$_3$OD) δ ppm 2.36 (s, 3 H), 7.93 (d, J=8.79 Hz, 1 H), 8.28 (s, 1 H), 8.36 (d, J=1.95 Hz, 1 H), 8.44-8.62 (m, 2H); ESI-MS m/z [M+H]+ 320.4.

Example 48

4-amino-8-(1H-benzo[d][1,2,3]triazol-5-yl)-7-methylcinnoline-3-carboxamide

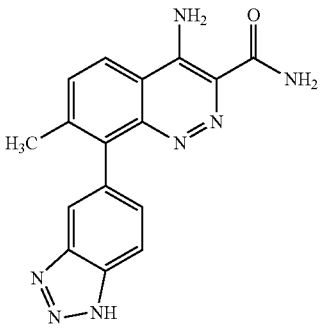 [SMILES: Cc1ccc2c(N)c(C(N)=O)nnc2c1-c1ccc2[nH]nnc2c1]

A TFA salt of the title compound was prepared in a manner similar to EXAMPLE 1 using 5-(4,4,5,5-tetramethyl-1,3,2-dioxaborolan-2-yl)-1H-benzo[d][1,2,3]triazole and 4-amino-8-bromo-7-methylcinnoline-3-carboxamide. $^1$H NMR (500 MHz, CD$_3$OD) δ ppm 2.35 (s, 3 H), 7.48 (dd, J=8.54, 1.22 Hz, 1 H), 7.91 (d, J=8.79 Hz, 1 H), 8.02 (s, 1 H), 8.16 (d, J=8.79 Hz, 1 H), 8.49 (d, J=8.79 Hz, 1 H); ESI-MS m/z [M+H]$^+$ 320.4.

Example 49

4-amino-8-(6-methyl-1H-indazol-5-yl)cinnoline-3-carboxamide

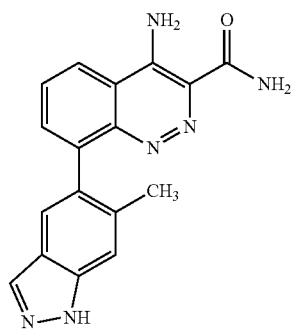 [SMILES: Cc1cc2[nH]ncc2cc1-c1cccc2c(N)c(C(N)=O)nnc12]

A TFA salt of the title compound was prepared in a manner similar to EXAMPLE 1 using (6-methyl-1H-indazol-5-yl) boronic acid and 4-amino-8-bromocinnoline-3-carboxamide. $^1$H NMR (500 MHz, CD$_3$OD) δ ppm 3.35 (s, 3 H), 7.65 (s, 1 H), 7.81 (s, 1 H), 7.96-8.03 (m, 2 H), 8.11 (s, 1 H), 8.56-8.61 (m, 1 H); ESI-MS m/z [M+H]$^+$ 319.4.

Example 50

4-amino-7-methyl-8-(3-methyl-1H-indazol-5-yl)cinnoline-3-carboxamide

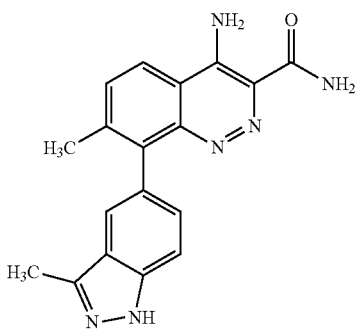 [SMILES: Cc1ccc2c(N)c(C(N)=O)nnc2c1-c1ccc2[nH]nc(C)c2c1]

A TFA salt of the title compound was prepared in a manner similar to EXAMPLE 1 using 3-methyl-5-(4,4,5,5-tetramethyl-1,3,2-dioxaborolan-2-yl)-1H-indazole and 4-amino-8-bromo-7-methylcinnoline-3-carboxamide. $^1$H NMR (500 MHz, CD$_3$OD) δ ppm 2.35 (s, 3 H), 2.60 (s, 3 H), 7.36 (dd, J=8.79, 1.46 Hz, 1 H), 7.74-7.78 (m, 1 H), 7.82 (s, 1 H), 7.90 (d, J=8.79 Hz, 1 H), 8.46 (d, J=8.79 Hz, 1 H); ESI-MS m/z [M+H]$^+$ 333.4.

Example 51

4-amino-8-(1H-indazol-5-yl)-7-methoxycinnoline-3-carboxamide

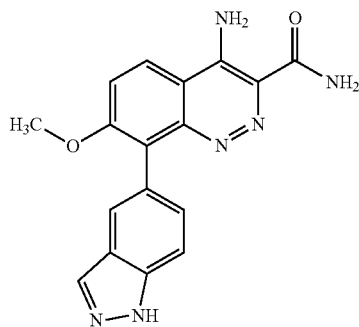 [SMILES: COc1ccc2c(N)c(C(N)=O)nnc2c1-c1ccc2[nH]ncc2c1]

A TFA salt of the title compound was prepared in a manner similar to EXAMPLE 1 using 5-(4,4,5,5-tetramethyl-1,3,2-dioxaborolan-2-yl)-1H-indazole and 4-amino-8-bromo-7-methoxycinnoline-3-carboxamide. $^1$H NMR (500 MHz, CD$_3$OD) δ ppm 4.01 (s, 3 H), 7.39 (d, J=8.79 Hz, 1 H), 7.77 (d, J=8.30 Hz, 1 H), 7.86 (t, J=4.39 Hz, 2 H), 8.17 (s, 1 H), 8.61 (d, J=9.27 Hz, 1 H); ESI-MS m/z [M+H]$^+$ 335.4.

Example 52

4-amino-7-methyl-8-(2-methyl-2H-indazol-6-yl)cinnoline-3-carboxamide

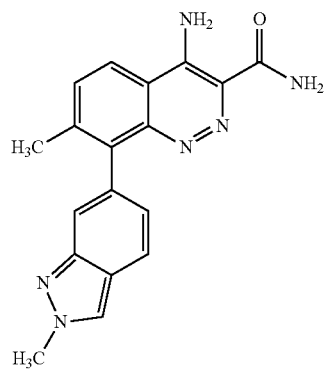 [SMILES: Cc1ccc2c(N)c(C(N)=O)nnc2c1-c1ccc2cn(C)nc2c1]

A TFA salt of the title compound was prepared in a manner similar to EXAMPLE 1 using 2-methyl-6-(4,4,5,5-tetramethyl-1,3,2-dioxaborolan-2-yl)-2H-indazole and 4-amino-8-bromo-7-methylcinnoline-3-carboxamide. $^1$H NMR (500 MHz, CD$_3$OD) δ ppm 2.37 (s, 3 H), 4.30 (s, 3 H), 7.04 (dd, J=8.54, 1.22 Hz, 1 H), 7.68 (d, J=1.46 Hz, 1 H), 7.89 (d, J=8.79 Hz, 1H), 7.99-8.01 (m, 1 H), 8.39 (s, 1 H), 8.46 (d, J=8.30 Hz, 1 H); ESI-MS m/z [M+H]+ 333.4.

Example 53

4-amino-8-(1H-indazol-6-yl)-5,7-dimethylcinnoline-3-carboxamide

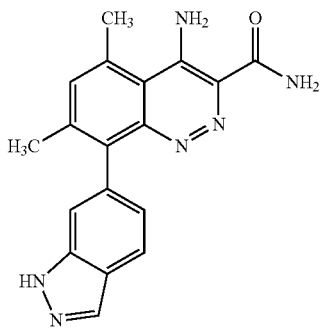 [SMILES: Cc1cc(C)c2c(N)c(C(N)=O)nnc2c1-c1ccc2cn[nH]c2c1]

A TFA salt of the title compound was prepared in a manner similar to EXAMPLE 1 using 6-(4,4,5,5-tetramethyl-1,3,2-dioxaborolan-2-yl)-1H-indazole and 4-amino-8-bromo-5,7-dimethylcinnoline-3-carboxamide. $^1$H NMR (500 MHz, CD$_3$OD) δ ppm 2.28 (d, J=1.95 Hz, 3 H), 3.02-3.09 (m, 3 H), 7.06-7.15 (m, 1 H), 7.61 (d, J=0.98 Hz, 1 H), 7.68 (s, 1 H), 8.08 (dt, J=8.30, 1.22 Hz, 1 H), 8.20-8.27 (m, 1H); ESI-MS m/z [M+H]+ 333.4.

Example 54

4-amino-7-chloro-8-(1H-indazol-6-yl)cinnoline-3-carboxamide

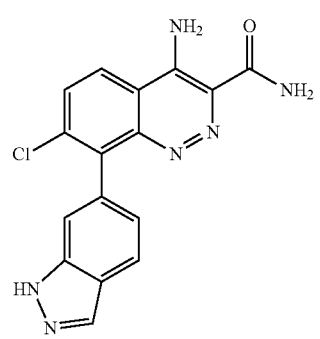 [SMILES: NC(=O)c1nnc2c(-c3ccc4cn[nH]c4c3)c(Cl)ccc2c1N]

A TFA salt of the title compound was prepared in a manner similar to EXAMPLE 1 using 6-(4,4,5,5-tetramethyl-1,3,2-dioxaborolan-2-yl)-1H-indazole and 4-amino-8-bromo-7-chlorocinnoline-3-carboxamide. $^1$H NMR (500 MHz, CD$_3$OD) δ ppm 7.17 (dd, J=8.30, 1.46 Hz, 1 H), 7.68 (d, J=0.98 Hz, 1 H), 8.00-8.10 (m, 2 H), 8.19-8.25 (m, 1 H), 8.53 (dd, J=8.79, 2.44 Hz, 1 H); ESI-MS m/z [M+H]+ 339.3.

Example 55

4-amino-8-(1,6-dimethyl-1H-indazol-5-yl)cinnoline-3-carboxamide

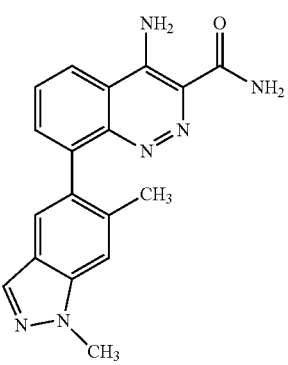 [SMILES: Cc1cc2c(cnn2C)cc1-c1cccc2c(N)c(C(N)=O)nnc12]

A TFA salt of the title compound was prepared in a manner similar to EXAMPLE 1 using 1,6-dimethyl-5-(4,4,5,5-tetramethyl-1,3,2-dioxaborolan-2-yl)-1H-indazole and 4-amino-8-bromocinnoline-3-carboxamide. $^1$H NMR (500 MHz, CD$_3$OD) δ ppm 2.21 (s, 3 H), 4.13 (s, 3 H), 7.67 (s, 1 H), 7.78 (s, 1 H), 7.95-8.02 (m, 2 H), 8.05 (s, 1 H), 8.57 (dd, J=6.59, 2.68 Hz, 1 H); ESI-MS m/z [M+H]+ 333.4.

Example 56

4-amino-5-fluoro-8-(1H-indazol-6-yl)-7-methylcinnoline-3-carboxamide

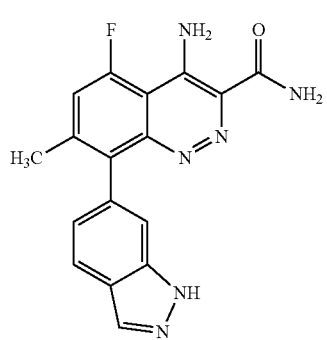 [SMILES: Cc1cc(F)c2c(N)c(C(N)=O)nnc2c1-c1ccc2cn[nH]c2c1]

A TFA salt of the title compound was prepared in a manner similar to EXAMPLE 1 using 6-(4,4,5,5-tetramethyl-1,3,2-dioxaborolan-2-yl)-1H-indazole and 4-amino-8-bromo-5-fluoro-7-methylcinnoline-3-carboxamide. $^1$H NMR (500 MHz, CD$_3$OD) δ ppm 2.34 (s, 3 H), 7.12 (dd, J=8.30, 0.98 Hz, 1 H), 7.64 (s, 1 H), 7.68 (d, J=13.67 Hz, 1 H), 8.09 (d, J=8.30 Hz, 1 H), 8.24 (d, J=0.98 Hz, 1 H); ESI-MS m/z [M+H]⁺ 337.2.

Example 57

4-amino-8-(isoquinolin-7-yl)-7-methylcinnoline-3-carboxamide

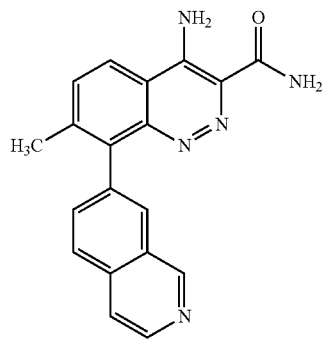 [SMILES: Cc1ccc2c(N)c(C(N)=O)nnc2c1-c1ccc2ccncc2c1]

The title compound was prepared in a manner similar to EXAMPLE 1 using 7-(4,4,5,5-tetramethyl-1,3,2-dioxaborolan-2-yl)isoquinoline and 4-amino-8-bromo-7-methylcinnoline-3-carboxamide. ¹H NMR (500 MHz, CD₃OD) δ ppm 2.30-2.36 (m, 3 H), 7.72-7.79 (m, 2 H), 7.94 (d, J=5.86 Hz, 1 H), 8.07-8.14 (m, 2 H), 8.22-8.31 (m, 1 H), 8.46-8.52 (m, 1 H), 9.29 (s, 1 H); ESI-MS m/z [M+H]⁺ 330.4.

Example 58

4-amino-8-(isoquinolin-6-yl)-7-methylcinnoline-3-carboxamide

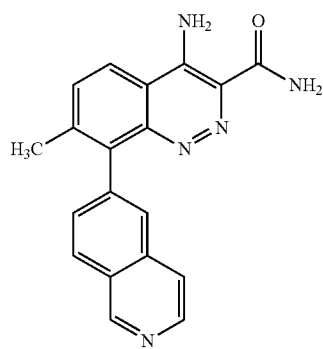 [SMILES: Cc1ccc2c(N)c(C(N)=O)nnc2c1-c1ccc2cnccc2c1]

The title compound was prepared in a manner similar to EXAMPLE 1 using isoquinolin-6-ylboronic acid and 4-amino-8-bromo-7-methylcinnoline-3-carboxamide. ¹H NMR (500 MHz, CD₃OD) δ ppm 2.34 (s, 3 H), 7.67 (d, J=8.30 Hz, 1 H), 7.76 (d, J=8.79 Hz, 1 H), 7.90 (d, J=5.86 Hz, 1 H), 7.94 (s, 1 H), 8.28 (t, J=8.30 Hz, 2 H), 8.50 (d, J=5.86 Hz, 1H), 9.35 (s, 1 H); ESI-MS m/z [M+H]⁺ 330.4.

Example 59

4-amino-8-(1H-indazol-6-yl)cinnoline-3-carboxamide

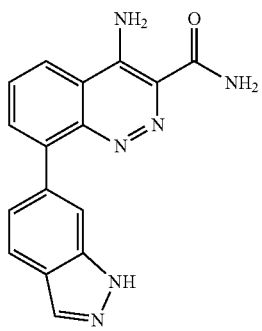 [SMILES: NC(=O)c1nnc2c(-c3ccc4cn[nH]c4c3)cccc2c1N]

A TFA salt of the title compound was prepared in a manner similar to EXAMPLE 1 using 6-(4,4,5,5-tetramethyl-1,3,2-dioxaborolan-2-yl)-1H-indazole and 4-amino-8-bromocinnoline-3-carboxamide. ¹H NMR (500 MHz, CD₃OD) δ ppm 7.18 (dd, J=8.30, 1.46 Hz, 1 H), 7.69 (s, 1 H), 8.02-8.10 (m, 3 H), 8.24 (d, J=0.98 Hz, 1 H), 8.54 (d, J=9.28 Hz, 1H); ESI-MS m/z [M+H]⁺ 305.1.

Example 60

4-amino-5-fluoro-8-(1H-indazol-5-yl)-7-methylcinnoline-3-carboxamide

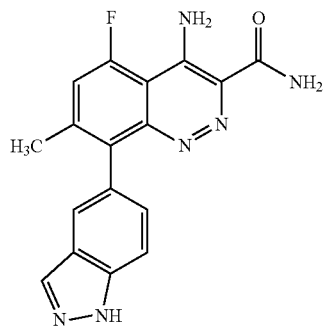 [SMILES: Cc1cc(F)c2c(N)c(C(N)=O)nnc2c1-c1ccc2[nH]ncc2c1]

The title compound was prepared in a manner similar to EXAMPLE 1 using (1H-indazol-5-yl)boronic acid and 4-amino-8-bromo-5-fluoro-7-methylcinnoline-3-carboxamide. ¹H NMR (400 MHz, CD₃OD) δ ppm 2.28 (s, 3 H), 7.19-7.30 (m, 1 H), 7.35 (d, J=16 Hz, 1H), 7.59-7.70 (m, 2 H), 8.07 (s, 1 H); ESI-MS m/z [M+H]⁺ 337.2.

Example 61

4-amino-7-ethyl-8-(1H-indazol-6-yl)cinnoline-3-carboxamide

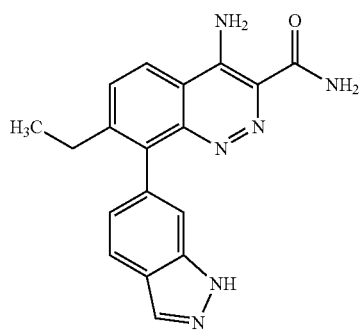 [SMILES: CCc1ccc2c(N)c(C(N)=O)nnc2c1-c1ccc2cn[nH]c2c1]

The title compound was prepared in a manner similar to EXAMPLE 1 using 6-(4,4,5,5-tetramethyl-1,3,2-dioxaborolan-2-yl)-1H-indazole and 4-amino-8-bromo-7-ethylcinnoline-3-carboxamide. ESI-MS m/z [M+H]$^+$ 333.

Example 62

4-amino-7-ethyl-8-(1H-indazol-5-yl)cinnoline-3-carboxamide

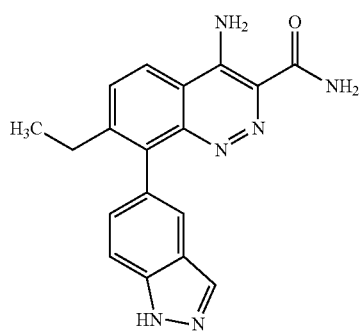 [SMILES: CCc1ccc2c(N)c(C(N)=O)nnc2c1-c1ccc2[nH]ncc2c1]

The title compound was prepared in a manner similar to EXAMPLE 1 using 5-(4,4,5,5-tetramethyl-1,3,2-dioxaborolan-2-yl)-1H-indazole and 4-amino-8-bromo-7-ethylcinnoline-3-carboxamide. ESI-MS m/z [M+H]$^+$ 333.

Example 63

4-amino-7-methyl-8-(1-oxo-1,2,3,4-tetrahydroisoquinolin-6-yl)cinnoline-3-carboxamide

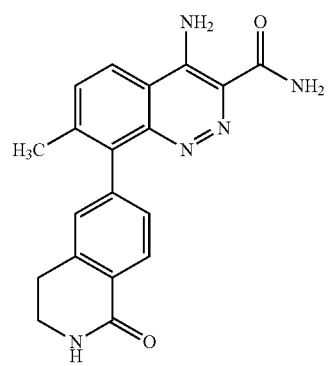 [SMILES: Cc1ccc2c(N)c(C(N)=O)nnc2c1-c1ccc2c(c1)CCNC2=O]

A TFA salt of the title compound was prepared in a manner similar to EXAMPLE 1 using (1-oxo-1,2,3,4-tetrahydroisoquinolin-6-yl)boronic acid and 4-amino-8-bromo-7-methylcinnoline-3-carboxamide. $^1$H NMR (400 MHz, CD$_3$OD) δ ppm 2.35 (s, 3 H), 3.12 (t, J=6.44 Hz, 2 H), 3.61 (t, J=6.57 Hz, 2 H), 7.27-7.57 (m, 2 H), 7.89 (d, J=8.84 Hz, 1 H), 8.21 (d, J=7.83 Hz, 1 H), 8.47 (d, J=8.59 Hz, 1 H); ESI-MS m/z [M+H]$^+$ 348.2.

Example 64

4-amino-6-methyl-8-(5-methyl-1H-indazol-6-yl)cinnoline-3-carboxamide

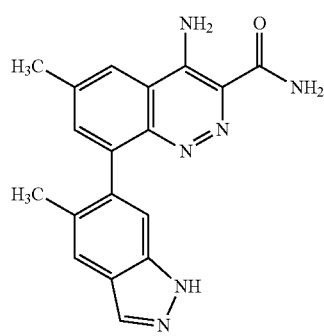 [SMILES: Cc1cc(-c2cc3[nH]ncc3cc2C)c2nnc(C(N)=O)c(N)c2c1]

A TFA salt of the title compound was prepared in a manner similar to EXAMPLE 1 using 5-methyl-6-(4,4,5,5-tetramethyl-1,3,2-dioxaborolan-2-yl)-1H-indazole and 4-amino-8-bromo-6-methylcinnoline-3-carboxamide. $^1$H NMR (500 MHz, DMSO-d$_6$) δ ppm 2.02 (s, 3H), 2.59 (s, 3 H), 7.41 (s, 1 H), 7.66-7.75 (m, 2 H), 7.83 (br s, 1 H), 8.07 (s, 1 H), 8.26 (br s, 1 H), 8.40 (br s, 1 H); ESI-MS m/z [M+H]$^+$ 333.4.

Example 65

4-amino-8-(2-((cyclopropylmethyl)amino)-1H-benzo[d]imidazol-6-yl)cinnoline-3-carboxamide

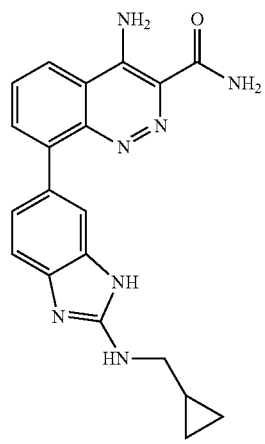 [SMILES: NC(=O)c1nnc2c(-c3ccc4nc(NCC5CC5)[nH]c4c3)cccc2c1N]

77

Step A: N-(cyclopropylmethyl)-5-(4,4,5,5-tetramethyl-1,3,2-dioxaborolan-2-yl)-1H-benzo[d]imidazol-2-amine

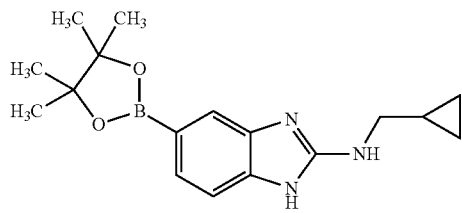 [SMILES: CC1(C)OB(c2ccc3[nH]c(NCC4CC4)nc3c2)OC1(C)C]

Cyclopropylmethyl isothiocyanate (0.104 mL, 1.068 mmol), 4-(4,4,5,5-tetramethyl-1,3,2-dioxaborolan-2-yl)benzene-1,2-diamine (250 mg, 1.068 mmol) and PS-carbodiimide (Biotage lot 03514 Technologies, 1.3 mmol/g, 1.4 g, 2.0 mmol) were suspended in anhydrous THF (10 mL). The reaction mixture was heated at 70° C. overnight. The mixture was subsequently cooled to RT and filtered. The solids were washed with MeOH (3×10 mL) and the filtrate was concentrated. The resulting solid was suspended in MeOH and filtered again. The filtrate was purified by preparative HPLC (Sunfire Prep 5 μm C18, 75×30 mm column) eluting with a gradient of 33-60% ACN (containing 0.035% TFA) in water (containing 0.05% TFA). The pure fractions were collected, evaporated to a minimal volume, and lyophilized to give a TFA salt of the title compound, which was used without further purification (26 mg, 7.8%). ESI-MS m/z [M+H]$^+$ 314.3.

Step B: 4-amino-8-(2-((cyclopropylmethyl)amino)-1H-benzo[d]imidazol-6-yl)cinnoline-3-carboxamide To a mixture of 4-amino-8-bromocinnoline-3-carboxamide hydrochloride (0.036 g, 0.120 mmol) and N-(cyclopropylmethyl)-5-(4,4,5,5-tetramethyl-1,3,2-dioxaborolan-2-yl)-1H-benzo[d]imidazol-2-amine (33A) (0.025 g, 0.080 mmol) suspended in dioxane (9 mL) were added PdCl$_2$(dppf) (5.84 mg, 7.98 μmol) and 2M Na$_2$CO$_3$ (0.080 mL, 0.160 mmol). The reaction mixture was purged with N$_2$ and heated in a microwave reactor at 140° C. for 45 minutes. The reaction mixture was subsequently filtered and concentrated. The residue was taken up in MeOH (5 mL) and filtered. The filtrate was purified by preparative HPLC (Sunfire Prep 5 μm C18, 75×30 mm column) eluting with a gradient of 15-40% ACN (containing 0.035% TFA) in water (containing 0.05% TFA). The pure fractions were collected and evaporated to give a TFA salt of the title compound (10 mg, 37%). ESI-MS m/z [M+H]$^+$ 374.3; $^1$H NMR (400 MHz, CD$_3$OD) δ ppm 0.36-0.45 (m, 2 H), 0.63-0.73 (m, 2 H), 1.20-1.27 (m, 1 H), 3.34-3.40 (m, 2 H), 7.48 (d, J=9.60 Hz, 1 H), 7.54-7.63 (m, 2 H), 7.92-8.00 (m, 1 H), 8.01-8.07 (m, 1 H), 8.55 (d, J=7.33 Hz, 1 H).

78

Example 66

4-amino-8-(2-neopentyl-1H-benzo[d]imidazol-6-yl)cinnoline-3-carboxamide

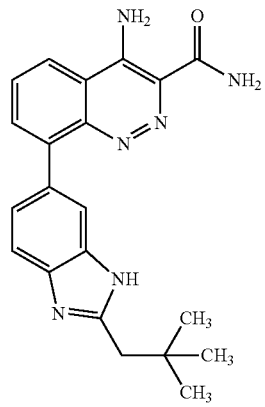 [SMILES: CC(C)(C)Cc1nc2ccc(-c3cccc4c(N)c(C(N)=O)nnc34)cc2[nH]1]

Step A: 4-amino-8-(3,4-diaminophenyl)cinnoline-3-carboxamide

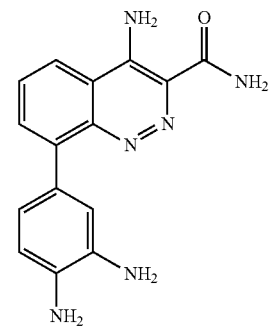 [SMILES: NC(=O)c1nnc2c(-c3ccc(N)c(N)c3)cccc2c1N]

To a mixture of 4-amino-8-bromocinnoline-3-carboxamide hydrochloride (0.280 g, 0.922 mmol), 4-(4,4,5,5-tetramethyl-1,3,2-dioxaborolan-2-yl)benzene-1,2-diamine (0.259 g, 1.107 mmol) and 2M Na$_2$CO$_3$ (0.232 g, 2.77 mmol) suspended in a dioxane/water mixture (10 mL; 9:1) was added PdCl$_2$(dppf) (0.075 g, 0.092 mmol). The reaction mixture was heated in a microwave reactor at 140° C. for 1 hour and was subsequently diluted with of EtOAc (5 mL), passed through a Celite pad, rinsed with additional EtOAc, and concentrated in vacuo. The residue was taken up in MeOH and purified by preparative HPLC (Sunfire Prep 5 μm C18, 75×30 mm column) eluting with a gradient of 15-40% ACN (containing 0.035% TFA) in water (containing 0.05% TFA). The pure fractions were collected and evaporated to give a TFA salt of the title compound as a yellow-glassy solid, which was used without further purification.

Step B: 4-amino-8-(2-neopentyl-1H-benzo[d]imidazol-6-yl)cinnoline-3-carboxamide 4-Amino-8-(3,4-diaminophenyl)cinnoline-3-carboxamide (0.05 g, 0.170 mmol), 3,3-dimethylbutanal (0.017 g, 0.170 mmol), and 4-methylbenzenesulfonic acid (0.012 g, 0.068 mmol) in DMF (2 mL) were combined and heated at 100° C. for 1 h in a microwave reactor. The crude reaction mixture was taken up in MeOH and purified by preparative HPLC (Sunfire Prep 5 μm C18, 75×30 mm column) eluting with a gradient of 10-20% ACN (containing 0.035% TFA) in water (containing 0.05% TFA). The pure fractions were collected and evaporated to give a TFA salt of the title compound as a clear film (5 mg, 8%). $^1$H NMR (400 MHz, CD$_3$OD) δ ppm 1.15 (s, 9 H), 3.12 (s, 2 H), 7.77 (dd, J=8.34, 1.52 Hz, 1 H), 7.91-8.12 (m, 4 H), 8.57 (dd, J=8.59, 1.26 Hz, 1 H); ESI-MS m/z [M+H]$^+$ 375.3.

Example 67

4-amino-8-(2-(3,5-dichlorophenyl)-1H-benzo[d]imidazol-6-yl)cinnoline-3-carboxamide

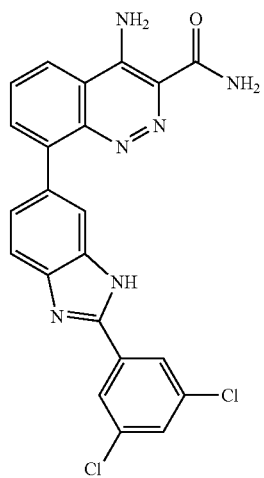 [SMILES: NC(=O)c1nnc2c(-c3ccc4nc(-c5cc(Cl)cc(Cl)c5)[nH]c4c3)cccc2c1N]

A TFA salt of the title compound was prepared in a manner similar to EXAMPLE 66 using 4-amino-8-bromocinnoline-3-carboxamide and 3,5-dichlorobenzaldehyde. $^1$H NMR (400 MHz, CD$_3$OD) δ ppm 7.55 (m 1 H), 7.70 (t, J=1.77 Hz, 1 H), 7.91 (m, 2 H), 7.98 (m, 1H), 8.10 (m, 1 H), 8.16 (d, J=4 Hz, 2 H), 8.55 (dd, 1 H); ESI-MS m/z [M+H]$^+$ 449.2.

Example 68

4-amino-8-(2-cyclohexyl-1H-benzo[d]imidazol-6-yl)cinnoline-3-carboxamide

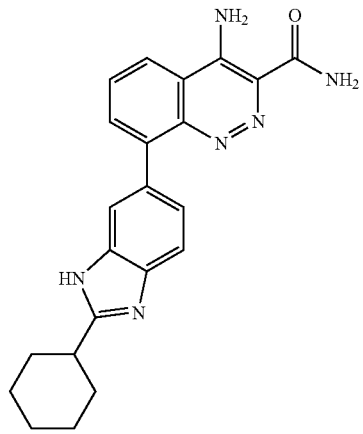 [SMILES: NC(=O)c1nnc2c(-c3ccc4nc(C5CCCCC5)[nH]c4c3)cccc2c1N]

The title compound was prepared in a manner similar to EXAMPLE 66 using 4-amino-8-bromocinnoline-3-carboxamide and cyclohexanecarbaldehyde. $^1$H NMR (400 MHz, CD$_3$OD) δ ppm 1.34-1.58 (m, 3 H), 1.59-1.85 (m, 3 H), 1.92 (d, J=12 Hz, 2 H), 2.12 (d, J=1 Hz, 2 H), 2.89-3.02 (m, 1 H), 7.46 (m, 1 H), 7.63 (d, J=8 Hz, 1 H), 7.72-7.84 (m, 2 H), 7.84-7.90 (m, 1 H), 8.27 (m, 1 H); ESI-MS m/z [(M+2H)/2]$^+$ 194.1.

Example 69

4-amino-8-(2-phenethyl-1H-benzo[d]imidazol-6-yl)cinnoline-3-carboxamide

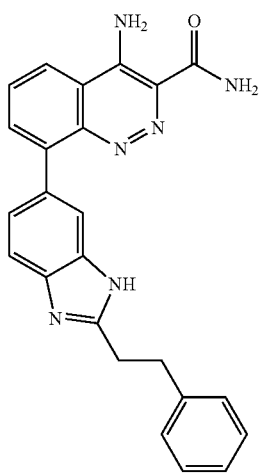 [SMILES: NC(=O)c1nnc2c(-c3ccc4nc(CCc5ccccc5)[nH]c4c3)cccc2c1N]

The title compound was prepared in a manner similar to EXAMPLE 66 using 4-amino-8-bromocinnoline-3-carboxamide and 3-phenylpropanal. $^1$H NMR (400 MHz, CD$_3$OD) δ ppm 2.37 (s, 2 H), 2.65 (s, 2 H), 7.80 (s, 1 H), 7.82 (s, 1 H), 7.83-7.92 (m, 2 H), 7.95-8.02 (m, 2 H), 8.12 (d, J=8 Hz, 2 H), 8.17 (s, 1 H), 8.60 (m, 1 H); ESI-MS m/z [(M+2H)/2]$^+$ 205.1.

Example 70

4-amino-8-(2-(2-chlorophenyl)-1H-benzo[d]imidazol-6-yl)cinnoline-3-carboxamide

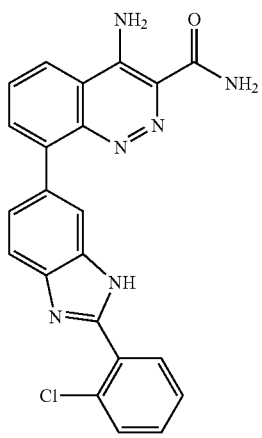 [SMILES: NC(=O)c1nnc2c(-c3ccc4nc(-c5ccccc5Cl)[nH]c4c3)cccc2c1N]

A TFA salt of the title compound was prepared in a manner similar to EXAMPLE 66 using 4-amino-8-bromocinnoline-3-carboxamide and 2-chlorobenzaldehyde. $^1$H NMR (400 MHz, CD$_3$OD) δ ppm 7.80 (s, 1 H), 7.82 (s, 1 H), 7.83-7.92 (m, 2 H), 7.95-8.02 (m, 2 H), 8.12 (d, J=8 Hz, 2 H), 8.17 (s, 1 H), 8.60 (m, 1 H); ESI-MS m/z [(M+2H)/2]$^+$ 208.2.

Example 71

4-amino-8-(2-(3-(trifluoromethyl)phenyl)-1H-benzo[d]imidazol-6-yl)cinnoline-3-carboxamide

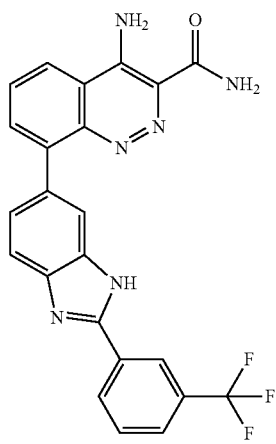 [SMILES: NC(=O)c1nnc2c(-c3ccc4nc(-c5cccc(C(F)(F)F)c5)[nH]c4c3)cccc2c1N]

A TFA salt of the title compound was prepared in a manner similar to EXAMPLE 66 using 4-amino-8-bromocinnoline-3-carboxamide and 3-(trifluoromethyl)benzaldehyde. ESI-MS m/z [M+H]$^+$ 449.3.

Example 72

4-amino-8-(2-cyclopentyl-1H-benzo[d]imidazol-6-yl)cinnoline-3-carboxamide

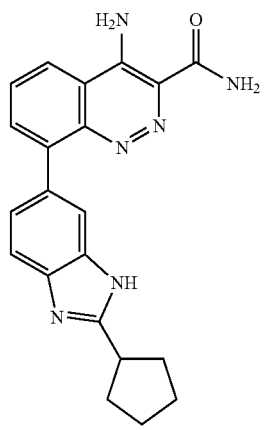 [SMILES: NC(=O)c1nnc2c(-c3ccc4nc(C5CCCC5)[nH]c4c3)cccc2c1N]

A TFA salt of the title compound was prepared in a manner similar to EXAMPLE 66 using 4-amino-8-bromocinnoline-3-carboxamide and cyclopentanecarbaldehyde. ESI-MS m/z [M+H]$^+$ 373.3.

Example 73

4-amino-8-(2-(thiophen-3-yl)-1H-benzo[d]imidazol-6-yl)cinnoline-3-carboxamide

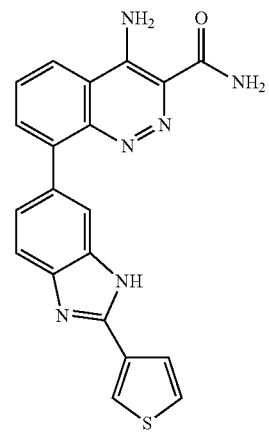 [SMILES: NC(=O)c1nnc2c(-c3ccc4nc(-c5ccsc5)[nH]c4c3)cccc2c1N]

A TFA salt of the title compound was prepared in a manner similar to EXAMPLE 66 using 4-amino-8-bromocinnoline-3-carboxamide and thiophene-3-carbaldehyde. ESI-MS m/z [M+H]$^+$ 387.2.

Example 74

4-amino-8-(2-(4-methoxyphenyl)-1H-benzo[d]imidazol-6-yl)cinnoline-3-carboxamide

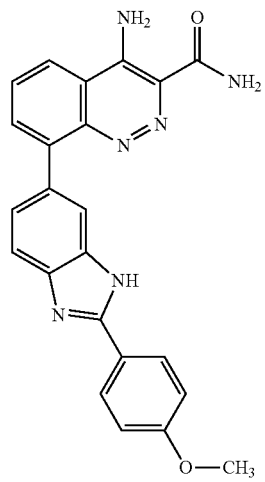 [SMILES: COc1ccc(-c2nc3ccc(-c4cccc5c(N)c(C(N)=O)nnc45)cc3[nH]2)cc1]

The title compound was prepared in a manner similar to EXAMPLE 66 using 4-amino-8-bromocinnoline-3-carboxamide and 4-methoxybenzaldehyde. ESI-MS m/z [(M+2H)/2]⁺ 206.2.

Example 75

4-amino-8-(2-(imidazo[1,2-a]pyridin-2-yl)-1H-benzo[d]imidazol-6-yl)cinnoline-3-carboxamide

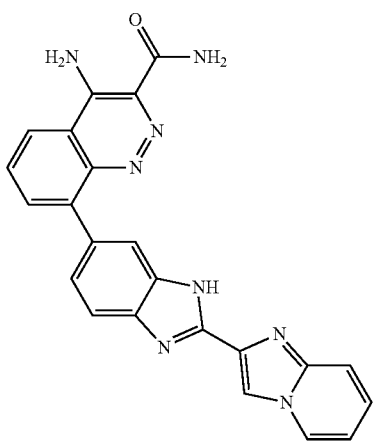 [SMILES: NC(=O)c1nnc2c(-c3ccc4nc(-c5cn6ccccc6n5)[nH]c4c3)cccc2c1N]

The title compound was prepared in a manner similar to EXAMPLE 66 using 4-amino-8-bromocinnoline-3-carboxamide and imidazo[1,2-a]pyridine-2-carbaldehyde. ESI-MS m/z [(M+2H)/2]⁺ 211.1.

Example 76

4-amino-8-(2-(3-chlorophenyl)-1H-benzo[d]imidazol-6-yl)cinnoline-3-carboxamide

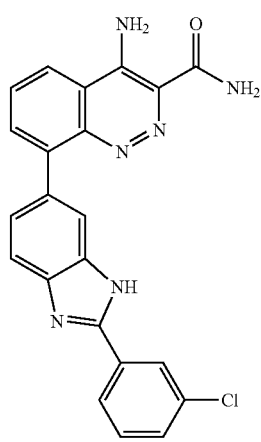 [SMILES: NC(=O)c1nnc2c(-c3ccc4nc(-c5cccc(Cl)c5)[nH]c4c3)cccc2c1N]

A TFA salt of the title compound was prepared in a manner similar to EXAMPLE 66 using 4-amino-8-bromocinnoline-3-carboxamide and 3-chlorobenzaldehyde. ¹H NMR (400 MHz, CD₃OD) δ ppm 7.55 (d, J=8 Hz, 1 H), 7.61 (d, J=4 Hz, 2 H), 7.86-7.92 (m, 2 H), 7.97 (m, 1 H), 8.05-8.13 (m, 2 H), 8.21 (s, 1 H), 8.53 (d, J=8 Hz, 1 H); ESI-MS m/z [M+H]⁺ 415.2.

Example 77

4-amino-8-(2-benzyl-1H-benzo[d]imidazol-6-yl)cinnoline-3-carboxamide

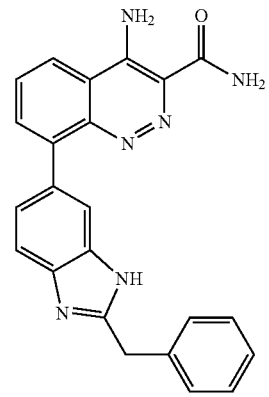 [SMILES: NC(=O)c1nnc2c(-c3ccc4nc(Cc5ccccc5)[nH]c4c3)cccc2c1N]

A TFA salt of the title compound was prepared in a manner similar to EXAMPLE 66 using 4-amino-8-bromocinnoline-3-carboxamide and 2-phenylacetaldehyde. ¹H NMR (400 MHz, CD₃OD) δ ppm 5.35 (s, 2 H), 7.87-7.97 (m, 1 H), 8.13-8.22 (m, 1 H), 8.22-8.34 (m, 3 H), 8.51-8.63 (m, 1 H), 8.66 (t, J=8.34 Hz, 1 H), 8.72-8.81 (m, 1 H), 8.83 (s, 1H), 9.23-9.36 (m, 2 H); ESI-MS m/z [M+H]⁺ 395.2.

Example 78

4-amino-8-(2-(cyclohexylmethyl)-1H-benzo[d]imidazol-6-yl)cinnoline-3-carboxamide

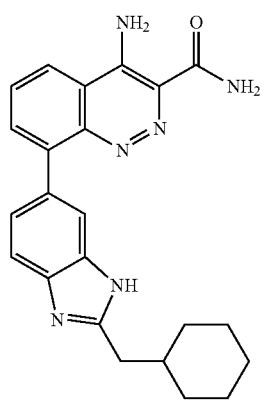 [SMILES: NC(=O)c1nnc2c(-c3ccc4nc(CC5CCCCC5)[nH]c4c3)cccc2c1N]

A TFA salt of the title compound was prepared in a manner similar to EXAMPLE 66 using 4-amino-8-bromocinnoline-3-carboxamide and 2-cyclohexylacetaldehyde. ¹H NMR (400 MHz, CD₃OD) δ ppm 1.13-1.43 (m, 4 H), 1.72 1.75-1.87 (m, 4 H), 3.15 (d, J=8 Hz, 2 H), 7.77 (d, J=8 Hz, 1 H), 7.90-8.06 (m, 3 H), 8.10 (d, J=8 Hz, 1 H), 8.60 (d, J=12 Hz, 1 H); ESI-MS m/z [M+H]⁺ 401.4.

Example 79

4-amino-8-(2-(thiophen-2-yl)-1H-benzo[d]imidazol-6-yl)cinnoline-3-carboxamide

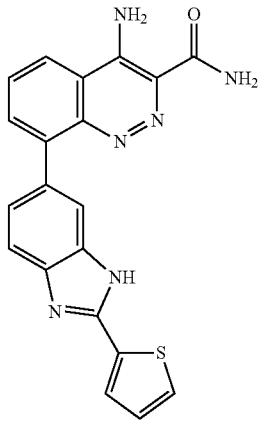 [SMILES: NC(=O)c1nnc2c(-c3ccc4nc(-c5cccs5)[nH]c4c3)cccc2c1N]

A TFA salt of the title compound was prepared in a manner similar to EXAMPLE 66 using 4-amino-8-bromocinnoline-3-carboxamide and thiophene-2-carbaldehyde. ¹H NMR (400 MHz, CD₃OD) δ ppm 7.45 (dd, J=8, 4 Hz, 1 H), 7.74 (d, J=12 Hz, 1 H), 7.96-8.06 (m, 3 H), 8.06-8.16 (m, 2 H), 8.20 (d, J=4 Hz, 1 H), 8.61 (d, J=8 Hz, 1 H); ESI-MS m/z [M+H]⁺ 387.2.

Example 80

4-amino-8-(2-(3,5-dimethylphenyl)-1H-benzo[d]imidazol-6-yl)cinnoline-3-carboxamide

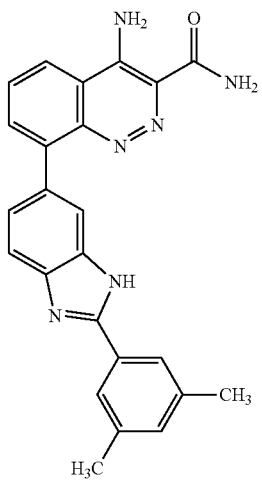 [SMILES: Cc1cc(C)cc(-c2nc3ccc(-c4cccc5c(N)c(C(N)=O)nnc45)cc3[nH]2)c1]

A TFA salt of the title compound was prepared in a manner similar to EXAMPLE 66 using 4-amino-8-bromocinnoline-3-carboxamide and 3,5-dimethylbenzaldehyde. ¹H NMR (400 MHz, CD₃OD) δ ppm 2.04 (s, 6 H), 7.09 (s, 1 H), 7.41

(s, 1 H), 7.71 (d, J=12 Hz, 1 H), 7.82 (s, 2 H), 7.90-8.01 (m, 2 H), 8.08 (d, J=8 Hz, 1 H), 8.55 (d, J=8 Hz, 1 H); ESI-MS m/z [M+H]⁺ 409.2.

Example 81

4-amino-8-(2-((tetrahydro-2H-pyran-4-yl)methyl)-1H-benzo[d]imidazol-6-yl)cinnoline-3-carboxamide

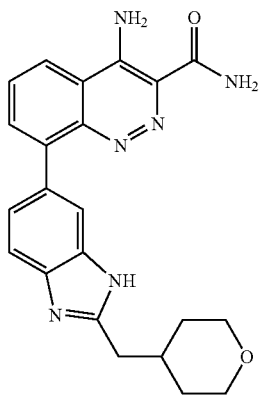 [SMILES: NC(=O)c1nnc2c(-c3ccc4nc(CC5CCOCC5)[nH]c4c3)cccc2c1N]

A TFA salt of the title compound was prepared in a manner similar to EXAMPLE 66 using 4-amino-8-bromocinnoline-3-carboxamide and 2-phenylacetaldehyde. ¹H NMR (400 MHz, CD₃OD) δ ppm 1.38-1.59 (m, 2 H), 1.68 (dd, J=12.88, 1.77 Hz, 2 H), 2.18-2.33 (m, 1 H), 3.21 (d, J=7.33 Hz, 2 H), 3.46 (td, J=11.81, 1.89 Hz, 2 H), 3.98 (dd, J=11.62, 3.03 Hz, 2 H), 7.23 (d, J=7.83 Hz, 1 H), 7.69 (d, J=8.08 Hz, 1 H), 7.77 (dd, J=8.46, 1.64 Hz, 1 H), 7.91-8.05 (m, 3 H), 8.09 (dd, J=7.07, 1.26 Hz, 1 H), 8.59 (dd, J=8.59, 1.26 Hz, 1 H); ESI-MS m/z [M+H]⁺ 403.2.

Example 82

4-amino-8-(2-(thiazol-5-yl)-1H-benzo[d]imidazol-6-yl)cinnoline-3-carboxamide

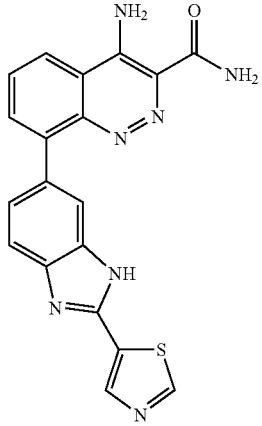 [SMILES: NC(=O)c1nnc2c(-c3ccc4nc(-c5cncs5)[nH]c4c3)cccc2c1N]

A TFA salt of the title compound was prepared in a manner similar to EXAMPLE 66 using 4-amino-8-bromocinnoline-3-carboxamide and thiazole-5-carbaldehyde. ¹H NMR (400 MHz, CD₃OD) δ ppm 7.47-7.60 (m, 1 H), 7.82-7.93 (m, 2 H), 7.94-8.06 (m, 1 H), 8.10 (d, J=6.32 Hz, 1 H), 8.55 (d, J=8.59 Hz, 1 H), 8.62 (s, 1 H), 9.24 (s, 1 H); ESI-MS m/z [M+H]+ 388.18.

Example 83

4-amino-8-(2-(tetrahydro-2H-pyran-3-yl)-1H-benzo[d]imidazol-6-yl)cinnoline-3-carboxamide

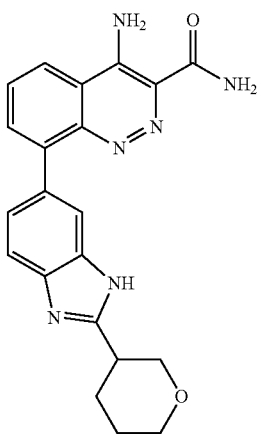 [SMILES: NC(=O)c1nnc2c(-c3ccc4nc(C5CCCOC5)[nH]c4c3)cccc2c1N]

A TFA salt of the title compound was prepared in a manner similar to EXAMPLE 66 using tetrahydro-2H-pyran-3-carbaldehyde and 4-amino-8-bromocinnoline-3-carboxamide. ESI-MS m/z [M+H]+ 389.3.

Example 84

4-amino-8-(2-(4,4-difluorocyclohexyl)-1H-benzo[d]imidazol-6-yl)cinnoline-3-carboxamide

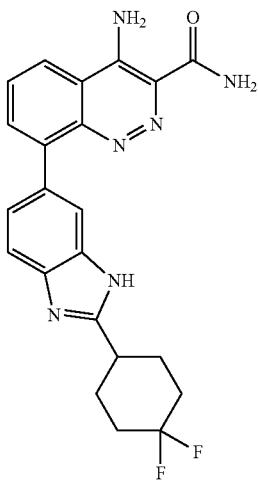 [SMILES: NC(=O)c1nnc2c(-c3ccc4nc(C5CCC(F)(F)CC5)[nH]c4c3)cccc2c1N]

A TFA salt of the title compound was prepared in a manner similar to EXAMPLE 66 using 4,4difluorocyclohexanecarbaldehyde and 4-amino-8-bromocinnoline-3-carboxamide. ESI-MS m/z [M+H]+ 423.4.

Example 85

4-amino-8-(4,5-dihydro-1H-pyrazolo[3,4-c]pyridin-6(7H)-yl)cinnoline-3-carboxamide

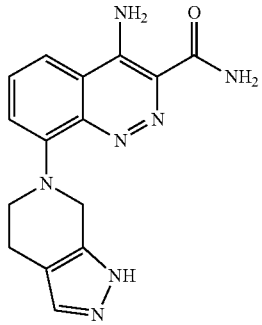 [SMILES: NC(=O)c1nnc2c(N3CCc4cn[nH]c4C3)cccc2c1N]

A mixture of 4-amino-8-fluorocinnoline-3-carboxamide hydrochloride (40 mg, 0.165 mmol), 4,5,6,7-tetrahydro-1H-pyrazolo[3,4-c]pyridine dihydrochloride (162 mg, 0.824 mmol), and 4-methylmorpholine (0.362 mL, 3.30 mmol) suspended in water (0.1 mL) was heated at 160° C. for 1 hour in a microwave reactor. The crude reaction mixture was subsequently purified by preparative HPLC (Sunfire Prep 5 μm C18, 75×30 mm column) eluting with a gradient of 5-30% ACN (containing 0.035% TFA) in water (containing 0.05% TFA). The pure fractions were collected and dried in vacuo to afford a TFA salt of the title compound as a yellow oil (2.4 mg, 4.7%). $^1$H NMR (500 MHz, CD$_3$OD) δ ppm 3.11-3.18 (m, 2 H), 3.44 (dt, J=3.30, 1.53 Hz, 2 H), 3.55 (t, J=5.86 Hz, 2 H), 7.49 (s, 1 H), 7.79-7.85 (m, 1 H), 7.87-7.92 (m, 1 H), 8.22 (d, J=8.30 Hz, 1 H); ESI-MS m/z [M+H]+ found 310.5.

Example 86

4-amino-8-(6,7-dihydro-1H-pyrazolo[4,3-c]pyridin-5(4H)-yl)cinnoline-3-carboxamide

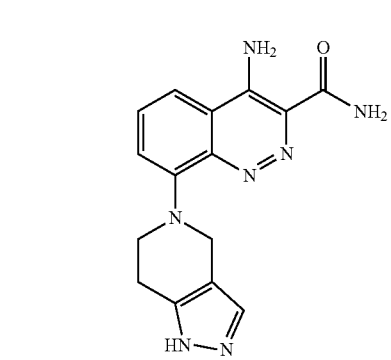 [SMILES: NC(=O)c1nnc2c(N3CCc4[nH]ncc4C3)cccc2c1N]

A TFA salt of the title compound was prepared in a manner similar to EXAMPLE 85 using 4,5,6,7-tetrahydro-1H-pyrazolo[4,3-c]pyridine dihydrochloride in place of 4,5,6,7-tetrahydro-1H-pyrazolo[3,4-c]pyridine dihydrochloride. $^1$H NMR (500 MHz, CD$_3$OD) δ ppm 3.11-3.18 (m, 2 H), 3.44 (dt, J=3.30, 1.53 Hz, 2 H), 3.55 (t, J=5.86 Hz, 2 H), 7.49 (s, 1 H), 7.79-7.85 (m, 1 H), 7.87-7.92 (m, 1 H), 8.22 (d, J=8.30 Hz, 1 H); ESI-MS m/z [M+H]+ 310.5

Example 87

4-amino-8-(2-(phenylamino)-1H-benzo[d]imidazol-6-yl)cinnoline-3-carboxamide

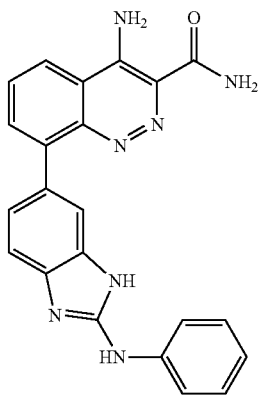 [SMILES: NC(=O)c1nnc2c(-c3ccc4nc(Nc5ccccc5)[nH]c4c3)cccc2c1N]

Step A: 2-chloro-6-(4,4,5,5-tetramethyl-1,3,2-dioxaborolan-2-yl)-1H-benzo[d]imidazole

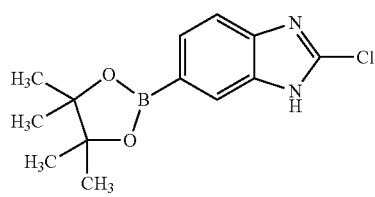 [SMILES: CC1(C)OB(c2ccc3nc(Cl)[nH]c3c2)OC1(C)C]

5-(4,4,5,5-Tetramethyl-1,3,2-dioxaborolan-2-yl)-1H-benzo[d]imidazol-2(3H)-one (1 g, 3.84 mmol) was dissolved in POCl$_3$ (5 mL, 53.6 mmol) under N$_2$. The mixture was heated at 100° C. for 2 hours and was subsequently cooled and concentrated to dryness to give the title compound as a purple solid, which was used without further purification (1.44 g).

Step B: N-phenyl-6-(4,4,5,5-tetramethyl-1,3,2-dioxaborolan-2-yl)-1H-benzo[d]imidazol-2-amine

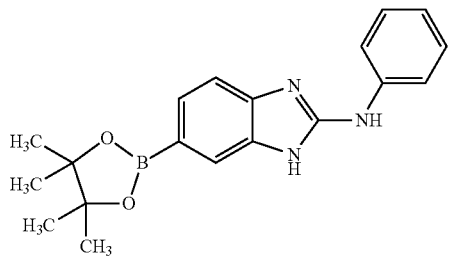 [SMILES: CC1(C)OB(c2ccc3nc(Nc4ccccc4)[nH]c3c2)OC1(C)C]

2-Chloro-6-(4,4,5,5-tetramethyl-1,3,2-dioxaborolan-2-yl)-1H-benzo[d]imidazole (200 mg, 0.718 mmol) and aniline (669 mg, 7.18 mmol) were mixed in N-methyl-2-pyrrolidinone (2 mL). The solution was heated at 140° C. for 30 minutes in a microwave reactor. The reaction mixture was concentrated to give the title compound, which was used without further purification.

Step C: 4-amino-8-(2-(phenylamino)-1H-benzo[d]imidazol-6-yl)cinnoline-3-carboxamide N-phenyl-6-(4,4,5,5-tetramethyl-1,3,2-dioxaborolan-2-yl)-1H-benzo[d]imidazol-2-amine (126 mg, 0.37 mmol) was added to 4-amino-8-bromocinnoline-3-carboxamide (100 mg, 0.374 mmol), Pd(dppf)CH$_2$Cl$_2$ adduct (306 mg, 0.374 mmol), and Na$_2$CO$_3$ (1.5 mL, 0.374 mmol) in dioxane (3 mL). The reaction mixture was heated at 120° C. for 30 minutes in a microwave reactor and then concentrated. The residue was purified by preparative HPLC (Sunfire Prep 5 μm C18, 75×30 mm column) eluting with a gradient of 5-30% ACN (containing 0.035% TFA) in water (containing 0.05% TFA). The pure fractions were collected and dried in vacuo to afford a TFA salt of the title compound as pale yellow solid (15 mg, 10%).

Example 88

4-amino-8-(2-(thiophen-2-ylmethylamino)-1H-benzo[d]imidazol-6-yl)cinnoline-3-carboxamide

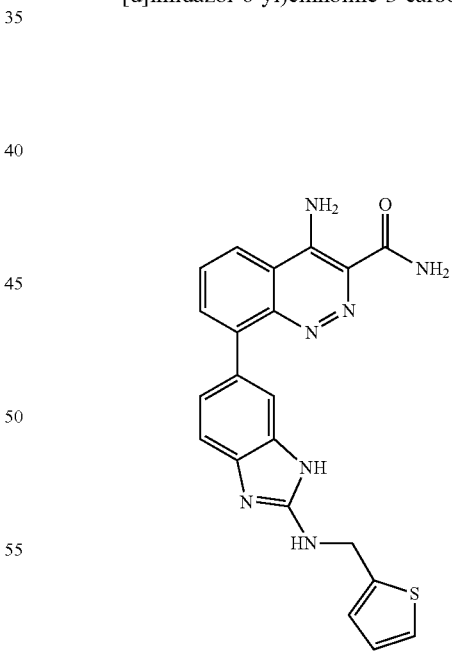

The title compound was prepared in a manner similar to EXAMPLE 87 using thiophen-2-ylmethanamine in place of aniline in Step B. $^1$H NMR (400 MHz, CD$_3$OD) δ ppm 6.97 (m, 1 H), 7.10 (d, J=4 Hz, 1 H), 7.23-7.33 (m, 2 H), 7.33-7.40 (m, 1 H), 7.50 (s, 1 H), 7.72-7.81 (m, 1 H), 7.84 (d, J=8 Hz, 1 H), 8.24 (d, J=8 Hz, 1 H); ESI-MS m/z [M+H]+ 416.3.

Example 89

4-amino-8-(2-(cyclobutylamino)-1H-benzo[d]imidazol-6-yl)cinnoline-3-carboxamide

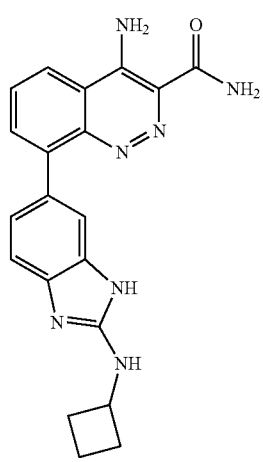 [SMILES: NC(=O)c1nnc2c(-c3ccc4nc(NC5CCC5)[nH]c4c3)cccc2c1N]

The title compound was prepared in a manner similar to EXAMPLE 87 using cyclobutanamine in place of aniline in Step B. ¹H NMR (400 MHz, CD₃OD) δ ppm 1.91 (br s, 2 H), 2.21 (br s, 2 H), 2.55 (br s, 2 H), 2.66 (s, 1 H), 7.50 (d, J=8 Hz, 1 H), 7.58 (d, J=12 Hz, 1 H), 7.85-7.95 (m, 1 H), 7.96-8.05 (m, 1 H), 8.49 (d, J=126 Hz, 2 H).

Example 90

4-amino-8-(2-(benzylamino)-1H-benzo[d]imidazol-6-yl)cinnoline-3-carboxamide

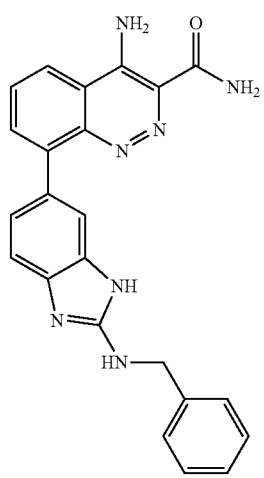 [SMILES: NC(=O)c1nnc2c(-c3ccc4nc(NCc5ccccc5)[nH]c4c3)cccc2c1N]

The title compound was prepared in a manner similar to EXAMPLE 87 using phenylmethanamine in place of aniline in Step B. ¹H NMR (400 MHz, CD₃OD) δ ppm 4.72 (s, 2 H), 7.30-7.54 (m, 6 H), 7.58-7.66 (m, 2 H), 7.96 (m, 1 H), 8.00-8.08 (m, 1 H), 8.55 (m, 1 H); ESI-MS m/z [(M+2H)/2]⁺ 205.7.

Example 91

4-amino-8-(2-(4-methylcyclohexylamino)-1H-benzo[d]imidazol-6-yl)cinnoline-3-carboxamide

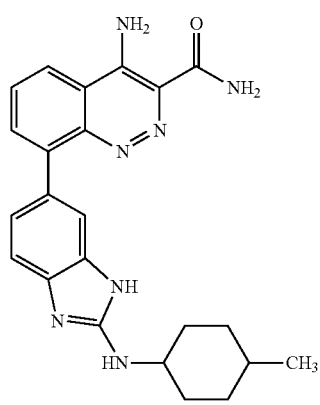 [SMILES: CC1CCC(Nc2nc3ccc(-c4cccc5c(N)c(C(N)=O)nnc45)cc3[nH]2)CC1]

The title compound was prepared in a manner similar to EXAMPLE 87 using 4-methylcyclohexanamine in place of aniline in Step B. ESI-MS m/z [(M+2H)/2]⁺ 208.6.

Example 92

4-amino-8-(2-(benzyl(methyl)amino)-1H-benzo[d]imidazol-6-yl)cinnoline-3-carboxamide

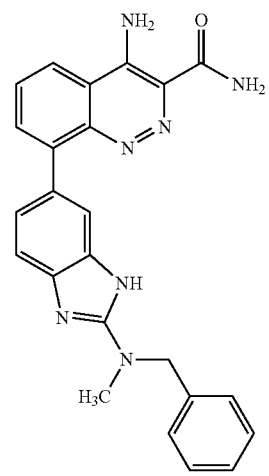 [SMILES: CN(Cc1ccccc1)c1nc2ccc(-c3cccc4c(N)c(C(N)=O)nnc34)cc2[nH]1]

A TFA salt of the title compound was prepared in a manner similar to EXAMPLE 87 using N-methyl-1-phenylmethanamine in place of aniline in Step B. ¹H NMR (400 MHz, CD₃OD) δ ppm 3.30 (s, 3 H), 4.90 (s, 2 H), 7.35-7.41 (m, 3 H), 7.41-7.47 (m, 2 H), 7.51 (d, J=8 Hz, 1 H), 7.58-7.66 (m, 2 H), 7.90-7.99 (m, 1 H), 8.04 (d, J=4 Hz, 1 H), 8.55 (d, J=8 Hz, 1 H); ESI-MS m/z [(M+2H)/2]⁺ 212.6.

Example 93

4-amino-8-(2-(cyclopentylmethylamino)-1H-benzo[d]imidazol-6-yl)cinnoline-3-carboxamide

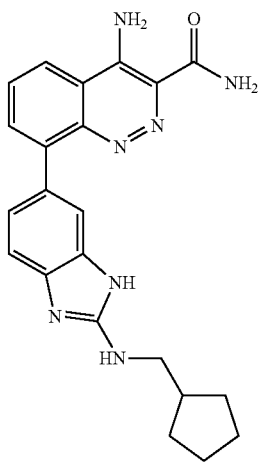 [SMILES: NC(=O)c1nnc2c(-c3ccc4nc(NCC5CCCC5)[nH]c4c3)cccc2c1N]

The title compound was prepared in a manner similar to EXAMPLE 87 using cyclopentylmethanamine in place of aniline in Step B. ¹H NMR (400 MHz, CD₃OD) δ ppm 1.17-1.46 (m, 2 H), 1.53-1.80 (m, 4 H), 1.80-2.02 (m, 2 H), 2.13-2.42 (m, 1 H), 3.37 (d, J=7.33 Hz, 2 H), 7.47 (s, 2 H), 7.59 (s, 1 H), 7.72-7.92 (m, 2 H), 8.31 (d, J=8.59 Hz, 1 H); ESI-MS m/z [(M+2H)/2]⁺ 201.6.

Example 94

8-(2-((adamantan-2-ylmethyl)amino)-1H-benzo[d]imidazol-6-yl)-4-aminocinnoline-3-carboxamide

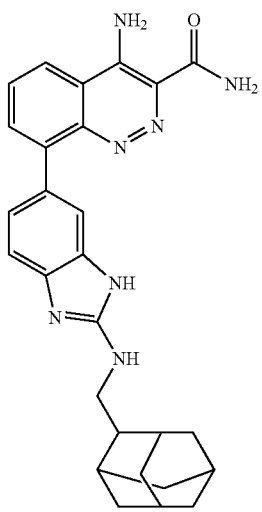 [SMILES: NC(=O)c1nnc2c(-c3ccc4nc(NCC5C6CC7CC(C6)CC5C7)[nH]c4c3)cccc2c1N]

The title compound was prepared in a manner similar to EXAMPLE 87 using adamantan-2-ylmethanamine in place of aniline in Step B. ¹H NMR (400 MHz, CD₃OD) δ ppm 1.29 (s, 1 H), 1.63 (d, J=16 Hz, 2 H), 1.75-1.89 (m, 4 H), 1.89-1.98 (m, 4 H), 1.98-2.06 (m, 2 H), 2.06-2.14 (m, 1 H), 3.54 (d, J=8 Hz, 2 H), 7.16-7.39 (m, 2 H), 7.48 (s, 1 H), 7.77 (m, 1 H), 7.84 (d, J=8 Hz, 1 H), 8.24 (d, J=8 Hz, 1 H); ESI-MS m/z [(M+2H)/2]⁺ 234.7.

Example 95

4-amino-8-(2-(4-methylbenzylamino)-1H-benzo[d]imidazol-6-yl)cinnoline-3-carboxamide

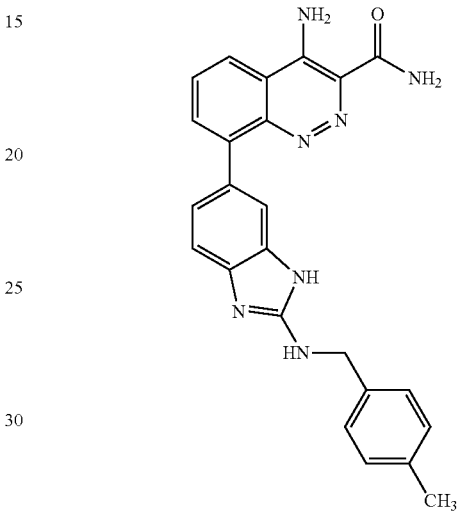

A TFA salt of the title compound was prepared in a manner similar to EXAMPLE 87 using p-tolylmethanamine in place of aniline in Step B. ¹H NMR (400 MHz, CD₃OD) δ ppm 2.35 (s, 3 H), 4.65 (s, 2 H), 7.24 (d, J=8 Hz, 2 H), 7.33 (d, J=8 Hz, 2 H), 7.44-7.54 (m, 1 H), 7.61 (s, 1 H), 7.57 (s, 1 H), 7.92 (t, J=8 Hz, 1 H), 8.00 (d, J=4 Hz, 1 H), 8.49 (d, J=8 Hz, 1 H); ESI-MS m/z [M+H]⁺ 424.3.

Example 96

4-amino-8-(3-cyano-1H-indazol-6-yl)-7-methylcinnoline-3-carboxamide

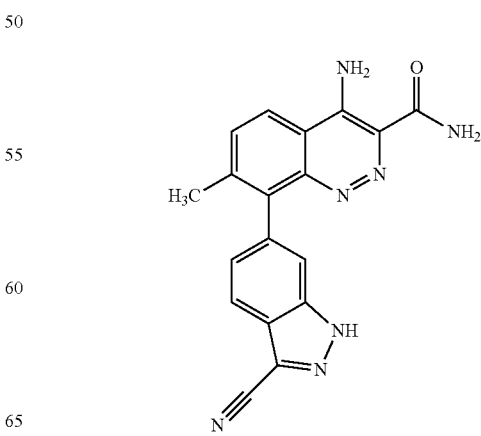

Step A: 5-(4,4,5,5-tetramethyl-1,3,2-dioxaborolan-2-yl)-1H-indazole-3-carbonitrile

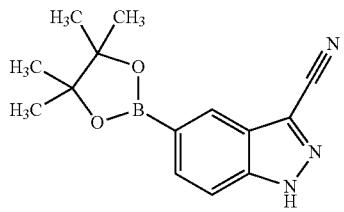 [SMILES: CC1(C)OB(c2ccc3[nH]nc(C#N)c3c2)OC1(C)C]

To a mixture of 5-bromo-1H-indazole-3-carbonitrile (475 mg, 2.139 mmol), 1,4-dioxane (15 mL), potassium acetate (735 mg, 7.49 mmol), and bis(pinacolato)diboron (652 mg, 2.57 mmol), was added PdCl$_2$(dppf) (78 mg, 0.107 mmol). The mixture was purged with N$_2$ and then heated at 90° C. for 16 hours. The mixture was subsequently cooled and purified by column chromatography, eluting with a gradient of MeOH (0-10%) in DCM. The relevant fractions were collected and concentrated to give the title compound as an off-white solid (120 mg, 20.8%).

Step B: 4-amino-8-(3-cyano-1H-indazol-6-yl)-7-methylcinnoline-3-carboxamide

To a vial containing 4-amino-8-bromo-7-methylcinnoline-3-carboxamide hydrochloride (30 mg, 0.094 mmol), 6-(4,4,5,5-tetramethyl-1,3,2-dioxaborolan-2-yl)-1H-indazole-3-carbonitrile (33.0 mg, 0.123 mmol), and NaHCO$_3$ (23.81 mg, 0.283 mmol) suspended in a dioxane/water mixture was added PdCl$_2$(dppf)CH$_2$Cl$_2$ adduct (7.71 mg, 9.45 μmol). The vial was capped and the reaction mixture was heated at 150° C. for 1 hour in a microwave reactor. The reaction mixture was subsequently cooled, diluted with EtOAc (5 mL), and passed through a Celite pad, which was rinsed with additional EtOAc. The filtrate was concentrated in vacuo and purified by preparative HPLC (Sunfire Prep 5 μm C18, 75×30 mm column) eluting with a gradient of 10-40% ACN (containing 0.035% TFA) in water (containing 0.05% TFA). The pure fractions were collected and dried in vacuo to afford a TFA salt of the title compound as a yellow solid (11 mg, 34%). $^1$H NMR (500 MHz, CD$_3$OD) δ ppm 2.34 (s, 3 H), 7.36 (dd, J=8.30, 1.46 Hz, 1 H), 7.80 (s, 1 H), 7.90 (d, J=8.79 Hz, 1 H), 8.12 (dd, J=8.30, 0.98 Hz, 1H), 8.47 (d, J=8.79 Hz, 1 H); ESI-MS m/z [M+H]$^+$ 344.4.

Example 97

4-amino-7-methyl-8-(1-methyl-1H-imidazo[4,5-b]pyridin-6-yl)cinnoline-3-carboxamide

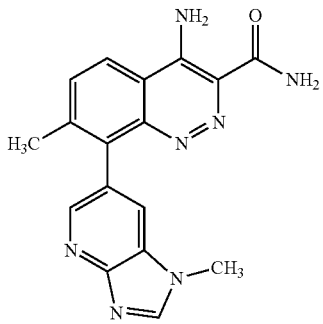 [SMILES: Cc1ccc2c(N)c(C(N)=O)nnc2c1-c1cnc2ncn(C)c2c1]

The title compound was prepared in a manner similar to EXAMPLE 96 using 6-bromo-1-methyl-1H-imidazo[4,5-b]pyridine and 4-amino-8-bromo-7-methylcinnoline-3-carboxamide. $^1$H NMR (400 MHz, CD$_3$OD) δ ppm 2.37 (s, 3 H), 3.98 (s, 3 H), 7.76 (d, J=9.09 Hz, 1 H), 8.09 (d, J=1.77 Hz, 1 H), 8.29 (d, J=8.59 Hz, 1 H), 8.39 (d, J=2.02 Hz, 1H), 8.47 (s, 1 H); ESI-MS m/z [M+H]$^+$ 334.2.

Example 98

4-amino-7-methyl-8-(3-methyl-3H-imidazo[4,5-b]pyridin-6-yl)cinnoline-3-carboxamide

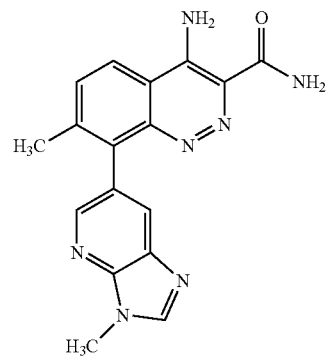 [SMILES: Cc1ccc2c(N)c(C(N)=O)nnc2c1-c1cnc2c(c1)ncn2C]

The title compound was prepared in a manner similar to EXAMPLE 96 using 6-bromo-3-methyl-3H-imidazo[4,5-b]pyridine and 4-amino-8-bromo-7-methylcinnoline-3-carboxamide. $^1$H NMR (400 MHz, CD$_3$OD) δ ppm 2.34 (s, 3 H), 4.03 (s, 3 H), 7.75 (d, J=8.59 Hz, 1 H), 8.04 (d, J=1.77 Hz, 1 H), 8.28 (d, J=8.59 Hz, 1 H), 8.35 (d, J=1.77 Hz, 1H), 8.45 (s, 1 H); ESI-MS m/z [M+H]$^+$ 334.2.

Example 99

4-amino-7-methyl-8-(3-methyl-1H-indazol-6-yl)cinnoline-3-carboxamide

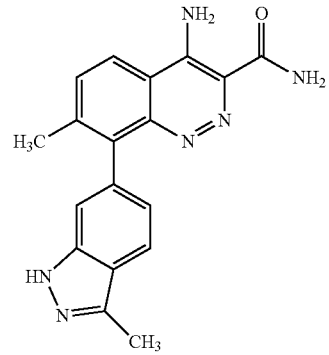 [SMILES: Cc1ccc2c(N)c(C(N)=O)nnc2c1-c1ccc2c(C)n[nH]c2c1]

A TFA salt of the title compound was prepared in a manner similar to EXAMPLE 96 using 6-bromo-3-methyl-1H-indazole and 4-amino-8-bromo-7-methylcinnoline-3-carboxamide. $^1$H NMR (500 MHz, DMSO-d$_6$) δ ppm 2.26 (s, 3 H), 2.57 (s, 3 H), 6.91-7.04 (m, 1 H), 7.40 (s, 1 H), 7.80-7.89 (m, 2 H), 7.99 (br s, 1 H), 8.14 (br s, 1 H), 8.54 (br s, 1 H), 12.79 (s, 1 H); ESI-MS m/z [M+H]⁺ 333.3.

Example 100

4-amino-8-(3-fluoro-1H-indazol-6-yl)-7-methylcinnoline-3-carboxamide

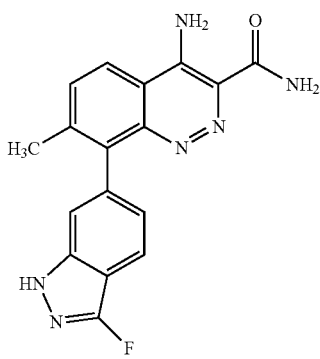 [SMILES: Cc1ccc2c(N)c(C(N)=O)nnc2c1-c1ccc2c(F)n[nH]c2c1]

A TFA salt of the title compound was prepared in a manner similar to EXAMPLE 96 using 6-bromo-3-fluoro-1H-indazole and 4-amino-8-bromo-7-methylcinnoline-3-carboxamide. ¹H NMR (500 MHz, DMSO-d₆) δ ppm 2.29 (s, 3 H), 7.09 (d, J=0.98 Hz, 1 H), 7.41 (s, 1 H), 7.53-7.94 (m, 3 H), 8.27 (br s, 1 H), 8.46 (br s, 1 H), 12.63 (br s, 1 H).

Example 101

4-amino-8-(4-fluoro-1H-benzo[d]imidazol-6-yl)-7-methylcinnoline-3-carboxamide

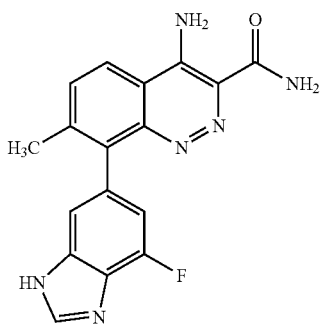 [SMILES: Cc1ccc2c(N)c(C(N)=O)nnc2c1-c1cc(F)c2nc[nH]c2c1]

A TFA salt of the title compound was prepared in a manner similar to EXAMPLE 96 using 5-bromo-7-fluoro-1H-benzo[d]imidazole and 4-amino-8-bromo-7-methylcinnoline-3-carboxamide. ¹H NMR (500 MHz, CD₃OD) δ ppm 2.37 (s, 3 H), 7.18 (d, J=10.25 Hz, 1 H), 7.56 (d, J=0.98 Hz, 1 H), 7.90 (d, J=8.79 Hz, 1 H), 8.48 (d, J=8.79 Hz, 1 H), 8.65 (s, 1 H); ESI-MS m/z [M+H]⁺ 337.4.

Example 102

4-amino-8-(4-fluoro-1H-indazol-6-yl)-7-methylcinnoline-3-carboxamide

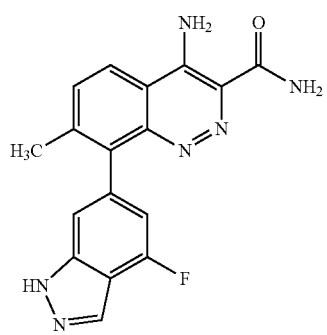 [SMILES: Cc1ccc2c(N)c(C(N)=O)nnc2c1-c1cc(F)c2cn[nH]c2c1]

A TFA salt of the title compound was prepared in a manner similar to EXAMPLE 96 using 6-bromo-4-fluoro-1H-indazole and 4-amino-8-bromo-7-methylcinnoline-3-carboxamide. ¹H NMR (500 MHz, CD₃OD) δ ppm 2.38 (s, 3 H), 6.88 (d, J=10.25 Hz, 1 H), 7.46 (s, 1 H), 7.89 (d, J=8.79 Hz, 1 H), 8.29 (s, 1 H), 8.47 (d, J=8.79 Hz, 1 H); ESI-MS m/z [M+H]⁺ 337.4.

Example 103

4-amino-8-(6-methoxy-1H-indazol-5-yl)cinnoline-3-carboxamide

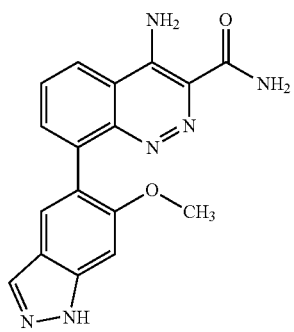 [SMILES: COc1cc2[nH]ncc2cc1-c1cccc2c(N)c(C(N)=O)nnc12]

A TFA salt of the title compound was prepared in a manner similar to EXAMPLE 96 using 5-bromo-6-methoxy-1H-indazole and 4-amino-8-bromocinnoline-3-carboxamide. ¹H NMR (500 MHz, CD₃OD) δ ppm 3.81 (s, 3 H), 7.24 (s, 1 H), 7.85 (s, 1 H), 7.93-7.97 (m, 1 H), 7.98-8.01 (m, 1 H), 8.08 (s, 1 H), 8.52 (dd, J=8.30, 1.46 Hz, 1 H); ESI-MS m/z [M+H]+ 335.4.

Example 104

4-amino-8-(7-fluoro-1H-indazol-6-yl)-7-methylcinnoline-3-carboxamide

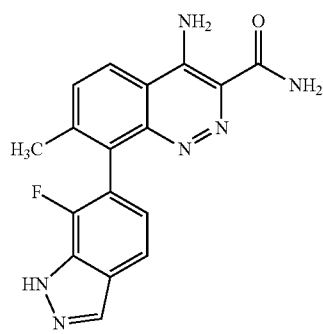 [SMILES: Cc1ccc2c(N)c(C(N)=O)nnc2c1-c1ccc2cn[nH]c2c1F]

A TFA salt of the title compound was prepared in a manner similar to EXAMPLE 96 using 6-bromo-7-fluoro-1H-indazole and 4-amino-8-bromo-7-methylcinnoline-3-carboxamide. $^1$H NMR (500 MHz, CD$_3$OD) δ ppm 2.39 (s, 3 H), 6.99-7.17 (m, 1 H), 7.87 (d, J=7.81 Hz, 1 H), 7.94 (d, J=8.79 Hz, 1 H), 8.26-8.34 (m, 1 H), 8.52 (d, J=8.79 Hz, 1 H); ESI-MS m/z [M+H]+ 337.4.

Example 105

4-amino-8-(5-chloro-1H-indazol-6-yl)cinnoline-3-carboxamide

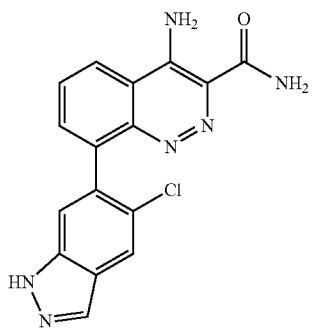 [SMILES: NC(=O)c1nnc2c(-c3cc4[nH]ncc4cc3Cl)cccc2c1N]

A TFA salt of the title compound was prepared in a manner similar to EXAMPLE 96 using 6-bromo-5-chloro-1H-indazole and 4-amino-8-bromocinnoline-3-carboxamide. $^1$H NMR (500 MHz, CD$_3$OD) δ ppm 7.70-7.80 (m, 1 H), 7.95-8.02 (m, 1 H), 8.02-8.08 (m, 1 H), 8.13 (d, J=2.44 Hz, 1 H), 8.17-8.24 (m, 1 H), 8.51-8.68 (m, 1 H); ESI-MS m/z [M+H]+ 339.3.

Example 106

4-amino-8-(3-cyclopropyl-1H-indazol-6-yl)-7-methylcinnoline-3-carboxamide

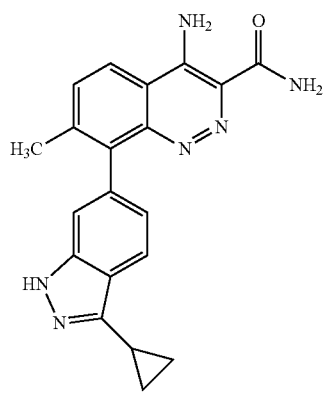 [SMILES: Cc1ccc2c(N)c(C(N)=O)nnc2c1-c1ccc2c(C3CC3)n[nH]c2c1]

The title compound was prepared in a manner similar to EXAMPLE 96 using 6-bromo-3-cyclopropyl-1H-indazole and 4-amino-8-bromo-7-methylcinnoline-3-carboxamide. $^1$H NMR (500 MHz, CD$_3$OD) δ ppm 1.09 (d, J=7.32 Hz, 4H), 2.31 (s, 3 H), 2.31-2.41 (m, 1H), 7.03 (d, J=8.30 Hz, 1 H), 7.37 (s, 1 H), 7.71 (d, J=8.79 Hz, 1 H), 7.90 (d, J=7.81 Hz, 1 H), 8.22 (d, J=8.79 Hz, 1 H); ESI-MS m/z [M+H]+ 359.3.

Example 107

4-amino-8-(5-chloro-1H-indazol-6-yl)-5-fluorocinnoline-3-carboxamide

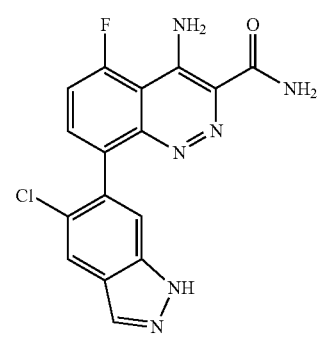 [SMILES: NC(=O)c1nnc2c(-c3cc4[nH]ncc4cc3Cl)ccc(F)c2c1N]

A TFA salt of the title compound was prepared in a manner similar to EXAMPLE 96 using 6-bromo-5-chloro-1H-indazole and 4-amino-8-bromo-5-fluorocinnoline-3-carboxamide. $^1$H NMR (500 MHz, CD$_3$OD) δ ppm 7.65 (d, J=10.74 Hz, 1 H), 7.72 (s, 1 H), 7.94 (br s, 1 H), 8.08 (s, 1 H), 8.18 (br s, 1 H); ESI-MS m/z [M+H]⁺ 333.4.

Example 108

4-amino-8-(3-chloro-1H-indazol-6-yl)-7-methylcinnoline-3-carboxamide

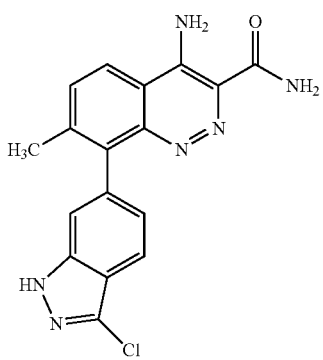 [SMILES: Cc1ccc2c(N)c(C(N)=O)nnc2c1-c1ccc2c(Cl)n[nH]c2c1]

A TFA salt of the title compound was prepared in a manner similar to EXAMPLE 96 using 6-bromo-3-chloro-1H-indazole and 4-amino-8-bromo-7-methylcinnoline-3-carboxamide. ¹H NMR (500 MHz, CD₃OD) δ ppm 2.35 (s, 3 H), 7.20 (dd, J=8.30, 1.46 Hz, 1 H), 7.61 (s, 1 H), 7.88 (d, J=8.30 Hz, 1 H), 7.95 (d, J=8.30 Hz, 1 H), 8.45 (d, J=8.79 Hz, 1 H); ESI-MS m/z [M+H]⁺ 353.3.

Example 109

4-amino-5-fluoro-8-(6-methoxy-1H-indazol-5-yl)cinnoline-3-carboxamide

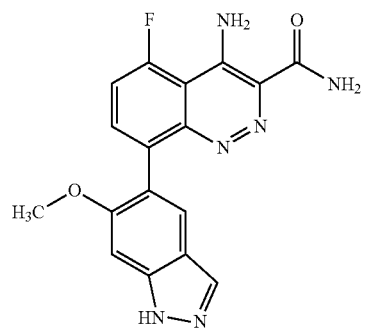 [SMILES: COc1cc2[nH]ncc2cc1-c1ccc(F)c2c(N)c(C(N)=O)nnc12]

A TFA salt of the title compound was prepared in a manner similar to EXAMPLE 96 using 5-bromo-6-methoxy-1H-indazole and 4-amino-8-bromo-5-fluorocinnoline-3-carboxamide. ¹H NMR (500 MHz, CD₃OD) δ ppm 3.80 (s, 3 H), 7.21 (s, 1 H), 7.65 (dd, J=12.69, 8.30 Hz, 1 H), 7.81 (s, 1 H), 7.94 (dd, J=8.30, 5.37 Hz, 1 H), 8.07 (br s, 1 H); ESI-MS m/z [M+H]⁺ 353.3.

Example 110

4-amino-8-(5-methoxy-1H-indazol-6-yl)cinnoline-3-carboxamide

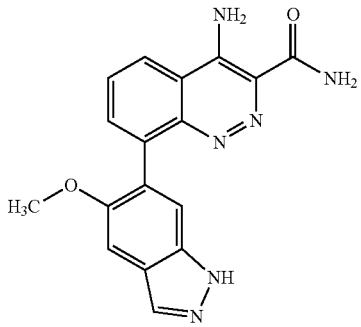 [SMILES: COc1cc2cn[nH]c2cc1-c1cccc2c(N)c(C(N)=O)nnc12]

To a vial containing 4-amino-8-bromocinnoline-3-carboxamide (95 mg, 0.356 mmol), 5-methoxy-6-(4,4,5,5-tetramethyl-1,3,2-dioxaborolan-2-yl)-1H-indazole (127 mg, 0.462 mmol), and NaHCO₃ (90 mg, 1.067 mmol) suspended in a mixture of DMF (3.2 mL) and H₂O (0.356 mL) was added PdCl₂(dppf)CH₂Cl₂ adduct (29 mg, 0.036 mmol). The vial was capped and the reaction mixture was heated at 100° C. for 1 hour in a microwave reactor. The reaction mixture was subsequently cooled, diluted with EtOAc (5 mL), and passed through a Celite pad, which was rinsed with additional EtOAc. The filtrate was concentrated in vacuo and purified by preparative HPLC, eluting with a gradient of 10-40% ACN (containing 0.035% TFA) in water (containing 0.05% TFA). The pure fractions were collected, concentrated, and dried in vacuo to afford a TFA salt of the title compound as a yellow solid (32 mg, 27%). ¹H NMR (500 MHz, CD₃OD) δ ppm 3.78 (s, 3 H), 7.50 (s, 1 H), 7.65 (s, 1 H), 7.94-7.99 (m, 1 H), 8.00-8.04 (m, 1 H), 8.12 (d, J=0.98 Hz, 1 H), 8.54 (dd, J=8.54, 1.22 Hz, 1 H); ESI-MS m/z [M+H]⁺ 335.4.

Example 111

4-amino-5-fluoro-8-(5-methoxy-1H-indazol-6-yl)cinnoline-3-carboxamide

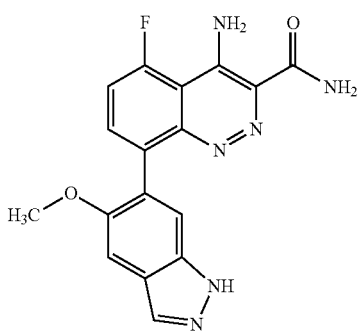 [SMILES: COc1cc2cn[nH]c2cc1-c1ccc(F)c2c(N)c(C(N)=O)nnc12]

To a vial containing 4-amino-8-bromo-5-fluorocinnoline-3-carboxamide (95 mg, 0.333 mmol), 5-methoxy-6-(4,4,5,5- tetramethyl-1,3,2-dioxaborolan-2-yl)-1H-indazole (119 mg, 0.433 mmol), and NaHCO₃ (84 mg, 1.00 mmol) suspended in a mixture of DMF (3 mL) and H₂O (0.333 mL) was added PdCl₂(dppf)CH₂Cl₂ adduct (27 mg, 0.033 mmol). The vial was capped and the reaction mixture was heated at 100° C. for 1 hour in a microwave reactor. The reaction mixture was subsequently cooled, diluted with EtOAc (5 mL), and passed through a Celite pad, which was rinsed with additional EtOAc. The filtrate was concentrated in vacuo and purified by preparative HPLC, eluting with a gradient of 10-40% ACN (containing 0.035% TFA) in water (containing 0.05% TFA). The pure fractions were collected, concentrated, and dried in vacuo to afford a TFA salt of the title compound as a yellow solid (49 mg, 42%). ¹H NMR (500 MHz, CD₃OD) δ ppm 3.76 (s, 3 H), 7.46 (s, 1 H), 7.60 (s, 1 H), 7.64 (dd, J=12.45, 8.05 Hz, 1 H), 7.94 (dd, J=8.30, 5.37 Hz, 1 H), 8.07-8.14 (m, 1 H); ESI-MS m/z [M+H]⁺ 353.3.

Example 112

8-([1,2,4]triazolo[4,3-a]pyridin-6-yl)-4-amino-7-methylcinnoline-3-carboxamide

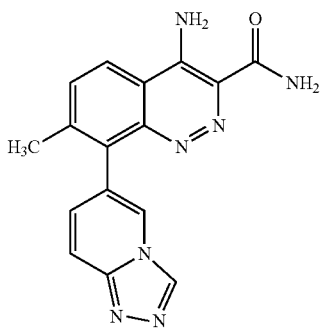 [SMILES: Cc1ccc2c(N)c(C(N)=O)nnc2c1-c1ccc2nncn2c1]

The title compound was prepared in a manner similar to EXAMPLE 96 using 6-bromo-[1,2,4]triazolo[4,3-a]pyridine and 4-amino-8-bromo-7-methylcinnoline-3-carboxamide. ¹H NMR (400 MHz, CD₃OD) δ ppm 2.45 (s, 3 H), 7.45 (d, J=9.35 Hz, 1 H), 7.78 (d, J=8.84 Hz, 1 H), 7.92 (d, J=9.60 Hz, 1 H), 8.34 (d, J=8.84 Hz, 1 H), 8.56 (s, 1 H), 9.25 (s, 1 H); ESI-MS m/z [M+H]⁺ 320.1.

Example 113

4-amino-8-(imidazo[1,5-a]pyridin-6-yl)-7-methyl-cinnoline-3-carboxamide

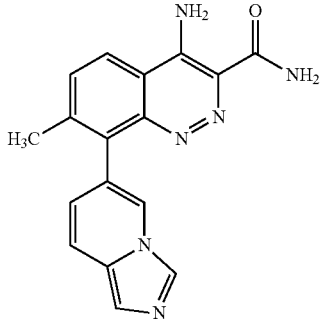 [SMILES: Cc1ccc2c(N)c(C(N)=O)nnc2c1-c1ccc2cncn2c1]

The title compound was prepared in a manner similar to EXAMPLE 96 using 6-bromoimidazo[1,5-a]pyridine and 4-amino-8-bromo-7-methylcinnoline-3-carboxamide. ¹H NMR (400 MHz, CD₃OD) δ ppm 2.45 (s, 3 H), 6.77 (dd, J=9.22, 1.39 Hz, 1 H), 7.47 (s, 1 H), 7.72 (d, J=9.09 Hz, 1 H), 7.67 (d, J=9.35 Hz, 1 H), 8.10-8.32 (m, 2 H), 8.37 (s, 1 H); ESI-MS m/z [M+H]⁺ 319.2.

Example 114

4-amino-8-(imidazo[1,5-a]pyridin-7-yl)-7-methyl-cinnoline-3-carboxamide

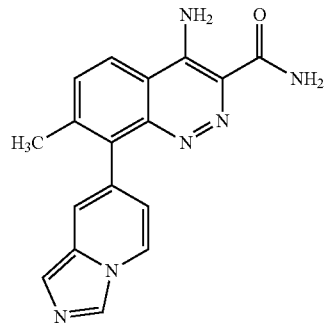 [SMILES: Cc1ccc2c(N)c(C(N)=O)nnc2c1-c1ccn2cncc2c1]

The title compound was prepared in a manner similar to EXAMPLE 96 using 7-bromoimidazo[1,5-a]pyridine and 4-amino-8-bromo-7-methylcinnoline-3-carboxamide. ¹H NMR (400 MHz, CD₃OD) δ ppm 2.44 (s, 3 H), 6.64 (dd, J=7.07, 1.52 Hz, 1 H), 7.44 (s, 1 H), 7.50 (s, 1 H), 7.71 (d, J=8.59 Hz, 1 H), 8.23 (d, J=8.84 Hz, 1 H), 8.35 (d, J=7.07 Hz, 1 H), 8.42 (s, 1 H); ESI-MS m/z [M+H]⁺ 319.1.

Example 115

4-amino-8-(2-phenyl-1H-benzo[d]imidazol-6-yl)cinnoline-3-carboxamide

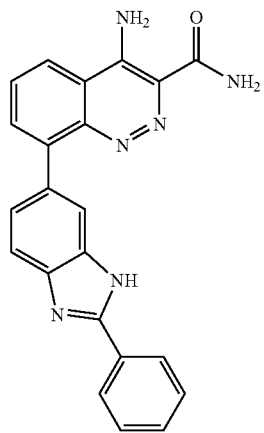 [SMILES: NC(=O)c1nnc2c(-c3ccc4nc(-c5ccccc5)[nH]c4c3)cccc2c1N]

Step A: 6-bromo-2-phenyl-1H-benzo[d]imidazole

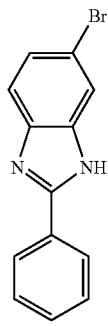 [SMILES: Brc1ccc2nc(-c3ccccc3)[nH]c2c1]

4-Bromobenzene-1,2-diamine (0.5 g, 2.67 mmol), benzaldehyde (0.284 g, 2.67 mmol), and 4-methylbenzenesulfonic acid (0.046 g, 0.267 mmol) in DMF (8 mL) were combined and heated at 100° C. for 1 hour in a microwave reactor. The reaction mixture was subsequently diluted with EtOAc, washed with brine (4×100 mL), concentrated, and purified by CombiFlash® chromatography, eluting with a gradient of MeOH (0-30%) in DCM over 120 minutes. The product-containing fractions were combined and concentrated to give the title compound as light yellow liquid (0.48 g, 66%).

Step B: 2-phenyl-6-(4,4,5,5-tetramethyl-1,3,2-dioxaborolan-2-yl)-1H-benzo[d]imidazole

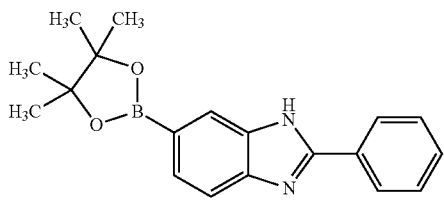 [SMILES: CC1(C)OB(c2ccc3nc(-c4ccccc4)[nH]c3c2)OC1(C)C]

6-Bromo-2-phenyl-1H-benzo[d]imidazole (0.34 g, 1.245 mmol), 4,4,4',4',5,5,5',5'-octamethyl-2,2'-bi(1,3,2-dioxaborolane) (0.632 g, 2.490 mmol), PdCl$_2$(dppf)CH$_2$Cl$_2$ adduct (0.030 g, 0.037 mmol), potassium acetate (0.367 g, 3.73 mmol) and dioxane (10 mL) were combined and heated at 100° C. for 1 hour. The reaction mixture was subsequently cooled, concentrated, and diluted with EtOAc. The mixture was washed with water and brine, dried over Na$_2$SO$_4$, and purified by preparative HPLC (Sunfire Prep 5 μm C18, 75×30 mm column) eluting with a gradient of 30-35% ACN (containing 0.035% TFA) in water (containing 0.05% TFA). The pure fractions were collected and dried in vacuo to give the title compound (0.053 g, 13%).

Step C: 4-amino-8-(2-phenyl-1H-benzo[d]imidazol-6-yl)cinnoline-3-carboxamide

4-Amino-8-bromocinnoline-3-carboxamide (0.040 g, 0.150 mmol), 2-phenyl-6-(4,4,5,5-tetramethyl-1,3,2-dioxaborolan-2-yl)-1H-benzo[d]imidazole (0.048 g, 0.150 mmol), PdCl$_2$(dppf) (5.48 mg, 7.50 μmol), dioxane (8 mL) and saturated NaHCO$_3$ (2 mL) were combined and heated at 140° C. for 30 minutes in a microwave reactor. The reaction mixture was subsequently concentrated and purified via preparative HPLC (Phenomenex Gemini Prep 5 μm C18, 75×30 mm column) eluting with a gradient of 30-35% ACN/H$_2$O (80/20 v/v, containing 10 mM NH$_4$HCO$_3$) in H$_2$O (containing 10 mM NH$_4$HCO$_3$). The product-containing fractions were combined and acetonitrile was evaporated. The aqueous phase was diluted with saturated NaHCO$_3$ and extracted with EtOAc. The organic phase was washed with water and the volatiles were evaporated to give the title compound as a light yellow solid (0.018 g, 32%). $^1$H NMR (400 MHz, DMSO-d$_6$) δ ppm 7.47-7.65 (m, 4 H), 7.65-7.75 (m, 2 H), 7.83 (dd, J=8.21, 7.20 Hz, 1 H), 7.91-8.00 (m, 2 H), 8.23 (d, J=7.07 Hz, 2 H), 8.43 (d, J=7.58 Hz, 1 H), 8.54 (br s, 1 H); ESI-MS m/z [(M+2H)/2]$^+$ 191.1.

Example 116

4-amino-8-(2-(4-fluorophenyl)-1H-benzo[d]imidazol-6-yl)cinnoline-3-carboxamide

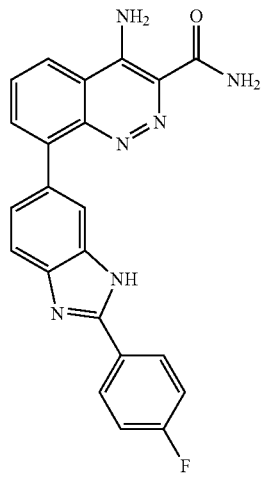 [SMILES: NC(=O)c1nnc2c(-c3ccc4nc(-c5ccc(F)cc5)[nH]c4c3)cccc2c1N]

The title compound was prepared in a manner similar to EXAMPLE 115 using 4-fluorobenzaldehyde in place of benzaldehyde in Step A. $^1$H NMR (400 MHz, DMSO-d$_6$) δ ppm 7.43 (t, J=8.97 Hz, 2 H), 7.55 (d, J=8.59 Hz, 1 H), 7.60-7.75 (m, 2 H), 7.82 (dd, J=8.21, 7.20 Hz, 1 H), 7.89-7.98 (m, 2 H), 8.19-8.33 (m, 2 H), 8.38-8.44 (m, 1 H), 8.54 (br s, 1 H); ESI-MS m/z [M+H]$^+$ 399.2.

Example 117

4-amino-8-(2-(4-tert-butylphenyl)-1H-benzo[d]imidazol-6-yl)cinnoline-3-carboxamide

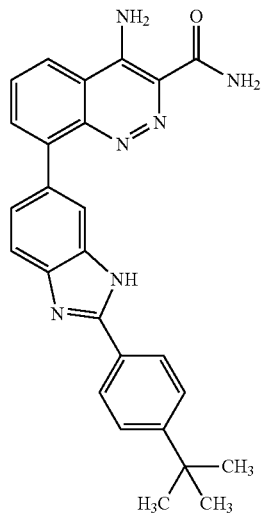 [SMILES: CC(C)(C)c1ccc(-c2nc3ccc(-c4cccc5c(N)c(C(N)=O)nnc45)cc3[nH]2)cc1]

The title compound was prepared in a manner similar to EXAMPLE 115 using 4-tert-butylbenzaldehyde in place of benzaldehyde in Step A. $^1$H NMR (400 MHz, DMSO-d$_6$) δ ppm 1.35 (s, 9 H), 7.52 (dd, J=8.34, 1.52 Hz, 1 H), 7.55-7.69 (m, 4 H), 7.78-7.90 (m, 1 H), 7.90-8.01 (m, 1 H), 8.15 (d, J=8.59 Hz, 2 H), 8.41 (dd, J=8.34, 2.02 Hz, 1 H), 8.55 (br s, 1 H), 12.93 (s, 1 H); ESI-MS m/z [(M+2H)/2]$^+$ 219.

Example 118

4-amino-8-(2-(2,4-difluorophenyl)-1H-benzo[d]imidazol-6-yl)cinnoline-3-carboxamide

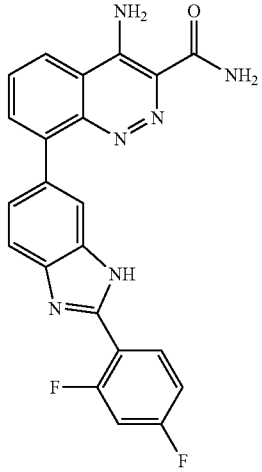 [SMILES: NC(=O)c1nnc2c(-c3ccc4nc(-c5ccc(F)cc5F)[nH]c4c3)cccc2c1N]

A TFA salt of the title compound was prepared in a manner similar to EXAMPLE 115 using 2,4-difluorobenzaldehyde in place of benzaldehyde in Step A. $^1$H NMR (400 MHz, DMSO-d$_6$) δ ppm 7.41 (td, J=8.53, 2.15 Hz, 1 H), 7.51-7.71 (m, 2 H), 7.80-7.97 (m, 3 H), 7.97-8.07 (m, 1 H), 8.25-8.43 (m, 2 H), 8.59 (d, J=8.59 Hz, 1 H); ESI-MS m/z [(M+2H)/2]$^+$ 209.1.

Example 119

4-amino-8-(2-(4-fluoro-2-methoxyphenyl)-1H-benzo[d]imidazol-6-yl)cinnoline-3-carboxamide

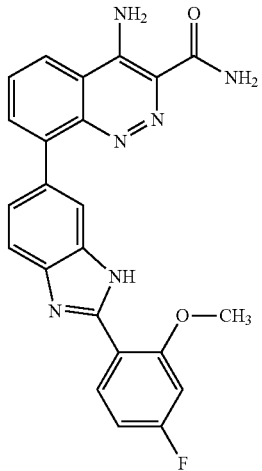 [SMILES: COc1cc(F)ccc1-c1nc2ccc(-c3cccc4c(N)c(C(N)=O)nnc34)cc2[nH]1]

A TFA salt of the title compound was prepared in a manner similar to EXAMPLE 115 using 4-fluoro-2-methoxybenzaldehyde in place of benzaldehyde in Step A. $^1$H NMR (400 MHz, DMSO-d$_6$) δ ppm 4.10 (s, 3 H), 7.17 (t, J=7.33 Hz, 1 H), 7.36 (dd, J=11.37, 2.27 Hz, 1 H), 7.70-7.83 (m, 2 H), 7.83-7.93 (m, 2 H), 7.94-8.03 (m, 1 H), 8.07 (s, 1 H), 8.28 (dd, J=8.84, 6.57 Hz, 1 H), 8.44 (br s, 1 H), 8.52 (d, J=8.84 Hz, 1 H); ESI-MS/m/z [(M+2H)/2]$^+$ 215.

Example 120

4-amino-8-(2-(4-fluorophenyl)-1H-benzo[d]imidazol-6-yl)-7-methylcinnoline-3-carboxamide

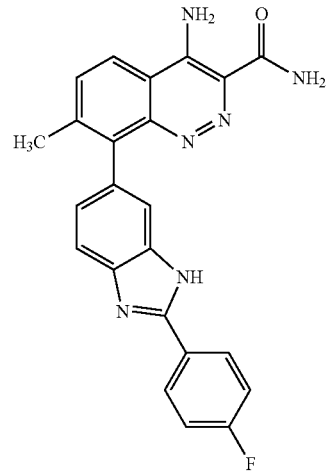 [SMILES: Cc1ccc2c(N)c(C(N)=O)nnc2c1-c1ccc2nc(-c3ccc(F)cc3)[nH]c2c1]

A TFA salt of the title compound was prepared in a manner similar to EXAMPLE 115 using 4-fluorobenzaldehyde in place of benzaldehyde in Step A and 4-amino-8-bromo-7-methylcinnoline-3-carboxamide in place of 4-amino-8-bromocinnoline-3-carboxamide in Step C. $^1$H NMR (400 MHz, CD$_3$OD) δ ppm 2.37 (s, 3 H), 7.43-7.63 (m, 3 H), 7.83-7.99 (m, 2 H), 8.07 (dd, J=8.34, 0.76 Hz, 1 H), 8.21-8.36 (m, 2 H), 8.52 (d, J=8.84 Hz, 1 H); ESI-MS m/z [M+H]$^+$ 413.22.

Example 121

4-amino-8-(1-oxo-2-phenylisoindolin-5-yl)cinnoline-3-carboxamide

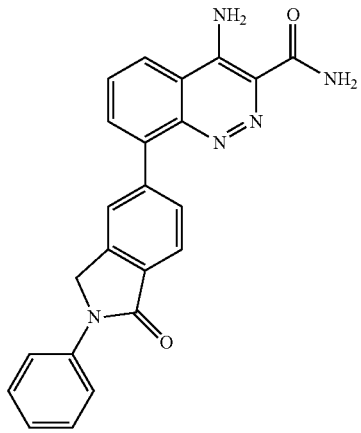 [SMILES: NC(=O)c1nnc2c(-c3ccc4c(c3)CN(c3ccccc3)C4=O)cccc2c1N]

Step A: 5-bromo-2-phenylisoindolin-1-one

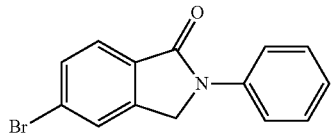 [SMILES: O=C1c2ccc(Br)cc2CN1c1ccccc1]

To a suspension of methyl 4-bromo-2-(bromomethyl)benzoate (0.204 g, 0.662 mmol) in MeOH (5.5 mL) were added aniline (0.063 mL, 0.696 mmol) and Et$_3$N (0.144 mL, 1.027 mmol). The mixture was heated to reflux (85° C.) for 24 hours and subsequently cooled. A white solid that formed was collected by vacuum filtration, rinsed with MeOH, and dried under vacuum to give the title compound as a white solid (0.138 g, 72% yield). $^1$H NMR (500 MHz, CDCl$_3$) δ ppm 3.89 (s, 2 H), 4.85 (s, 2 H), 7.15-7.24 (m, 1 H), 7.40-7.52 (m, 2 H), 7.62-7.96 (m, 5 H); ESI-MS m/z/[M+H]$^+$ 288.3.

Step B: 2-phenyl-5-(4,4,5,5-tetramethyl-1,3,2-dioxaborolan-2-yl)isoindolin-1-one

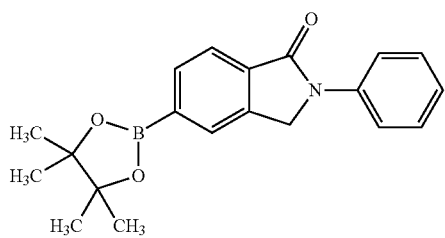 [SMILES: CC1(C)OB(c2ccc3c(c2)CN(c2ccccc2)C3=O)OC1(C)C]

5-bromo-2-phenylisoindolin-1-one (0.138 g, 0.479 mmol), bis(pinacolato)diboron (0.182 g, 0.718 mmol), potassium acetate (0.141 g, 1.437 mmol) and PdCl$_2$(dppf)CH$_2$Cl$_2$ adduct (0.020 g, 0.024 mmol) were suspended in DMA (1.0 mL). The mixture was degassed with N$_2$ and heated in a sand bath at 100° C. overnight. The reaction mixture was subsequently diluted with EtOAc (15 mL) and passed through a pad of Celite. Water (20 mL) was added to the filtrate. The resulting layers were separated, and the aqueous layer was extracted with EtOAc (3×10 mL). The organic layers were combined, washed with brine, dried over MgSO$_4$, filtered, and concentrated in vacuo to afford the title compound as a crystalline brown solid (0.277 g).

Step C: 4-amino-8-(1-oxo-2-phenylisoindolin-5-yl)cinnoline-3-carboxamide

4-Amino-8-bromocinnoline-3-carboxamide (0.045 g, 0.168 mmol), 2-phenyl-5-(4,4,5,5-tetramethyl-1,3,2-dioxaborolan-2-yl)isoindolin-1-one (0.056 g, 0.168 mmol), Na$_2$CO$_3$ (0.168 mL, 0.337 mmol), and PdCl$_2$(dppf)CH$_2$Cl$_2$ adduct (9.63 mg, 0.012 mmol) were suspended in THF (1.2 mL) and heated at 130° C. for 1 hour. The reaction mixture was cooled, diluted with EtOAc, and passed through a syringe filter. The filtrate was concentrated in vacuo, taken up in DMSO, and purified by preparative HPLC (Sunfire Prep 5 μm C18, 75×30 mm column) eluting with a gradient of 20-40% ACN (containing 0.035% TFA) in water (containing 0.05% TFA). The pure fractions were collected and dried in vacuo. The product was reconstituted in ACN/water (1:1) and lyophilized to give a TFA salt of the title compound as a pale beige solid (3 mg). $^1$H NMR (500 MHz, DMSO-d$_6$) δ ppm 5.12 (s, 2 H), 7.21 (t, J=7.32 Hz, 1 H), 7.47 (t, J=6.83 Hz, 2 H), 7.67 (br s, 1 H), 7.78-8.05 (m, 7 H), 8.42 (br s, 1 H), 8.48-8.59 (m, 2 H), 9.34 (br s, 1 H); ESI-MS m/z [M+H]$^+$ 396.3.

Example 122

4-amino-8-(1-oxo-2-phenylisoindolin-5-yl)cinnoline-3-carboxamide

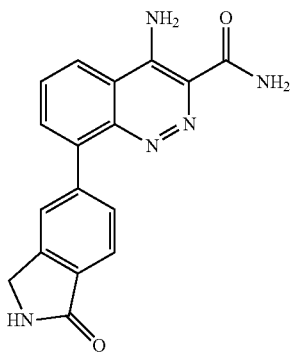 [SMILES: NC(=O)c1nnc2c(-c3ccc4c(c3)CNC4=O)cccc2c1N]

A TFA salt of the title compound was prepared in a manner similar to EXAMPLE 121 using 5-(4,4,5,5-tetramethyl-1,3,2-dioxaborolan-2-yl)isoindolin-1-one in place of 2-phenyl-5-(4,4,5,5-tetramethyl-1,3,2-dioxaborolan-2-yl)isoindolin-1-one in Step C. $^1$H NMR (500 MHz, DMSO-d$_6$) δ ppm 5.12 (s, 2 H), 7.21 (t, J=7.32 Hz, 1 H), 7.47 (t, J=6.83 Hz, 2 H), 7.67 (br s, 1 H), 7.78-8.05 (m, 7 H), 8.42 (br s, 1 H), 8.48-8.59 (m, 2 H), 9.34 (br s, 1 H); ESI-MS m/z [M+H]$^+$ 320.4.

Example 123

4-amino-8-(2-methyl-1-oxoisoindolin-5-yl)cinnoline-3-carboxamide

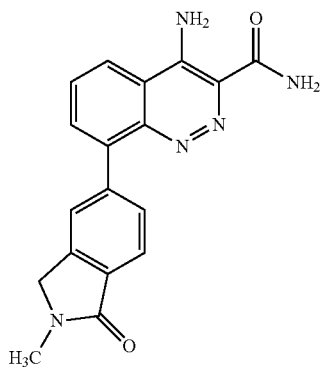 [SMILES: CN1Cc2cc(-c3cccc4c(N)c(C(N)=O)nnc34)ccc2C1=O]

A TFA salt of the title compound was prepared in a manner similar to EXAMPLE 121 using 2-methyl-5-(4,4,5,5-tetramethyl-1,3,2-dioxaborolan-2-yl)isoindolin-1-one in place of 2-phenyl-5-(4,4,5,5-tetramethyl-1,3,2-dioxaborolan-2-yl)isoindolin-1-one in Step C. $^1$H NMR (500 MHz, DMSO-d$_6$) δ ppm 3.13 (s, 3 H), 4.54 (s, 2 H), 7.68 (br s, 1 H), 7.77 (s, 2

H), 7.80-7.89 (m, 2 H), 7.89-7.96 (m, 1 H), 8.45-8.58 (m, 2 H); ESI-MS m/z [M+H]⁺ 334.4.

Example 124

4-amino-7-methyl-8-(1-oxoisoindolin-5-yl)cinnoline-3-carboxamide

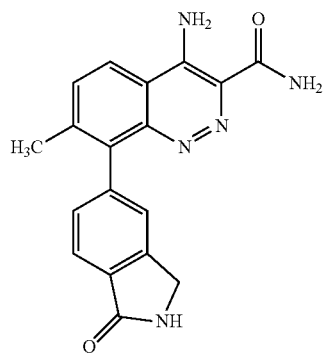 [SMILES: Cc1ccc2c(N)c(C(N)=O)nnc2c1-c1ccc2c(c1)CNC2=O]

A TFA salt of the title compound was prepared in a manner similar to EXAMPLE 121 using 5-(4,4,5,5-tetramethyl-1,3,2-dioxaborolan-2-yl)isoindolin-1-one and 4-amino-8-bromo-7-methylcinnoline-3-carboxamide in place of 2-phenyl-5-(4,4,5,5-tetramethyl-1,3,2-dioxaborolan-2-yl)isoindolin-1-one and 4-amino-8-bromocinnoline-3-carboxamide in Step C. ¹H NMR (500 MHz, DMSO-d₆) δ ppm 2.22-2.31 (m, 3 H), 4.38-4.54 (m, 2 H), 7.41 (dd, J=7.81, 0.98 Hz, 1 H), 7.52 (s, 1 H), 7.73-7.85 (m, 3 H), 8.28 (br s, 1 H), 8.49 (d, J=8.79 Hz, 1 H), 8.63 (s, 1 H); ESI-MS m/z [M+H]⁺ 334.4.

Example 125

4-amino-5-fluoro-8-(1-oxoisoindolin-5-yl)cinnoline-3-carboxamide

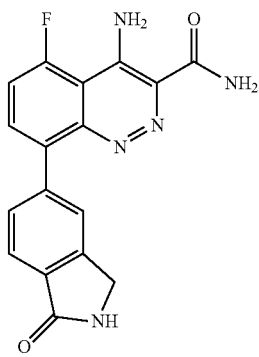 [SMILES: NC(=O)c1nnc2c(-c3ccc4c(c3)CNC4=O)ccc(F)c2c1N]

A TFA salt of the title compound was prepared in a manner similar to EXAMPLE 121 using 5-(4,4,5,5-tetramethyl-1,3,2-dioxaborolan-2-yl)isoindolin-1-one and 4-amino-8-bromo-5-fluorocinnoline-3-carboxamide in place of 2-phenyl-5-(4,4,5,5-tetramethyl-1,3,2-dioxaborolan-2-yl)isoindolin-1-one and 4-amino-8-bromocinnoline-3-carboxamide in Step C. ¹H NMR (500 MHz, DMSO-d₆) δ ppm 4.45 (s, 2 H), 7.61 (dd, J=12.69, 8.30 Hz, 1 H), 7.68-7.74 (m, 3 H), 7.74-7.78 (m, 1 H), 7.81 (s, 1 H), 7.89 (dd, J=8.30, 5.86 Hz, 1 H), 8.60 (br s, 2 H), 9.68 (br s, 1 H); ESI-MS m/z [M+H]⁺ 338.4.

Example 126

4-amino-5-fluoro-7-methyl-8-(1-oxoisoindolin-5-yl)cinnoline-3-carboxamide

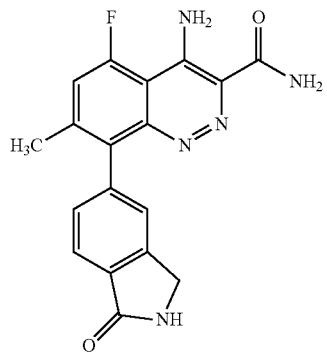 [SMILES: Cc1cc(F)c2c(N)c(C(N)=O)nnc2c1-c1ccc2c(c1)CNC2=O]

A TFA salt of the title compound was prepared in a manner similar to EXAMPLE 121 using 5-(4,4,5,5-tetramethyl-1,3,2-dioxaborolan-2-yl)isoindolin-1-one and 4-amino-8-bromo-5-fluoro-7-methylcinnoline-3-carboxamide in place of 2-phenyl-5-(4,4,5,5-tetramethyl-1,3,2-dioxaborolan-2-yl)isoindolin-1-one and 4-amino-8-bromocinnoline-3-carboxamide in Step C. ¹H NMR (500 MHz, DMSO-d₆) δ ppm 2.26 (s, 3 H), 4.43 (s, 2 H), 7.34-7.40 (m, 1 H), 7.47 (s, 1 H), 7.57 (d, J=13.67 Hz, 1H), 7.65 (br s, 2H), 7.76 (d, J=7.81 Hz, 1 H), 8.44 (br s, 1 H), 8.58 (s, 1 H), 9.55 (br s, 1 H); ESI-MS m/z [M+H]⁺ 352.3.

Example 127

4-amino-8-(2-(3-hydroxy-3-methylbutyl)-1-oxoisoindolin-5-yl)cinnoline-3-carboxamide

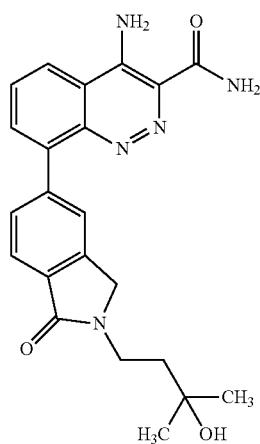 [SMILES: CC(C)(O)CCN1Cc2cc(-c3cccc4c(N)c(C(N)=O)nnc34)ccc2C1=O]

A TFA salt of the title compound was prepared in a manner similar to EXAMPLE 121 using 2-(3-hydroxy-3-methylbutyl)-5-(4,4,5,5-tetramethyl-1,3,2-dioxaborolan-2-yl)isoindolin-1-one in place of 2-phenyl-5-(4,4,5,5-tetramethyl-1,3, 2-dioxaborolan-2-yl)isoindolin-1-one in Step C. $^1$H NMR (500 MHz, DMSO-$d_6$) δ ppm 1.14-1.21 (m, 6 H), 1.68-1.77 (m, 2 H), 3.61-3.70 (m, 2 H), 4.55 (s, 2 H), 7.76 (q, J=7.49 Hz, 3 H), 7.81-7.89 (m, 2 H), 7.89-7.97 (m, 1 H), 8.45-8.56 (m, 2 H), 8.70 (br s, 1H), 9.53 (br s, 1H); ESI-MS m/z [M+H]$^+$ 406.4.

Example 128

4-amino-8-(2-(3-hydroxy-3-methylbutyl)-1-oxoisoindolin-5-yl)-7-methylcinnoline-3-carboxamide

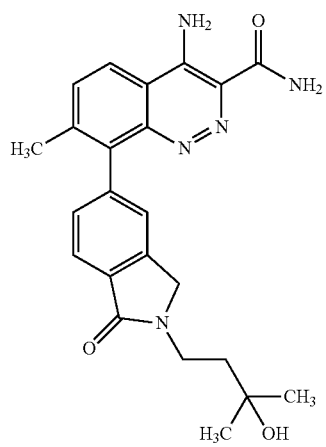 [SMILES: Cc1ccc2c(N)c(C(N)=O)nnc2c1-c1ccc2c(c1)CN(CCC(C)(C)O)C2=O]

A TFA salt of the title compound was prepared in a manner similar to EXAMPLE 121 using 2-(3-hydroxy-3-methylbutyl)-5-(4,4,5,5-tetramethyl-1,3,2-dioxaborolan-2-yl)isoindolin-1-one and 4-amino-8-bromo-7-methylcinnoline-3-carboxamide in place of 2-phenyl-5-(4,4,5,5-tetramethyl-1,3,2-dioxaborolan-2-yl)isoindolin-1-one and 4-amino-8-bromocinnoline-3-carboxamide in Step C. $^1$H NMR (500 MHz, DMSO-$d_6$) δ ppm 1.13-1.21 (m, 6 H), 1.68-1.77 (m, 2 H), 2.23-2.30 (m, 3 H), 3.61-3.71 (m, 2 H), 4.48-4.62 (m, 2 H), 7.38-7.43 (m, 1 H), 7.54 (s, 1 H), 7.76-7.90 (m, 3 H), 8.25 (br s, 1 H), 8.50 (d, J=8.79 Hz, 1 H).

Example 129

4-amino-7-ethyl-8-(1-oxoisoindolin-5-yl)cinnoline-3-carboxamide

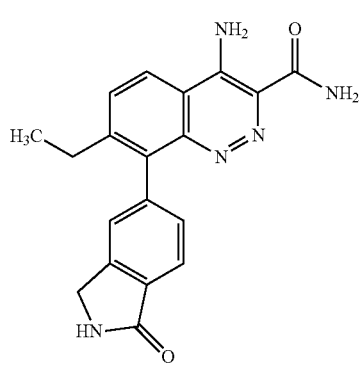 [SMILES: CCc1ccc2c(N)c(C(N)=O)nnc2c1-c1ccc2c(c1)CNC2=O]

A TFA salt of the title compound was prepared in a manner similar to EXAMPLE 121 using 5-(4,4,5,5-tetramethyl-1,3,2-dioxaborolan-2-yl)isoindolin-1-one and 4-amino-8-bromo-7-ethylcinnoline-3-carboxamide in place of 2-phenyl-5-(4,4,5,5-tetramethyl-1,3,2-dioxaborolan-2-yl)isoindolin-1-one and 4-amino-8-bromocinnoline-3-carboxamide in Step C. $^1$H NMR (500 MHz, DMSO-$d_6$) δ ppm 1.06-1.14 (m, 3 H), 2.52-2.59 (m, 2 H), 4.38-4.51 (m, 2 H), 7.39 (d, J=7.81 Hz, 1 H), 7.51 (s, 1 H), 7.76-7.86 (m, 2 H), 8.28 (br s, 1 H), 8.51 (d, J=9.76 Hz, 1 H), 8.62 (s, 1 H); ESI-MS m/z [M+H]$^+$ 348.4.

Example 130

4-amino-8-(2-cyano-1H-benzo[d]imidazol-6-yl)cinnoline-3-carboxamide

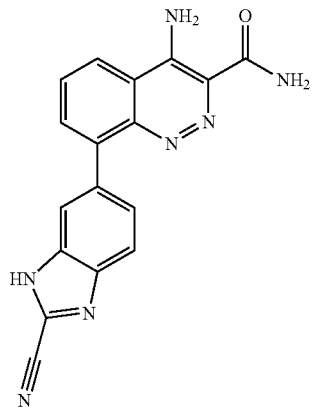 [SMILES: N#Cc1nc2ccc(-c3cccc4c(N)c(C(N)=O)nnc34)cc2[nH]1]

4,5-Dichloro-1,2,3-dithiazol-1-ium chloride (15.59 mg, 0.075 mmol) was added to a solution of 4-amino-8-(3,4-diaminophenyl)cinnoline-3-carboxamide (20 mg, 0.068 mmol) in pyridine (1 mL), and the mixture was stirred at RT for 2 hours. The residue was purified by preparative HPLC (Sunfire Prep 5 μm C18, 75×30 mm column) eluting with gradient of 5-30% ACN (containing 0.035% TFA) in water (containing 0.05% TFA). The product fractions were collected, concentrated, and dried in vacuo to give a TFA salt of the title compound as a white solid (5.6 mg, 25%). $^1$H NMR (500 MHz, CD$_3$OD) δ ppm 7.65 (dd, J=8.54, 1.71 Hz, 1 H), 7.91-7.99 (m, 3 H), 8.04-8.08 (m, 1 H), 8.51-8.54 (m, 1 H); ESI-MS m/z [M+H]$^+$ 330.3

Examples 131 and 132

4-amino-8-(1-ethyl-1H-benzo[d]imidazol-6-yl)-7-methylcinnoline-3-carboxamide and 4-amino-8-(1-ethyl-1H-benzo[d]imidazol-5-yl)-7-methylcinnoline-3-carboxamide

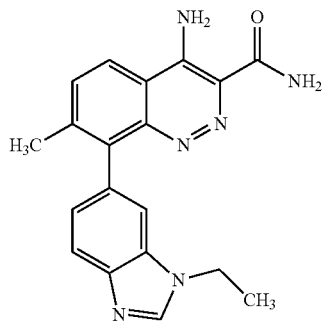

and

-continued

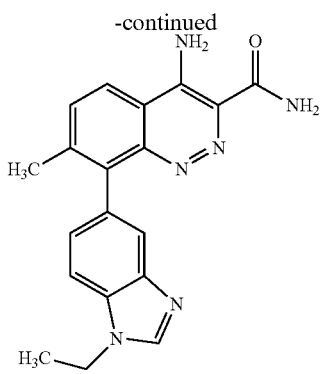

Step A: 1-ethyl-6-(4,4,5,5-tetramethyl-1,3,2-dioxaborolan-2-yl)-1H-benzo[d]imidazole and 1-ethyl-5-(4,4,5,5-tetramethyl-1,3,2-dioxaborolan-2-yl)-1H-benzo[d]imidazole

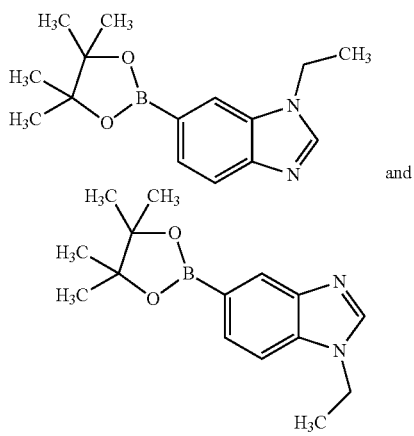

and

To a mixture of sodium tert-butoxide (0.091 g, 0.945 mmol) and 5-(4,4,5,5-tetramethyl-1,3,2-dioxaborolan-2-yl)-1H-benzo[d]imidazole (0.077 g, 0.315 mmol) in DMF was added iodoethane (0.059 g, 0.378 mmol). The reaction mixture was stirred at room temperature for 3 hours. The mixture was subsequently concentrated and passed through a silica plug to give the title compounds as a mixture, which was used without further purification.

Step B: 4-amino-8-(1-ethyl-1H-benzo[d]imidazol-6-yl)-7-methylcinnoline-3-carboxamide and 4-amino-8-(1-ethyl-1H-benzo[d]imidazol-5-yl)-7-methylcinnoline-3-carboxamide A mixture of 1-ethyl-6-(4,4,5,5-tetramethyl-1,3,2-dioxaborolan-2-yl)-1H-benzo[d]imidazole and 1-ethyl-5-(4,4,5,5-tetramethyl-1,3,2-dioxaborolan-2-yl)-1H-benzo[d]imidazole, 4-amino-8-bromo-7-methylcinnoline-3-carboxamide hydrochloride (0.10 g, 0.315 mmol), and sodium bicarbonate (0.079 g, 0.945 mmol) were suspended in a dioxane/water mixture. PdCl$_2$(dppf)CH$_2$Cl$_2$ adduct (0.026 g, 0.031 mmol) was added and the mixture was heated at 140° C. for 1 hour. The reaction mixture was subsequently diluted with EtOAc (5 mL) and passed through a Celite pad, which was rinsed with additional EtOAc. The filtrate was concentrated in vacuo purified by preparative HPLC (Sunfire Prep 5 µm C18, 75×30 mm column) eluting with a gradient of 10-30% ACN (containing 0.035% TFA) in water (containing 0.05% TFA). The product fractions were collected, concentrated, and dried in vacuo to give TFA salts of the title compounds as yellow solids. EXAMPLE 131 (10 mg, 9.2%): $^1$H NMR (500 MHz, CD$_3$OD) δ ppm 1.61-1.68 (m, 3 H), 2.70 (s, 3 H), 4.52-4.61 (m, 2 H), 7.61 (dd, J=8.30, 2.44 Hz, 1 H), 7.92 (d, J=9.28 Hz, 1 H), 8.06 (br s, 1 H), 8.10 (d, J=8.30 Hz, 1 H), 8.51 (d, J=8.79 Hz, 1 H), 9.41 (br s, 1 H); and 132 (9 mg, 8%): $^1$H NMR (500 MHz, CD$_3$OD) δ ppm 1.66-1.75 (m, 3 H), 2.27-2.38 (m, 3 H), 4.67 (q, J=7.32 Hz, 2 H), 7.65 (d, J=8.79 Hz, 1 H), 7.92 (d, J=8.79 Hz, 1 H), 7.96 (s, 1 H), 8.22 (d, J=8.79 Hz, 1 H), 8.51 (d, J=8.79 Hz, 1 H), 9.50 (br s, 1 H).

Example 133

4-amino-8-(1-(2-cyanoethyl)-1H-benzo[d]imidazol-6-yl)-7-methylcinnoline-3-carboxamide

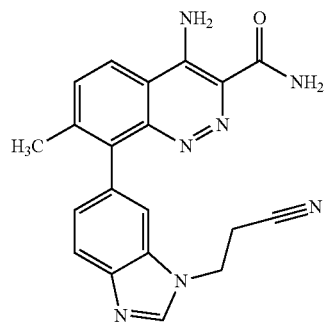 [SMILES: Cc1ccc2c(N)c(C(N)=O)nnc2c1-c1ccc2ncn(CCC#N)c2c1]

A TFA salt of the title compound was prepared in a manner similar to EXAMPLE 131 using 3-bromopropanenitrile in place of iodoethane. $^1$H NMR (500 MHz, CD$_3$OD) δ ppm 2.34 (s, 3 H), 3.16 (td, J=6.35, 2.93 Hz, 2 H), 4.75-4.81 (m, 2 H), 7.43-7.48 (m, 1 H), 7.88-7.93 (m, 1 H), 7.95 (s, 1 H), 8.01-8.12 (m, 1 H), 8.45-8.51 (m, 1 H), 8.88 (br s, 1 H).

Example 134

4-amino-8-(1-(2-hydroxyethyl)-1H-benzo[d]imidazol-6-yl)-7-methylcinnoline-3-carboxamide

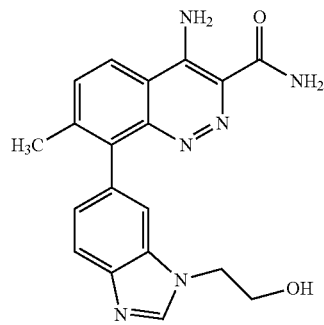 [SMILES: Cc1ccc2c(N)c(C(N)=O)nnc2c1-c1ccc2ncn(CCO)c2c1]

A TFA salt of the title compound was prepared in a manner similar to EXAMPLE 131 using 2-bromoethanol in place of iodoethane. ESI-MS m/z [M+H]+ 363.3.

Example 135

4-amino-7-cyano-8-(1H-indazol-6-yl)cinnoline-3-carboxamide

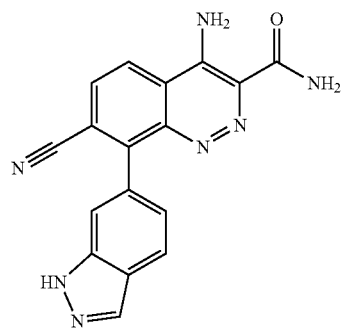 [SMILES: N#Cc1ccc2c(N)c(C(N)=O)nnc2c1-c1ccc2cn[nH]c2c1]

4-Amino-7-chloro-8-(1H-indazol-6-yl)cinnoline-3-carboxamide (14 mg, 0.041 mmol), S-Phos (1.7 mg, 0.004 mmol), dicyanozinc (5.8 mg, 0.05 mmol), Pd$_2$(dba)$_3$ (1.9 mg, 0.002 mmol), and a drop of water were stirred in DMF (0.4 mL) at 150° C. for 30 minutes. The crude mixture was filtered and purified by preparative HPLC (Sunfire Prep 5 μm C18, 75×30 mm column) eluting with a gradient of 5-30% ACN (containing 0.035% TFA) in water (containing 0.05% TFA). The product fractions were collected, concentrated, and dried in vacuo to give a TFA salt of the title compound as a white solid (7 mg, 51%). $^1$H NMR (500 MHz, CD$_3$OD) δ ppm 7.26-7.38 (m, 1 H), 7.81 (s, 1 H), 8.04 (d, J=7.81 Hz, 1 H), 8.10 (d, J=8.79 Hz, 1 H), 8.23 (s, 1 H), 8.56 (d, J=8.79 Hz, 1 H); ESI-MS m/z [M+H]+ 330.1.

Example 136

4-amino-6-fluoro-8-(5-methyl-1H-indazol-6-yl)cinnoline-3-carboxamide

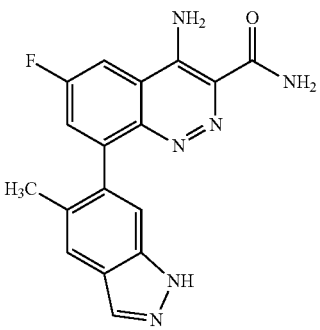 [SMILES: Cc1cc2cn[nH]c2cc1-c1cc(F)cc2c(N)c(C(N)=O)nnc12]

4-Amino-8-bromo-6-fluorocinnoline-3-carboxamide (500 mg, 1.76 mmol, 1 eq), NaHCO$_3$ (591 mg), 5-methyl-1H-indazol-6-yl)boronic acid (326 mg), Pd(dppf)Cl$_2$ (128 mg), H$_2$O (2 mL) and dioxane (10 mL) were stirred at 105° C. overnight under N$_2$. The reaction mixture was cooled to room temperature, concentrated, and purified on silica column chromatography eluting with DCM/MeOH (40:1 to 5:1 gradient) to give the title compound (580 mg, 98%). $^1$H NMR (400 MHz, DMSO-d$_6$) δ ppm 13.01 (1H, s), 9.16 (1H, br s), 8.42 (1H, s), 8.32 (1H, d, J=2.4 Hz), 8.22 (1H, br s), 8.05 (1H, s), 8.72 (1H, d, J=2.8 Hz), 7.64 (2H, s), 7.41 (1H, s), 2.01 (3H, s); LC-MS (20-95% ACN in H$_2$O gradient with 0.02% NH$_4$OAc, t$_R$ 2.579 minutes); ESI+APCI m/z [M+H]+ 337.

Example 137

4-amino-8-(5-methyl-1H-indazol-6-yl)-6-morpholinocinnoline-3-carboxamide

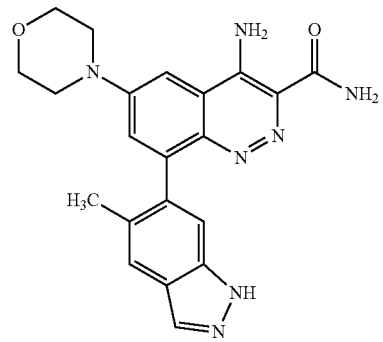 [SMILES: Cc1cc2cn[nH]c2cc1-c1cc(N2CCOCC2)cc2c(N)c(C(N)=O)nnc12]

A mixture of 4-amino-6-fluoro-8-(5-methyl-1H-indazol-6-yl)cinnoline-3-carboxamide (200 mg, 0.59 mmol), DIPEA (1000 mg), morpholine (500 mg,) and DMA (4 mL) was heated at 140° C. in a microwave under N$_2$ for 3 hours. The mixture was cooled, concentrated, and purified via preparative HPLC to give the title compound (60 mg, 25%). $^1$H NMR (400 MHz, DMSO-d$_6$) δ ppm 12.95 (1H, s), 8.93 (1H, br s), 8.30 (1H, d, J=2.4 Hz), 8.03 (1H, s), 7.81 (1H, br s), 7.60 (1H, s), 7.54-7.51 (3H, m), 7.35 (1H, s), 3.79 (4H, t, J=4.8 Hz), 3.42 (4H, t, J=4.8 Hz), 2.00 (3H, s); LC-MS (5-95% ACN in H$_2$O gradient with 0.02% NH$_4$OAc, t$_R$ 3.053 minutes); ESI+APCI m/z [M+H]+ 404.

Example 138

4-amino-6-(4-hydroxypiperidin-1-yl)-8-(5-methyl-1H-indazol-6-yl)cinnoline-3-carboxamide

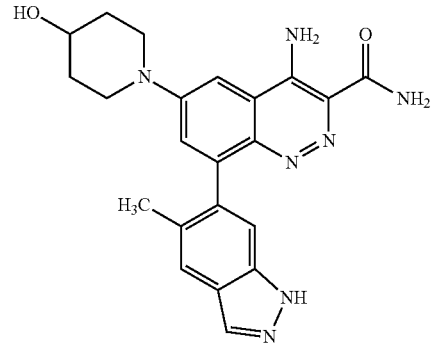 [SMILES: Cc1cc2cn[nH]c2cc1-c1cc(N2CCC(O)CC2)cc2c(N)c(C(N)=O)nnc12]

The mixture of 4-amino-6-fluoro-8-(5-methyl-1H-indazol-6-yl)cinnoline-3-carboxamide (200 mg, 0.59 mmol), DIPEA (1000 mg), piperidin-4-ol (573 mg) and DMA (4 mL) was heated at 140° C. in a microwave under N$_2$ for 3 h. The mixture was cooled, concentrated and purified directly with prep-HPLC to give the title compound as solid (60 mg, yield=24%). $^1$H NMR (400 MHz, DMSO-d6): δ 12.93 (1H, s), 8.27 (1H, s), 8.02 (1H, s), 7.60 (1H, s), 7.48-7.47 (3H, m), 7.35 (1H, s), 4.74 (1H, d, J=4.4 Hz), 3.89-3.86 (2H, m), 3.75-3.72 (m, 1H), 3.17-3.12 (2H, m), 2.00 (3H, s), 1.87-1.84 (2H, m), 1.53-1.49 (2H, m); LC-MS (5-95% ACN in H$_2$O gradient with 0.02% NH$_4$OAc, t$_R$ 2.809 minutes); ESI+APCI m/z [M+H]$^+$ 418.

TABLE 1, below, lists BTK inhibition data for many of the compounds described in the examples, where larger pIC$_{50}$ values represent higher potency. The compounds were tested in accordance with the assay described on page 34 of the specification.

As used in this specification and the appended claims, singular articles such as "a," "an," and "the," may refer to a single object or to a plurality of objects unless the context clearly indicates otherwise. Thus, for example, reference to a composition containing "a compound" may include a single compound or two or more compounds. It is to be understood that the above description is intended to be illustrative and not restrictive. Many embodiments will be apparent to those of skill in the art upon reading the above description. Therefore, the scope of the invention should be determined with reference to the appended claims and includes the full scope of equivalents to which such claims are entitled. The disclosures of all articles and references, including patents, patent applications and publications, are herein incorporated by reference in their entirety and for all purposes.

TABLE 1

BTK Inhibition (pIC$_{50}$) for Example (Ex) Compounds

| Ex. | pIC$_{50}$ |
|---|---|
| 1 | 5.8 |
| 2 | 6.8 |
| 3 | 6.5 |
| 4 | 7.1 |
| 5 | 5.4 |
| 6 | 5.5 |
| 7 | 5.3 |
| 8 | 5.9 |
| 9 | 6.0 |
| 10 | 6.2 |
| 11 | 6.0 |
| 12 | 4.8 |
| 13 | 4.4 |
| 14 | 6.2 |
| 15 | 6.1 |
| 16 | 6.1 |
| 17 | 4.3 |
| 18 | 5.9 |
| 19 | 4.8 |
| 20 | 4.4 |
| 21 | 6.9 |
| 22 | 7.8 |
| 23 | 7.3 |
| 24 | 6.6 |
| 25 | 7.5 |
| 26 | 6.8 |
| 27 | 5.8 |
| 28 | 8.1 |
| 30 | 6.5 |
| 31 | 7.4 |
| 32 | 7.3 |
| 33 | 7.3 |
| 34 | 5.8 |
| 35 | 7.1 |
| 36 | 6.3 |
| 37 | 5.4 |
| 38 | 7.4 |
| 39 | 8.1 |

TABLE 1-continued

BTK Inhibition (pIC$_{50}$) for Example (Ex) Compounds

| Ex. | pIC$_{50}$ |
|---|---|
| 40 | 8.2 |
| 41 | 7.6 |
| 42 | 8.0 |
| 43 | 8.2 |
| 44 | 6.3 |
| 45 | 7.0 |
| 46 | 7.2 |
| 47 | 7.1 |
| 48 | 7.7 |
| 49 | 8.0 |
| 50 | 7.0 |
| 51 | 7.9 |
| 52 | 5.6 |
| 53 | 7.3 |
| 54 | 7.8 |
| 55 | 7.4 |
| 56 | 7.9 |
| 57 | 6.7 |
| 58 | 7.3 |
| 60 | 8.1 |
| 61 | 8.0 |
| 62 | 8.3 |
| 63 | 7.6 |
| 64 | 8.0 |
| 65 | 7.2 |
| 66 | 6.2 |
| 67 | 7.2 |
| 68 | 6.8 |
| 69 | 7.5 |
| 70 | 7.1 |
| 71 | 6.5 |
| 72 | 5.9 |
| 73 | 6.8 |
| 74 | 7.1 |
| 75 | 6.9 |
| 76 | 6.9 |
| 77 | 6.2 |
| 78 | 7.1 |
| 79 | 6.5 |
| 80 | 7.4 |
| 81 | 5.6 |
| 82 | 6.7 |
| 83 | 6.1 |
| 84 | 6.4 |
| 85 | 6.0 |
| 86 | 5.7 |
| 87 | 7.0 |
| 88 | 8.0 |
| 90 | 7.8 |
| 91 | 7.1 |
| 92 | 6.0 |
| 93 | 8.1 |
| 94 | 7.2 |
| 95 | 7.2 |
| 96 | 6.8 |
| 97 | 7.0 |
| 98 | 5.3 |
| 99 | 7.2 |
| 100 | 7.6 |
| 101 | 7.5 |
| 102 | 7.6 |
| 103 | 8.4 |
| 104 | 7.5 |
| 105 | 7.8 |
| 106 | 6.3 |
| 107 | 7.8 |
| 108 | 7.4 |
| 109 | 8.7 |
| 110 | 8.4 |
| 111 | 8.7 |
| 112 | 7.0 |
| 113 | 7.7 |
| 114 | 8.4 |
| 115 | 7.1 |
| 116 | 7.4 |
| 117 | 7.1 |

TABLE 1-continued

BTK Inhibition (pIC$_{50}$) for Example (Ex) Compounds

| Ex. | pIC$_{50}$ |
|-----|------------|
| 118 | 7.0 |
| 120 | 7.6 |
| 121 | 6.9 |
| 122 | 7.7 |
| 123 | 6.7 |
| 124 | 8.2 |
| 125 | 7.4 |
| 126 | 7.9 |
| 127 | 7.6 |
| 128 | 8.1 |
| 129 | 8.3 |
| 130 | 6.7 |
| 131 | 7.0 |
| 132 | 5.9 |
| 133 | 6.3 |
| 134 | 6.1 |
| 135 | 6.9 |
| 136 | 8.0 |
| 137 | 8.1 |
| 138 | 7.9 |

What is claimed is:

1. A compound of Formula 1, or a pharmaceutically acceptable salt thereof, wherein:
$R^1$ is hydrogen;
$R^2$ is selected from hydrogen, halo, —CN, $C_{1-4}$ alkyl, $C_{1-4}$ haloalkyl, —NO$_2$, and —OR$^{14}$;
$R^3$ is selected from hydrogen, halo, —CN, $C_{1-4}$ alkyl, $C_{1-4}$ haloalkyl, —NO$_2$, —OR$^{14}$, and $C_{2-6}$ heterocyclyl optionally substituted with from one to three substituents independently selected from halo, hydroxy, oxo, and —CN;
$R^4$ is selected from hydrogen, halo, —CN, $C_{1-4}$ alkyl, $C_{1-4}$ haloalkyl, —NO$_2$, and —OR$^{14}$;
$R^5$ is a bicyclic $C_{6-9}$ heteroaryl having from one to four heteroatoms, each of the heteroatoms being nitrogen, wherein the bicyclic $C_{6-9}$ heteroaryl is optionally substituted with from one to five substituents independently selected from halo, oxo, —CN, $R^6$, and $R^7$;
each $R^6$ is independently selected from —OR$^8$, —N($R^8$)$R^9$, —NR$^8$C(O)R$^9$, —NHC(O)NR$^8$R$^9$, —NR$^8$C(O) NHR$^9$, —C(O)R$^8$, —C(O)OR$^8$, —C(O)N(R$^8$)R$^9$, —C(O)N(R$^8$)OR$^9$, —C(O)N($^8$)S(O)$_2$R$^7$, —N(R$^8$) S(O)$_2$R$^7$, —SR$^8$, —S(O)R$^7$, and —S(O)$_2$N(R$^8$)R$^9$;
each $R^7$ is independently selected from
  (a) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
  (b) $C_{3-10}$ cycloalkyl-(CH$_2$)$_m$—, $C_{6-14}$ aryl-(CH$_2$)$_m$—, $C_{2-6}$ heterocyclyl-(CH$_2$)$_m$—, and $C_{1-9}$ heteroaryl-(CH$_2$)$_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;
each $R^8$ and $R^9$ is independently selected from
  (a) hydrogen;
  (b) $C_{1-6}$ alkyl, $C_{2-6}$ alkenyl, and $C_{2-6}$ alkynyl, each optionally substituted with from one to five substituents independently selected from halo, oxo, —CN, and $R^{10}$; and
  (c) $C_{3-10}$ cycloalkyl-(CH$_2$)$_m$—, $C_{6-14}$ aryl-(CH$_2$)$_m$—, $C_{2-6}$ heterocyclyl-(CH$_2$)$_m$—, and $C_{1-9}$ heteroaryl-(CH$_2$)$_m$—, each optionally substituted with from one to five substituents independently selected from halo, oxo, —CN, $R^{10}$, and $C_{1-6}$ alkyl optionally substituted with from one to five substituents independently selected from halo, oxo, —CN, and $R^{10}$;
each $R^{10}$ is independently selected from —OR$^{11}$, —N(R$^{11}$)R$^{12}$, —N(R$^{11}$)C(O)R$^{12}$, —NHC(O)NR$^{11}$R$^{12}$, —NR$^{11}$C(O)MHR$^{12}$, —C(O)R$^{11}$, —C(O)OR$^{11}$, —C(O)N(R$^{11}$)R$^{12}$, —C(O)N(R$^{11}$)OR$^{12}$, —C(O)N(R$^{11}$)S(O)$_2$R$^{13}$, —NR$^{11}$S(O)$_2$R$^{13}$, —SR$^{11}$, —SR$^{11}$, —S(O)R$^{13}$, —S(O)$_2$R$^{13}$, and —S(O)$_2$N(R$^{11}$)R$^{12}$;
each $R^{11}$ and $R^{12}$ is independently selected from
  (a) hydrogen; and
  (b) $C_{1-6}$ alkyl and $C_{3-10}$ cycloalkyl-(CH$_2$)$_m$—, each optionally substituted with from one to five substituents independently selected from halo, oxo, —CN, —OH, and —NH$_2$;
each $R^{13}$ is independently selected from $C_{1-6}$ alkyl and $C_{3-10}$ cycloalkyl-(CH$_2$)$_m$—, each optionally substituted with from one to five substituents independently selected from halo, oxo, —CN, —OH, and —NH$_2$;
each $R^{14}$ is independently selected from hydrogen, $C_{1-4}$ alkyl, and $C_{1-4}$ haloalkyl; and
each m is independently selected from 0, 1, 2, 3, and 4;
wherein each heteroaryl and heterocyclyl moiety of $R^3$, $R^7$, $R^8$, and $R^9$ independently has one to four heteroatoms, each of the heteroatoms independently selected from N, O, and S.

2. A compound or pharmaceutically acceptable salt according to claim 1, wherein $R^2$, $R^3$, and $R^4$ are each independently selected from hydrogen, methyl, halo, and —OCH$_3$.

3. A compound or pharmaceutically acceptable salt according to claim 1, wherein each of $R^2$, $R^3$, and $R^4$ is hydrogen.

4. A compound or pharmaceutically acceptable salt according to claim 1, wherein $R^5$ is a bicyclic $C_{6-8}$ heteroaryl having from one to three heteroatoms, each of the heteroatoms being nitrogen, and wherein the $C_{6-8}$ heteroaryl is optionally substituted with from one to five substituents independently selected from halo, oxo, —CN, $R^6$, and $R^7$.

5. A compound or pharmaceutically acceptable salt according to claim 4, wherein the bicyclic $C_{6-8}$ heteroaryl of $R^5$ is an aromatic ring ortho-fused to a pyrrole, pyrazole, imidazole, triazole, pyrrolidine, pyrazolidine, imidazolidine or triazolidine ring, the aromatic ring is benzene or pyridine, and the bicyclic $C_{6-8}$ heteroaryl is optionally substituted with from one to four substituents independently selected from halo, oxo, —CN, $R^6$, and $R^7$.

6. A compound or pharmaceutically acceptable salt according to claim 1, wherein $R^5$ is selected from indazolyl, 1H-pyrazolo[4,3-b]pyridinyl, 1H-pyrazolo[3,4-b]pyridinyl, indolyl, isoindolyl, 1H-pyrrolo[3,2-b]pyridinyl, 1H-pyrrolo[2,3-b]pyridinyl, benzimidazolyl, benzotriazolyl, indolinyl, isoindolinyl, and benzimidazolinyl, each optionally substituted with from one to four substituents independently selected from halo, oxo, —CN, $R^6$, and $R^7$.

7. A compound or pharmaceutically acceptable salt according to claim 1, wherein $R^5$ is selected from 1H-indazol-5-yl, 1H-indazol-6-yl, 1H-pyrazolo[4,3-b]pyridin-5-yl, 1H-pyrazolo[4,3-b]pyridin-6-yl, 1H- pyrazolo[3,4-b]pyridin-5-yl, 1H-pyrazolo[3,4-b]pyridin-6-yl, 1H-indol-5-yl, 1H-indol -6-yl, 2H-isoindol-5-yl, 1H-pyrrolo[3,2-b]pyridin-5-yl, 1H-pyrrolo[3,2-b]pyridin-6-yl, 1H-pyrrolo[2,3-b]pyridin-5-yl, 1H- pyrrolo[2,3-b]pyridin-6-yl, 1H-benzo[d]imidazol-5-yl, 1H -benzo[d]imidazol-6-yl, 1H-benzo[d][1,2,3]triazol-5-yl, 1H-benzo[d][1,2,3]triazol-6-yl, indolin-5-yl, indolin-6-yl, isoindolin-5-yl, and 2,3-dihydro-1H-benzo[d]imidazol-5-yl, each optionally substituted with from one to four substituents independently selected from halo, oxo, —CN, $R^6$, and $R^7$.

8. A compound or pharmaceutically acceptable salt according to claim 1, wherein $R^5$ is selected from 1H-indazol-5-yl, 1H-indazol-6-yl, 1H-indol-5-yl, 1H-indol-6-yl, 2H-isoindol-5-yl, 1H-benzo[d]imidazol-5-yl, 1H-benzo[d]imidazol-6-yl, 1H-benzo [d][1,2,3]triazol-5-yl, 1H-benzo[d][1,2,3]triazol -6-yl, and isoindolin-5-yl, each optionally substituted with from one to four substituents independently selected from halo, oxo, —CN, $R^6$, and $R^7$.

9. A compound or pharmaceutically acceptable salt according to claim 1, wherein $R^5$ is selected from 1H-indazol-5-yl and 1H-indazol-6-yl, each optionally substituted with from one to four substituents independently selected from halo, oxo, —CN, $R^6$, and $R^7$.

10. A compound or pharmaceutically acceptable salt according to claim 4, wherein the bicyclic $C_{6-8}$ heteroaryl of $R^5$ is optionally substituted with from one to three substituents independently selected from halo, oxo, —CN, $C_{1-4}$ alkyl, and —$OR^8$, wherein $R^8$ is selected from hydrogen and $C_{1-4}$ alkyl.

11. A compound according to claim 1, which is selected from the following compounds:
4-amino-8-(1-methyl-1H-indazol-6-yl)cinnoline-3-carboxamide;
4-amino-8-(1-methyl-1H-indazol-5-yl)cinnoline-3-carboxamide;
4-amino-8-(1H-pyrrolo[3,2-b]pyridin-6-yl)cinnoline-3-carboxamide;
4-amino-8-(1H-benzo[d]imidazol-6-yl)cinnoline-3-carboxamide;
4-amino-8-(1-methyl-1H-indol-5-yl)cinnoline-3-carboxamide;
4-amino-8-(7-fluoro-2-oxoindolin-5-yl)cinnoline-3-carboxamide;
4-amino-8-(1-methylindolin-5-yl)cinnoline-3-carboxamide;
4-amino-8-(2-oxoindolin-5-yl)cinnoline-3-carboxamide;
4-amino-8-(1-methyl-1H-indol-6-yl)cinnoline-3-carboxamide;
4-amino-8-(imidazo[1,2-]pyridin-6-yl)cinnoline-3-carboxamide;
4-amino-8-(2-methyl-2H-indazol-5-yl)cinnoline-3-carboxamide;
4-amino-8-(1-methyl-1H-benzo[d]imidazol-5-yl)cinnoline -3-carboxamide;
4-amino-8-(3-methyl-3H-imidazo[4,5-b]pyridin-6-yl)cinnoline-3-carboxamide;
4-amino-8-(2-oxo-2,3-dihydro-1H-benzo[d]imidazol-5-yl)cinnoline-3-carboxamide;
4-amino-8-(1H-indo-6-yl)cinnoline-3-carboxamide;
4-amino-8-(2-methyl-1H-benzo[d]imidazol-6-yl)cinnoline -3-carboxamide;
4-amino-8-(1-isopropyl-1H-benzo[d]imidazol-5-yl)cinnoline -3-carboxamide;
4-amino-8-(1-cyclohexyl-1H-benzo[d]imidazol-5-yl)cinnoline -3-carboxamide;
4-amino-8-(1-tent-butyl-1H-benzo[d]imidazol-5-yl)cinnoline -3-carboxamide;
4-amino-8-(2-oxoindolin-6-yl)cinnoline-3-carboxamide;
4-amino-7-methyl-8-(1H-pyrrolo[3,2-b]pyridin-6-yl)cinnoline-3-carboxamide;
4-amino-8-(1H-benzo[c/]imidazol-6-yl)-7-methylcinnoline -3-carboxamide;
4-amino-7-methyl-8-(1-methyl-1H-benzo[d]imidazol-6-yl)cinnoline-3-carboxamide;
4-amino-8-(1H-indo-5-yl)-7-methylcinnoline-3-carboxamide;
4-amino-7-methyl-8-(1-methyl-1H-indazol-5-yl)cinnoline -3-carboxamide;
4-amino-8-(1H-indol-6-yl)-7-methylcinnoline-3-carboxamide;
4-amino-8-(1H-indol-5-yl)cinnoline-3-carboxamide;
4-amino-8-(1H-indazol-6-yl)-7-methylcinnoline-3-carboxamide;
4-amino-8-(1H-indazol-5-yl)-7-methylcinnoline-3-carboxamide;
4-amino-8-(1,4-dimethyl-1H-indazol-5-yl)cinnoline-3-carboxamide;
4-amino-8-(4-methyl-1H-indazol-5-yl)cinnoline-3-carboxamide;
4-amino-8-(1,7-dimethyl-1H-indazol-5-yl)-7-methylcinnoline-3-carboxamide;
4-amino-7-methyl-8-(7-methyl-1H-indazol-5-yl)cinnoline -3-carboxamide;
4-amino-8-(1-methyl-1H-indazol-5-yl)-6-(trifluoromethyl)cinnoline-3-carboxamide;
4-amino-8-(1-methyl-1H-indazol-5-yl)-7-(trifluoromethyl)cinnoline-3-carboxamide;
4-amino-8-(1,3-dimethyl-1H-indazol-5-yl)-7-methylcinnoline-3-carboxamide;
4-amino-8-(1,3-dimethyl-1H-indazol-5-yl)cinnoline-3-carboxamide;
4-amino-8-(1H-indazol-6-yl)-5-methoxycinnoline-3-carboxamide;
4-amino-5-methoxy-8-(5-methyl-1H-indazol-6-yl)cinnoline -3-carboxamide;
4-amino-8-(5-methyl-1H-indazol-6-yl)cinnoline-3-carboxamide;
4-amino-8-(1H-indazol-6-yl)-7-methoxycinnoline-3-carboxamide;
4-amino-8-(1H-indazol-6-yl)-5-methoxy-7-methylcinnoline -3-carboxamide;
4-amino-5-fluoro-8-(5-methyl-1H-indazol-6-yl)cinnoline -3-carboxamide;
4-amino-8-(1,5-dimethyl-1H-indazol-6-yl)cinnoline-3-carboxamide;
4-amino-7-methyl-8-(1-methyl-1H-indazol-6-yl)cinnoline -3-carboxamide;
4-amino-8-(1H-benzo[c/]imidazol-6-yl)-7-methoxycinnoline -3-carboxamide;
4-amino-7-methyl-8-(1H-pyrazolo[3,4-b]pyridin-5-yl)cinnoline-3-carboxamide;
4-amino-8-(1H-benzo [d] [ 1,2,3]triazol-5-yl) -7-methylcinnoline-3-carboxamide;
4-amino-8-(6-methyl-1H-indazol-5-yl)cinnoline-3-carboxamide;
4-amino-7-methyl-8-(3-methyl-1H-indazol-5-yl)cinnoline -3-carboxamide;

4-amino-8-(1H-indazol-5-yl)-7-methoxycinnoline-3-carboxamide;
4-amino-7-methyl-8-(2-methyl-2H-indazol-6-yl)cinnoline-3-carboxamide;
4-amino-8-(1H-indazol-6-yl)-5,7-dimethylcinnoline-3-carboxamide;
4-amino-7-chloro-8-(1H-indazol-6-yl)cinnoline-3-carboxamide;
4-amino-8-(1,6-dimethyl-1H-indazol-5-yl)cinnoline-3-carboxamide;
4-amino-5-fluoro-8-(1H-indazol-6-yl)-7-methylcinnoline-3-carboxamide;
4-amino-8-(isoquinolin-7-yl)-7-methylcinnoline-3-carboxamide;
4-amino-8-(isoquinolin-6-yl)-7-methylcinnoline-3-carboxamide;
4-amino-8-(1H-indazol-6-yl)cinnoline-3-carboxamide;
4-amino-5-fluoro-8-(1H-indazol-5-yl)-7-methylcinnoline-3-carboxamide;
4-amino-7-ethyl-8-(1H-indazol-6-yl)cinnoline-3-carboxamide;
4-amino-7-ethyl-8-(1H-indazol-5-yl)cinnoline-3-carboxamide;
4-amino-7-methyl-8-(1-oxo-1,2,3,4-tetrahydroisoquinolin-6-yl)cinnoline-3-carboxamide;
4-amino-6-methyl-8-(5-methyl-1H-indazol-6-yl)cinnoline-3-carboxamide;
4-amino-8-(2-((cyclopropylmethyl)amino)-1H-benzo[d]imidazol-6-yl)cinnoline-3-carboxamide;
4-amino-8-(2-neopentyl-1H-benzo[d]imidazol-6-yl)cinnoline-3-carboxamide;
4-amino-8-(2-(3,5-dichlorophenyl)-1H-benzo[d]imidazol-6-yl)cinnoline-3-carboxamide;
4-amino-8-(2-cyclohexyl-1H-benzo[d]imidazol-6-yl)cinnoline-3-carboxamide;
4-amino-8-(2-phenethyl-1H-benzo[d]imidazol-6-yl)cinnoline-3-carboxamide;
4-amino-8-(2-(2-chlorophenyl)-1H-benzo[d]imidazol-6-yl)cinnoline-3-carboxamide;
4-amino-8-(2-(3-(trifluoromethyl)phenyl)-1H-benzo[d]imidazol-6-yl)cinnoline-3-carboxamide;
4-amino-8-(2-cyclopentyl-1H-benzo[d]imidazol-6-yl)cinnoline-3-carboxamide;
4-amino-8-(2-(thiophen-3-yl)-1H-benzo[d]imidazol-6-yl)cinnoline-3-carboxamide;
4-amino-8-(2-(4-methoxyphenyl)-1H-benzo[d]imidazol-6-yl)cinnoline-3-carboxamide;
4-amino-8-(2-(imidazo[1,2-a]pyridin-2-yl)-1H-benzo[d]imidazol-6-yl)cinnoline-3-carboxamide;
4-amino-8-(2-(3-chlorophenyl)-1H-benzo[d]imidazol-6-yl)cinnoline-3-carboxamide;
4-amino-8-(2-benzyl-1H-benzo[d]imidazol-6-yl)cinnoline-3-carboxamide;
4-amino-8-(2-(cyclohexylmethyl)-1H-benzo[d]imidazol-6-yl)cinnoline-3-carboxamide;
4-amino-8-(2-(thiophen-2-yl)-1H-benzo[d]imidazol-6-yl)cinnoline-3-carboxamide;
4-amino-8-(2-(3,5-dimethylphenyl)-1H-benzo[d]imidazol-6-yl)cinnoline-3-carboxamide;
4-amino-8-(2-((tetrahydro-2H-pyran-4-yl)methyl)-1H-benzo[d]imidazol-6-yl)cinnoline-3-carboxamide;
4-amino-8-(2-(thiazol-5-yl)-1H-benzo[d]imidazol-6-yl)cinnoline-3-carboxamide;
4-amino-8-(2-(tetrahydro-2H-pyran-3-yl)-1H-benzo[d]imidazol-6-yl)cinnoline-3-carboxamide;
4-amino-8-(2-(4,4-difluorocyclohexyl)-1H-benzo[d]imidazol-6-yl)cinnoline-3-carboxamide;
4-amino-8-(4,5-dihydro-1H-pyrazolo[3,4-c]pyridin-6(7H)-yl)cinnoline-3-carboxamide;
4-amino-8-(6,7-dihydro-1H-pyrazolo[4,3-c]pyridin-5(4H)-yl)cinnoline-3-carboxamide;
4-amino-8-(2-(phenylamino)-1H-benzo[d]imidazol-6-yl)cinnoline-3-carboxamide;
4-amino-8-(2-(thiophen-2-ylmethylamino)-1H-benzo[d]imidazol-6-yl)cinnoline-3-carboxamide;
4-amino-8-(2-(cyclobutylamino)-1H-benzo[d]imidazol-6-yl)cinnoline-3-carboxamide;
4-amino-8-(2-(benzylamino)-1H-benzo[d]imidazol-6-yl)cinnoline-3-carboxamide;
4-amino-8-(2-(4-methylcyclohexylamino)-1H-benzo[d]imidazol-6-yl)cinnoline-3-carboxamide;
4-amino-8-(2-(benzyl(methyl)amino)-1H-benzo[d]imidazol-6-yl)cinnoline-3-carboxamide;
4-amino-8-(2-(cyclopentylmethylamino)-1H-benzo[d]imidazol-6-yl)cinnoline-3-carboxamide;
8-(2-((adamantan-2-ylmethyl)amino)-1H-benzo[d]imidazol-6-yl)-4-aminocinnoline-3-carboxamide;
4-amino-8-(2-(4-methylbenzylamino)-1H-benzo[d]imidazol-6-yl)cinnoline-3-carboxamide;
4-amino-8-(3-cyano-1H-indazol-6-yl)-7-methylcinnoline-3-carboxamide;
4-amino-7-methyl-8-(1-methyl-1H-imidazo[4,5-b]pyridin-6-yl)cinnoline-3-carboxamide;
4-amino-7-methyl-8-(3-methyl-3H-imidazo[4,5-b]pyridin-6-yl)cinnoline-3-carboxamide;
4-amino-7-methyl-8-(3-methyl-1H-indazol-6-yl)cinnoline-3-carboxamide;
4-amino-8-(3-fluoro-1H-indazol-6-yl)-7-methylcinnoline-3-carboxamide;
4-amino-8-(4-fluoro-1H-benzo[d]imidazol-6-yl)-7-methylcinnoline-3-carboxamide;
4-amino-8-(4-fluoro-1H-indazol-6-yl)-7-methylcinnoline-3-carboxamide;
4-amino-8-(6-methoxy-1H-indazol-5-yl)cinnoline-3-carboxamide;
4-amino-8-(7-fluoro-1H-indazol-6-yl)-7-methylcinnoline-3-carboxamide;
4-amino-8-(5-chloro-1H-indazol-6-yl)cinnoline-3-carboxamide;
4-amino-8-(3-cyclopropyl-1H-indazol-6-yl)-7-methylcinnoline-3-carboxamide;
4-amino-8-(5-chloro-1H-indazol-6-yl)-5-fluorocinnoline-3-carboxamide;
4-amino-8-(3-chloro-1H-indazol-6-yl)-7-methylcinnoline-3-carboxamide;
4-amino-5-fluoro-8-(6-methoxy-1H-indazol-5-yl)cinnoline-3-carboxamide;
4-amino-8-(5-methoxy-1H-indazol-6-yl)cinnoline-3-carboxamide;
4-amino-5-fluoro-8-(5-methoxy-1H-indazol-6-yl)cinnoline-3-carboxamide;
8-([1,2,4]triazolo[4,3-a]pyridin-6-yl)-4-amino-7-methylcinnoline-3-carboxamide;
4-amino-8-(imidazo[1,5-a]pyridin-6-yl)-7-methylcinnoline-3-carboxamide;
4-amino-8-(imidazo[1,5-a]pyridin-7-yl)-7-methylcinnoline-3-carboxamide;
4-amino-8-(2-phenyl-1H-benzo[d]imidazol-6-yl)cinnoline-3-carboxamide;
4-amino-8-(2-(4-fluorophenyl)-1H-benzo[d]imidazol-6-yl)cinnoline-3-carboxamide;
4-amino-8-(2-(4-tert-butylphenyl)-1H-benzo[d]imidazol-6-yl)cinnoline-3-carboxamide;

4-amino-8-(2-(2,4-difluorophenyl)-1H-benzo[d] imidazol-6-yl)cinnoline-3-carboxamide;
4-amino-8-(2-(4-fluoro-2-methoxyphenyl)-1H-benzo[d]imidazol-6-yl)cinnoline-3-carboxamide;
4-amino-8-(2-(4-fluorophenyl)-1H-benzo[d]imidazol-6-yl)-7-methylcinnoline-3-carboxamide;
4-amino-8-(1-oxo-2-phenylisoindolin-5-yl)cinnoline-3-carboxamide;
4-amino-8-(1-oxo-2-phenylisoindolin-5-yl)cinnoline-3-carboxamide;
4-amino-8-(2-methyl-1-oxoisoindolin-5-yl)cinnoline-3-carboxamide;
4-amino-7-methyl-8-(1-oxoisoindolin-5-yl)cinnoline-3-carboxamide;
4-amino-5-fluoro-8-(1-oxoisoindolin-5-yl)cinnoline-3-carboxamide;
4-amino-5-fluoro-7-methyl-8-(1-oxoisoindolin-5-yl)cinnoline-3-carboxamide;
4-amino-8-(2-(3-hydroxy-3-methylbutyl)-1-oxoisoindolin-5-yl)cinnoline-3-carboxamide;
4-amino-8-(2-(3-hydroxy-3-methylbutyl)-1-oxoisoindolin-5-yl)-7-methylcinnoline-3-carboxamide;
4-amino-7-ethyl-8-(1-oxoisoindolin-5-yl)cinnoline-3-carboxamide;
4-amino-8-(2-cyano-1H-benzo[d]imidazol-6-yl)cinnoline-3-carboxamide;
4-amino-8-(1-ethyl-1H-benzo[d]imidazol-6-yl)-7-methylcinnoline-3-carboxamide;
4-amino-8-(1-ethyl-1H-benzo[d]imidazol-5-yl)-7-methylcinnoline-3-carboxamide;
4-amino-8-(1-(2-cyanoethyl)-1H-benzo[d]imidazol-6-yl)-7-methylcinnoline-3-carboxamide;
4-amino-8-(1-(2-hydroxyethyl)-1H-benzo[d]imidazol-6-yl)-7-methylcinnoline-3-carboxamide ;
4-amino-7-cyano-8-(1H-indazol-6-yl)cinnoline-3-carboxamide;
4-amino-8-(5-methyl-1H-indazol-6-yl)-6-morpholinocinnoline-3-carboxamide;
4-amino-6-(4-hydroxypiperidin-1-yl)-8-(5-methyl-1H-indazol-6-yl)cinnoline-3-carboxamide;
4-amino-6-fluoro-8-(5-methyl-1H-indazol-6-yl)cinnoline-3-carboxamide; and
a pharmaceutically acceptable salt of any of the aforementioned compounds.

12. A pharmaceutical composition comprising:
a compound or pharmaceutically acceptable salt as defined in claim 1; and
a pharmaceutically acceptable excipient.

13. A combination comprising an effective amount of a compound or pharmaceutically acceptable salt as defined in claim 1, and at least one additional pharmacologically active agent.

14. A combination according to claim 13, wherein the additional pharmacologically active agent is a DMARD.

15. A combination according to claim 14, wherein the DMARD is methotrexate.

16. A method of treating a disease, disorder or condition in a subject, the method comprising administering to the subject an effective amount of a compound or a pharmaceutically acceptable salt as defined in claim 1, wherein the disease, disorder or condition is rheumatoid arthritis.

* * * * *